US006031153A

United States Patent [19]
Ryals et al.

[11] Patent Number: 6,031,153
[45] Date of Patent: Feb. 29, 2000

[54] METHOD FOR PROTECTING PLANTS

[75] Inventors: John Andrew Ryals, Cary; Leslie Bethards Friedrich; Scott Joseph Uknes, both of Apex, all of N.C.; Antonio Molina-Fernandez, Blanca, Spain; Wilhelm Ruess, Pfeffingen, Switzerland; Gertrude Knauf-Beiter, Mullheim, Germany; Ruth Beatrice Kung; Helmut Kessmann, both of Allschwil, Switzerland; Michael Oostendorp, Rheinfelden, Germany

[73] Assignee: Novartis AG, Basel, Switzerland

[21] Appl. No.: 08/996,685

[22] Filed: Dec. 23, 1997

Related U.S. Application Data

[63] Continuation-in-part of application No. 08/761,543, Dec. 6, 1996, Pat. No. 5,780,469, and a continuation-in-part of application No. 08/875,015, and a continuation-in-part of application No. PCT/EP96/02672, Jun. 20, 1996.
[60] Provisional application No. 60/034,378, Dec. 27, 1996, provisional application No. 60/034,379, Dec. 27, 1996, provisional application No. 60/034,382, Dec. 27, 1996, provisional application No. 60/034,730, Jan. 10, 1997, provisional application No. 60/035,021, Jan. 10, 1997, provisional application No. 60/035,022, Jan. 10, 1997, and provisional application No. 60/035,024, Jan. 10, 1997.

[30] Foreign Application Priority Data

Jan. 23, 1995 [CH] Switzerland ............................. 179/95
Jun. 29, 1995 [CH] Switzerland ........................... 1910/95
Dec. 11, 1995 [CH] Switzerland ........................... 3495/95

[51] Int. Cl.[7] .............................. C12Q 1/70; C12P 21/06; A01H 4/00; C12N 5/04
[52] U.S. Cl. ............................ 800/279; 435/5; 435/69.1; 800/278; 800/320; 800/307; 800/317.3; 800/320.2; 800/317.1; 800/317.4; 47/58.1
[58] Field of Search ....................... 435/5, 69.1; 800/278, 800/279, 320, 307, 317.3, 320.2, 317.1, 317.4; 47/58.1

[56] References Cited

U.S. PATENT DOCUMENTS 5,523,311 6/1996 Schurter et al. .
5,614,395 3/1997 Ryals et al. .

FOREIGN PATENT DOCUMENTS 0 534 858 3/1993 European Pat. Off. .
WO 94/16077 7/1994 WIPO .
WO 95/19443 7/1995 WIPO .

OTHER PUBLICATIONS

Napoli et al. The Plant Cell. 1989. vol. 2: 278–289.
Linthorst et al. Plant Cell. 1989. vol. 1: 289–291.
Carvalho et al. The EMBO J. 1992. vol. 11: 2595–2602.
Hennig et al. The Plant Journal. 1993. Vol. 4: 481–493.
Uknes et al. The Plant Cell. 1992. vol. 4: 645–656.
Genbank Accession No. T22612, Cao et al., Cell 88(1): 575–63 (1997).
Genbank Accession No. U76707, Newman et al., Plant Physiol., 106: 1241–1255 (1994).
Dong et al., U.S. Provisional Application No. 60/023,851, filed Aug. 9, 1996.
Dong et al., U.S. Provisional Application No. 60/035,166, filed Jan. 10, 1997.
Hunt et al., Recent advances in systemic acquired resistance research—a review, Gene, 179: 89–95 (1996).
Adaskaveg and Hine, "Copper Tolerance and Zinc Sensitivity of Mexican Strains of *Xanthomonas campestris* pv. *vesicatoria*, Causal Agent of Bacterial Spot of Pepper", *Plant Disease*, 69: 993–996 (1985).
Alexander et al., "Increased tolerance to two oomycete pathogens in transgenic tobacco expressing pathogenesis–related protein 1a", *Proc. Natl. acad. Sci.* 90: 7327–7331 (1993).
Baeuerle and Baltimore, "NF–κB: Ten Years After", *Cell*, 87: 13–20 (1996).
Baldwin, A.S., "The NF–κB: and IκB Proteins: New Discoveries and Insights", *Annu. Rev. Immunol.*, 14: 649–681 (1996).
Barak and Edgington, "The role of glutathione in the resistance of *Botrytis cinerea* to captan", *Canadian Journal of Plant Pathology*, 5: 200 (1983).
Beg and Baltimore, "An Essential Role for NF–κB in Preventing TNF–α–Induced Cell Death", *Science*, 274: 782–784 (1996).
Bell et al., "Assignment of 30 Microsatellite Loci to the Linkage Map of Arabidopsis", *Genomics*, 19: 137–144 (1994).
Bhat, K.S., "Generation of a plasmid vector for deletion cloning by rapid multiple site–directed mutagenesis", *Gene*, 134: 83–87 (1993).
Bi et al., "Hydrogen peroxide does not function downstream of salicylic acid in the induction of PR protein expression", *The Plant Journal*, 8(2): 235–245 (1995).
Bleecker et al., "Insensitivity to Ethylene Conferred by a Dominant Mutation in *Arabidopsis thaliana*", *Science*, 241: 1086–1089 (1988).

(List continued on next page.)

*Primary Examiner*—Elizabeth F. McElwain
*Assistant Examiner*—Ousama M-Faiz Zaghmout
*Attorney, Agent, or Firm*—J. Timothy Meigs

[57] ABSTRACT

The present invention concerns a method of protecting plants from pathogen attack through synergistic disease resistance attained by applying a conventional microbicide to immunomodulated plants. Immunomodulated plants are those in which SAR is activated and are therefore referred to as "SAR-on" plants. Immunomodulated plants may be provided in at least three different ways: by applying to plants a chemical inducer of SAR such as BTH, INA, or SA; through a selective breeding program based on constitutive expression of SAR genes and/or a disease-resistant phenotype; or by transforming plants with one or more SAR genes such as a functional form of the NIM1 gene. By concurrently applying a microbicide to an immunomodulated plant, disease resistance is unexpectedly synergistically enhanced; i.e., the level of disease resistance is greater than the expected additive levels of disease resistance.

32 Claims, 4 Drawing Sheets

OTHER PUBLICATIONS

Börner et al., "Influence of the systemic fungicide metalaxyl on glyceollin accumulation in soybean infected with *Phytophthora megasperma* f. sp. *glycinea*", *Physiological Plant Pathology*, 23: 145–152 (1983).

Bouchez et al., "A new YAC library for genome mapping in Arabidopsis", Abstract, 6th International Conference on Arabidopsis Research (1995).

Bowling et al., "A Mutation in Arabidopsis That Leads to Constitutive Expression of Systemic Acquired Resistance", *The Plant Cell*, 6: 1845–1857 (1994).

Bowling et al., "The cpr5 Mutant of Arabidopsis Expresses Both NPR1–Dependent and NPR1–Independent Resistance", *The Plant Cell*, 9: 1573–1584 (1997).

Brockman et al., "Coupling of a Signal Response Domain in IκBα to Multiple Pathways for NF–κB Activation", *Molecular and Cellular Biology*, 15: 2809–2818 (1995).

Brown et al., "Control of IκB–α Proteolysis by Site–Specific, Signal–Induced Phosphorylation", *Science*, 267: 1485–1488 (1995).

Büschges et al., "The Barley Mlo Gene: A Novel Control Element of Plant Pathogen Resistance", *Cell*, 88: 695–704 (1997).

Cameron et al., "Biologically induced systemic acquired resistance in *Arabidopsis thaliana*", *The Plant Journal* 5(5): 715–725 (1994).

Cao et al., "Characterization of an Arabidopsis Mutant That Is Nonresponsive to Inducers of Systemic Acquired Resistance", *The Plant Cell*, 6: 1583–1592 (1994).

Cao et al., "The Arabidopsis NPR1 Gene that Controls Systemic Acquired Resistance Encodes a Novel Protein Containing Ankyrin Repeats", *Cell* , 88: 57–63 (1997).

Cartwright et al., "Chemical activation of host defence mechanisms as a basis for crop protection", *Nature*, 267: 511–513 (1977).

Century et al., "NDR1, a locus of *Arabidopsis thaliana* that is required for disease resistance to both a bacterial and a fungal protein", *Proc. Natl. Acad. Sci.*, 92: 6597–6601 (1995).

Creusot et al., "The CIC library: a large insert YAC library for genome mapping in *Arabidopsis thaliana*", *The Plant Journal*, 8(5): 763–770 (1995).

Dangl et al., "Death Don't Have No Mercy: Cell Death Programs in Plant–Microbe Interactions", *The Plant Cell*, 8: 1793–1807 (1996).

Delaney et al., "A Central Role of Salicylic Acid in Plant Disease Resistance", *Science*, 266: 1247–1250 (1994).

Delaney et al., "Arabidopsis signal transduction mutants defective in chemically and biologically induced disease resistance", Abstract, 6th International Meeting on Arabidopsis Research, (1995).

Delaney et al., "Arabidopisis signal transduction mutant defective in chemically and biologically induced disease resistance", *Proc. Natl. Acad. Sci.*, 92: 6602–6606 (1995).

Delaney, T.P., "Genetic Dissection of Acquired Resistance to Disease", *Plant Physiol*. 113: 1–12 (1997).

de Martin et al., "Cytokine–inducible expression in endothelial cells of an IκBα–like gene is regulated by NFκB", *EMBO J*. 12: 2773–2779 (1993).

de Martin et al., "Intron–exon structure of the porcine IκBα–encoding gene . . . ", *Gene*, 152: 253–255 (1995).

Dietrich et al., "Arabidopsis Mutants Simulating Disease Resistance Response", *Cell* 77: 565–577 (1994).

Draper, J., "Salicylate, superoxide synthesis and cell suicide in plant defence", *Trends in Plant Science*, 2: 162–165 (1997).

Ecker and Davis, "Plant defense genes are regulated by ethylene", *Proc. Natl. Acad. Sci., USA*, 84: 5202–5206 (1987).

Elledge et al., "λYES: A multifunctional cDNA expression vector for the isolation of genes by complementation of yeast and *Escherichia coli* mutations", *Proc. Natl. Acad. Sci., USA*, 88: 1731–1735 (1991).

Fisher and Hayes, "Mode of Action of the Systemic Fungicides Furalaxyl, Metalaxyl and Ofurace", *Pesticide Science*, 13: 330–339 (1982).

Friedrich et al., "A benzothiadiazole derivative induces systemic acquired resistance in tobacco", *The Plant Journal*, 10: 61–70 (1996).

Gaffney et al., "Requirement of Salicylic Acid for the Induction of Systemic Acquired Resistance", *Science* 261: 754–756 (1993).

Gatz C., "Chemical Control of Gene Expression", *Ann. Rev. Plant Physiol. Plant Mol. Biol*. 48: 89–108 (1997).

Glazebrook et al., "Isolation of Arabidopsis Mutants With Enhanced Disease Susceptibility by Direct Screening", *Genetics* 143: 973–982 (1996).

Görlach et al., "Benzothiadiazole, a Novel Class of Inducers of Systemic Acquired Resistance, Activates Gene Expression and Disease Resistance in Wheat", *The Plant Cell* 8: 629–643 (1996).

Greenberg et al., "Programmed Cell Death in Plants: A Pathogen–Triggered Response Activated Coordinately with Multiple Defense Functions", *Cell* 77:551–563 (1994).

Guest, D.I., "Modification of defence responses in tobacco and capsicum following treatment with Fosetyl–Al [Aluminium tris (o–ethyl phosphonate)]", *Physiological Plant Pathology*, 25: 125–134 (1984).

Guzmán and Ecker, "Exploiting the Triple Response of Arabidopsis To Identify Ethylene–Related Mutants", *Plant Cell*, 2: 513–523 (1990).

Hebsgaard et al., "Splice site prediction in *Arabidopsis thaliana* pre–mRNA by combining local and global sequence information", *Nucleic Acids Research* 24: 3439–3452 (1996).

Hunt and Ryals, "Systemic Acquired Resistance Signal Transduction", *Critical Reviews in Plant Sciences* 15: 583–606 (1996).

Ip et al., "Dif, a dorsal–Related Gene That Mediates an Immune Response in Drosophila", *Cell*, 75: 753–763 (1993).

Jones et al., "Population Dynamics of *Xanthomonas campestris* pv. *vesicatoria* on Tomato Leaflets Treated with Copper Bactericides", *Phytopathology*, 81: 714–719 (1991).

Keen et al., "Effects of Glyphosate on Glyceollin Production and the Expression of Resistance to *Phytophthora megasperma* f. sp. *glycinea* in Soybean", *Phytopathology*, 72: 1467–1470 (1982).

Kessmann et al., "Induction of Systemic Acquired Disease Resistance in Plants by Chemicals", *Annu. Rev. Phytopathol.* 32: 439–459 (1994).

Király et al., "Hypersensitivity as a Consequence, Not the Cause, of Plant Resistance to Infection", *Nature*, 239: 456–458 (1972).

Kopp and Ghosh, "Inhibition of NF–κB by Sodium Salicylate and Aspirin", *Science*, 265: 956–959 (1994).

Langcake and Wickens, "Studies on the action of the dichlorocyclopropanes on the host–parasite relationship in the rice blast disease", *Physiological Plant Pathology*, 7: 113–126 (1975).

Lawton et al., "The Molecular Biology of Systemic Acquired Resistance", *Mechanisms of Plant Defense Responses*, B. Fritig and M. Legrand (eds.) Kluwer Academic Publishers (Netherlands) 422–432 (1993).

Lawton et al., "Systemic Acquired Resistance in Arabidopsis Requires Salicylic Acid but Not Ethylene", *Molecular Plant–Microbe Interactions* 8: 863–870 (1995).

Lawton et al., "Benzothiadiazole induces disease resistance in Arabidopsis by activation of the systemic acquired resistance signal transduction pathway" *The Plant Journal* 10: 71–82 (1996).

Lemaitre et al., "The Dorsoventral Regulatory Gene Cassette spätzle/Toll/cactus Controls the Potent Antifungal Response in Drosophila Adults", *Cell* 86: 973–983 (1996).

Lister and Dean, "Recombinant inbred lines for mapping RFLP and phenotypic markers in *Arabidopsis thaliana*" *The Plant Journal* 4: 745–750 (1993).

Liu et al., "Generation of a high–quality P1 library of Arabidopsis suitable for chromosome walking", *The Plant Journal* 7: 351–358 (1995).

Maher et al., "Increased disease susceptibility of transgenic tobacco plants with suppressed levels of preformed phenylpropanoid products", *Proc. Natl. Acad. Sci., USA*, 91: 7802–7806 (1994).

Mauch–Mani et al., "Systemic Acquired Resistance in *Arabidopsis thaliana* Induced by a Predisposing Infection with a Pathogenic Isolate of *Fusarium oxysporum*", *Molecular Plant–Microbe Interactions* 7: 378–383 (1994).

Mauch–Mani et al., "Production of Salicylic Acid Precursors Is A Major Function of Phenylalanine Ammonia–Lyase in the Resistance of Arabidopsis to *Peronospora parasitica*", *The Plant Cell* 8: 203–212 (1996).

Métraux et al., "Increase in Salicylic Acid at the Onset of Systemic Acquired Resistance in Cucumber", *Science* 250: 1004–1006 (1990).

Michaely and Bennett, "The ANK repeat: a ubiquitous motif involved in macromolecular recognition", *Trends in Cell Biology* 2: 127–129 (1992).

Mindrinos et al., "The *A. thaliana* Disease Resistance Gene RPS2 Encodes a Protein Containing a Nucleotide–Binding Site and Leucine–Rich Repeats", *Cell* 78: 1089–1099 (1994).

*Nature Created The Concept, The Plant Activator*, Ciba–Geigy AG Product Literature (1996).

Nemestothy and Guest, "Phytoalexin accumulation, phenylalanine ammonia lyase activity and ethylene biosynthesis in fosetyl–Al treated resistant and susceptible tobacco cultivars infected with *Phytophthora nicotianae* var. *nicotianae*", *Physiological and Molecular Plant Pathology*, 37: 207–219 (1990).

Pallas et al., "Tobacco plants epigenetically suppressed in phenylalanine ammonia–lyase expression do not develop systemic acquired resistance in response to infection by tobacco mosaic virus", *The Plant Journal* 10: 281–293 (1996).

Parker et al., "Characterization of eds1, a Mutation in Arabidopsis Suppressing Resistance to *Peronospora parasitica* Specified by Several Different RPP Genes", *The Plant Cell* 8: 2033–2046 (1996).

Payne et al., "Isolation of the genomic clone for pathogenesis–related protein 1a from *Nicotiana tabacum* cv. Xanthi–nc", *Plant Molecular Biology* 11: 89–94 (1988).

Ryals et al., "Signal transduction in systemic acquired resistance", *Proc. Natl. Acad. Sci. USA* 92: 4202–4205 (1995).

Ryals et al., "Systemic Acquired Resistance", *The Plant Cell* 8: 1809–1819 (1996).

Ryals et al., "The Arabidopsis NIM1 Protein Shows Homology to the Mammalian Transcription Factor Inhibitor IkB", *The Plant Cell* 9: 425–439 (1997).

Ryan, C.A., "The search for the proteinase inhibitor–inducing factor, PIIF", *Plant Molecular Biology*, 19: 123–133 (1992).

Service, R.F., "Closing In on a Stomach–Sparing Aspirin Substitute", *Science*, 273: 1660 (1996).

Shah et al., "Characterization of a Salicylic Acid–Insensitive Mutant (sai1) of *Arabidopsis thaliana*, Identified in a Selective Screen Utlizing the SA–Inducible Expression of the tms2 Gene", *Molecular Plant–Microbe Interactions*, 10: 69–78 (1997).

Shirasu et al., "Salicylic Acid Potentiates an Agonist–Dependent Gain Control That Amplifies Pathogen Signals in the Activation of Defense Mechanisms", *Plant Cell*, 9: 261–270 (1997).

Shulaev, et al., "Is Salicylic Acid a Translocated Signal of Systemic Acquired Resistance in Tobacco?", *The Plant Cell* 7: 1691–1701 (1995).

Simeons et al., "Isolation of genes expressed in specific tissues of *Arabidopsis thaliana* by differential screening of a genomic library", *Gene* 67: 1–11 (1988).

Staswick et al., "Methyl jasmonate inhibition of root growth and induction of a leaf protein are decreased in an *Arabidopsis thaliana* mutant", *Proc. Natl. Acad. Sci. USA*, 89: 6837–6840 (1992).

Sun et al., "Both Amino– and Carboxyl–Terminal Sequences within IκBα Regulate Its Inducible Degradation", *Molecular and Cellular Biology*, 16: 1058–1065 (1996).

Tewari et al., "Sequence of rat RL/IF–1 encoding IKBβ–like activity and comparison with related proteins containing notch–like repeats", *Nucleic Acids Research*, 20: 607 (1992).

Traenckner, E.Britta–Mareen et al., "Phosphorylation of human IκB–α of serines 32 and 36 controls IκB–α proteolysis and NF–κB activation in response to diverse stimuli", *EMBO Journal*, 14: 2876–2883 (1995).

Uknes et al., "Acquired Resistance in Arabidopsis", *The Plant Cell* 4: 645–656 (1992).

Uknes et al., "Regulation of Pathogenesis–Related Protein–1a Gene Expression in Tobacco", *The Plant Cell* 5: 159–169 (1993).

Uknes et al., "Biological Induction of Systemic Acquired Resistance in Arabidopsis", *Molecular Plant–Microbe Interactions* 6: 692–698 (1993).

Uknes et al., "Reduction of risk for growers: methods for the development of disease–resistant crops", *New Phytol.* 133: 3–10 (1996).

Van Antwerp et al., "Suppression of TNF–α–Induced Apoptosis by NF–κB", *Science*, 274: 787–789 (1996).

Vernooij et al., "Salicylic Acid Is Not the Translocated Signal Responsible for Inducing Systemic Acquired Resistance but Is Required in Signal Transcuction", *The Plant Cell* 6: 959–965 (1994).

Vernooij et al., "2,6–Dichloroisonicotinic Acid–Induced Resistance to Pathogens Without the Accumulation of Salicylic Acid", *Molecular Plant–Microbe Interactions* 8: 228–234 (1995).

Verwoerd et al., "A Small–scale procedure for the rapid isolation of plant RNAs", *Nucleic Acids Research* 17: 2362 (1989).

Vos et al., "AFLP: a new technique for DNA fingerprinting", *Nucleic Acids Research* 23: 4407–4414 (1995).

Wang et al., "TNF– and Cancer Therapy–Induced Apoptosis: Potentiation by Inhibition of NF–κB", *Science*, 274: 784–787 (1996).

Ward, E.W.B., "Suppression of metalaxyl activity by glyphosate: evidence that host defence mechanisms contribute to metalaxyl inhibition of *Phytophthora megasperma* f. sp. *glycinea* in soybeans", *Physiological Plant Pathology*, 25: 381–386 (1984).

Ward et al., "Glyceollin Production Associated with Control of Phytophthora Rot of Soybeans by the Systemic Fungicide, Metalaxyl", *Phytopathology* 70: 738–740 (1980).

Ward et al., "Coordinate Gene Activity in Response to Agents That Induce Systemic Acquired Resistance", *The Plant Cell* 3: 1085–1094 (1991).

Weymann et al., "Suppression and Restoration of Lesion Formation in Arabidopsis Isd Mutants", *The Plant Cell* 7: 2013–2022 (1995).

GenBank Accession No.: U76707.

GenBank Accession No.: T22612.

```
                                                                                                    98
1    MDTITDGFADSYEISSTSFVATNIDSSIVYLAAEQVLTGP..DMVSALQLLSNSFESVFDSPDDFYSDAKLVLSDGREVSFHRCVLSARSSFFKSALAAA
NIM1
MOUSE I-κBα     M..............FQPAGHGQ..............DWAMEGPRIDCLKKERLVDDRHDSGLDSMKD..EEYEQMVKELREIRLQPQ.........EAPLAAE   64
RAT I-κBα       M..............FQPAGHGQ..............DWAMEGPRIDCLKKERLVDDRHDSGLDSMKD..EDYEQMVKELREIRLQPQ.........EAPLAAE   64
PIG I-κBα       M..............FQPAEPGQ..............EWAMEGPRDALKKERLLDDRHDSGLDSMKD..EEYEQMVKELREIRLEPQ.........EAPRGAE   64

101  KKEKDSNNTAAVK.LEIKEIAKDYEVGFDSVVTVLAYVYSSRVRPPKGVSECADENCCHVACRPAVDFMLEVLYLAFIFKIPELITLYQRHLLDVVDKV       197
NIM1
MOUSE I-κBα     PW.KQQLTEDGDSFLHLAIIHEEKPLTMEVIGQV..................KG.........................DLAFLNFQNNLQQ.TPL...HLAVITNQP   124
RAT I-κBα       PW.KQQLTEDGDSFLHLAIIHEEKTLTMEVIGQV..................KG.........................DLAFLNFQNNLQQ.TPL...HLAVITNQP   124
PIG I-κBα       PW.KQQLTEDGDSFLHLAIIHEEKALTMEVVRQV..................KG.........................DLAFLNFQNNLQQ.TPL...HLAVITNQP   124

201  VIEDTLVILKLANICGKA.QMKLLDRCKEIIVKSNVDMVSLEKSLPEEIVKEIIDRRKELGLEVPKVKKHVSNVHKALDSDDIELVKLLLKEDHINLDDA                296
NIM1
MOUSE I-κBα     GIAFALL.........KAGCDPEL...RDFRGNTPLHLACEQGCLASVAV.............LTQICTPQHL...HSVLQAINYN...GHT..........   185
RAT I-κBα       GIAFALL.........KAGCDPEL...RDFRGNTPLHLACEQGCLASVAV.............LTQICTPQHL...HSVLQAINYN...GHT..........   185
PIG I-κBα       EIAFALL.........FAGCDPEL...RDFRGNTPLHLACEQGCLASVGV.............LTQPRGIQHL...HSTILQAINYN...GHT..........   185
```

FIGURE 1A

```
                  301                         +                         +                         +                        350                         +                         +                         +                        400
NIM1              CALHFAVAYCNVKTAIDLLKLDLADVNHRNP.RGYTVLHVAAMRKEPQLILSLLEK.GASASFATLEGRTALMLAKQAITMAVECNNIPEQCKHSLKGRLC        394
MOUSE I-κBα       C.LHLASIHGYLAIVEHLVTLG.ADVNAQEPCNGRTALHLAVDLQNPDLV.SLLLKCGADVNRVTYQG...............................        250
RAT I-κBα         C.LHLASIHGYLGIVEHLVTLG.ADVNAQEPCNGRTALHLAVDLQNPDLV.SLLLKCGADVNRVTYQG...............................        250
PIG I-κBα         C.LHLASIHGYLGIVELLVSLG.ADVNAQEPCNGRTALHLAVDLQNPDLV.SLLLKCGADVNRVTYQG...............................        250

401                         +                         +                         +                        450                         +                         +                         +                        500
NIM1              VEILEQEDKREQIPRDVPPSFAVAADELKMTLLDLFNRVALAQRLFPTEAQAAMETAEMKGICHFIVISLEPDRLIGTKRTSPGVKLAPFRILEEHQSRL        494
MOUSE I-κBα       ..........................................................YSPYQLT..WGRPSTRIQQ....................        267
RAT I-κBα         ..........................................................YSPYQLT..WGRPSTRIQQ....................        267
PIG I-κBα         ..........................................................YSPYQLT..WGRPSTRIQQ....................        267

501                         +                         +                         +                        550                         +                         +                         +                        600
NIM1              KALSKIVELGKRFFPRCSAVLDQIMCEDLTQLACGEDDTAEKRLQKKQRYMEIQETTLKKAFSEDNLELGNSSLTDSTSSTSKSTGKRSNRKLSHRRR        593
MOUSE I-κBα       ...........QLGQ.................LITENLQMLPESEDE......ESYDTESE....FTEDEL.PYDDCVF............GGQR.....LTL...        314
RAT I-κBα         ...........QLGQ.................LITENLQTLPESEDE......ESYDTESE....FTEDEL.PYDDCVF............GGQR.....LTL...        314
PIG I-κBα         ...........QLGQ.................LITENLQMLPESEDE......ESYDTESE....FTEDEL.PYDDCVL............GGQR.....LTL...        314
```

FIGURE 1B

```
NIM1   :  267 VSNVHKALDSDDIELVKLLLKEDHTNLDDACALHFAVAYCN 307
               +   +  +ALD+  DIELVKL++    +   +LDDA A+H+AV +CN
Rice-1 :   33 IRRMRRALDAADIELVKLMVMGEGLDLDDALAVHYAVQHCN 155

NIM1   :  327 PRGYTVLHVAAMRKEPQLILSLLEKGASASEATLEGRT 364
              P G T LH+AA        P ++   LL+   A  +  T +G T
Rice-1 :  215 PTGKTALHLAAEMVSPDMVSVLLDHHADXNFRTXDGVT 328

NIM1   :  267 VSNVHKALDSDDIELVKLLLKEDHTNLDDACALHFAVAYCN 307
               +   +  +ALD+  DIELVKL++    +   +LDDA A+H+AV +CN
Rice-2 :   33 IRRMRRALDAADIELVKLMVMGEGLDLDDALAVHYAVQHCN 155

NIM1   :  325 RNPRGYTVLHVAAMRKEPQLILSLLEK 351
              R  P     T LH+AA        P ++   LL++
Rice-2 :  208 RRPDSKTALHLAAEMVSPDMVSVLLDQ 288

NIM1   :  267 VSNVHKALDSDDIELVKLLLKEDHTNLDDACALHFAVAYCN 307
               +   +  +ALD+  DIELVKL++    +   +LDDA A+H+AV +CN
Rice-3 :   33 IRRMRRALDAADIELVKLMVMGEGLDLDDALAVHYAVQHCN 155

NIM1   :  325 RNPRGYTVLHVAAMRKEPQLILSLLEK 351
              R  P     T LH+AA        P ++   LL++
Rice-3 :  208 RRPDSKTALHLAAEMVSPDMVSVLLDQ 288

NIM1   :  267 VSNVHKALDSDDIELVKLLLKEDHTNLDDACALHFAVAYCN 307
               +   +  +ALD+  DIELVKL++    +   +LDDA A+H+AV +CN
Rice-4 :   33 IRRMRRALDAADIELVKLMVMGEGLDLDDALAVHYAVQHCN 155

NIM1   :  327 PRGYTVLHVAAMRKEPQLI 345
              P G T LH+AA        P ++
Rice-4 :  215 PTGKTALHLAAEMVSPDMV 271
```

FIGURE 2

METHOD FOR PROTECTING PLANTS

This application is a continuation-in-part of U.S. application Ser. No. 08/761,543, filed Dec. 6, 1996, issued as U.S. Pat. No. 5,780,469 on Jul. 14, 1998. This application is also a continuation-in-part of U.S. application Ser. No. 08/875,015, filed Jul. 16, 1997. This application is further a continuation-in-part of International Application No. PCT/EP96/02672 (WO 97/01277), filed Jun. 20, 1996. In addition, this application claims the benefit of U.S. Provisional Application No. 60/034,378, filed Dec. 27, 1996; U.S. Provisional Application No. 60/034,379, filed Dec. 27, 1996; U.S. Provisional Application No. 60/034,382, filed Dec. 27, 1996; U.S. Provisional Application No. 60/034,730, filed Jan. 10, 1997; U.S. Provisional Application No. 60/035,021, filed Jan. 10, 1997; U.S. Provisional Application No. 60/035,022, filed Jan. 10, 1997; and U.S. Provisional Application No. 60/035,024, filed Jan. 10, 1997. The disclosures of all the aforementioned applications are hereby expressly incorporated by reference in their entireties into the instant disclosure.

FIELD OF THE INVENTION

The present invention relates to a method for protecting a plant against pathogen attack through synergistic disease-resistance attained by applying a microbicide to an immunomodulated plant.

BACKGROUND OF THE INVENTION

I. Systemic Acquired Resistance

Plants are constantly challenged by a wide variety of pathogenic organisms including viruses, bacteria, fungi, and nematodes. Crop plants are particularly vulnerable because they are usually grown as genetically-uniform monocultures; when disease strikes, losses can be severe. However, most plants have their own innate mechanisms of defense against pathogenic organisms. Natural variation for resistance to plant pathogens has been identified by plant breeders and pathologists and bred into many crop plants. These natural disease resistance genes often provide high levels of resistance to or immunity against pathogens.

Systemic acquired resistance (SAR) is one component of the complex system plants use to defend themselves from pathogens (Hunt and Ryals, Crit. Rev. in Plant Sci. 15, 583–606 (1996), incorporated by reference herein in its entirety; Ryals et al., Plant Cell 8, 1809–1819 (1996), incorporated by reference herein in its entirety). See also, U.S. Pat. No. 5,614,395, incorporated by reference herein in its entirety. SAR is a particularly important aspect of plant-pathogen responses because it is a pathogen-inducible, systemic resistance against a broad spectrum of infectious agents, including viruses, bacteria, and fungi. When the SAR signal transduction pathway is blocked, plants become more susceptible to pathogens that normally cause disease, and they also become susceptible to some infectious agents that would not normally cause disease (Gaffney et al., Science 261, 754–756 (1993), incorporated by reference herein in its entirety; Delaney et al., Science 266, 1247–1250 (1994), incorporated by reference herein in its entirety; Delaney et al., Proc. Natl. Acad. Sci. USA 92, 6602–6606 (1995), incorporated by reference herein in its entirety; Delaney, Plant Phys. 113, 5–12 (1997), incorporated by reference herein in its entirety; Bi et al., Plant J. 8, 235–245 (1995), incorporated by reference herein in its entirety; Mauch-Mani and Slusarenko, Plant Cell 8, 203–212 (1996), incorporated by reference herein in its entirety). These observations indicate that the SAR signal transduction pathway is critical for maintaining plant health.

Conceptually, the SAR response can be divided into two phases. In the initiation phase, a pathogen infection is recognized, and a signal is released that travels through the phloem to distant tissues. This systemic signal is perceived by target cells, which react by expression of both SAR genes and disease resistance. The maintenance phase of SAR refers to the period of time, from weeks up to the entire life of the plant, during which the plant is in a quasi steady state, and disease resistance is maintained (Ryals et al., 1996).

Salicylic acid (SA) accumulation appears to be required for SAR signal transduction. Plants that cannot accumulate SA due to treatment with specific inhibitors, epigenetic repression of phenylalanine ammonia-lyase, or transgenic expression of salicylate hydroxylase, which specifically degrades SA, also cannot induce either SAR gene expression or disease resistance (Gaffney et al., 1993; Delaney et al., 1994; Mauch-Mani and Slusarenko 1996; Maher et al., Proc. Natl. Acad. Sci. USA 91, 7802–7806 (1994), incorporated by reference herein in its entirety; Pallas et al., Plant J. 10, 281–293 (1996), incorporated by reference herein in its entirety). Although it has been suggested that SA might serve as the systemic signal, this is currently controversial and, to date, all that is known for certain is that if SA cannot accumulate, then SAR signal transduction is blocked (Pallas et al., 1996; Shulaev et al., Plant Cell 7, 1691–1701 (1995), incorporated by reference herein in its entirety; Vernooij et al., Plant Cell 6, 959–965 (1994), incorporated by reference herein in its entirety).

Recently, Arabidopsis has emerged as a model system to study SAR (Uknes et al., Plant Cell 4, 645–656 (1992), incorporated by reference herein in its entirety; Uknes et al., Mol. Plant-Microbe Interact. 6, 692–698 (1993), incorporated by reference herein in its entirety; Cameron et al., Plant J. 5, 715–725 (1994), incorporated by reference herein in its entirety; Mauch-Mani and Slusarenko, Mol. Plant-Microbe Interact. 7, 378–383 (1994), incorporated by reference herein in its entirety; Dempsey and Klessig, Bulletin de L'Institut Pasteur 93, 167–186 (1995), incorporated by reference herein in its entirety). It has been demonstrated that SAR can be activated in Arabidopsis by both pathogens and chemicals, such as SA, 2,6-dichloroisonicotinic acid (INA) and benzo(1,2,3)thiadiazole-7-carbothioic acid S-methyl ester (BTH) (Uknes et al., 1992; Vernooij et al., Mol. Plant-Microbe Interact. 8, 228–234 (1995), incorporated by reference herein in its entirety; Lawton et al., Plant J. 10, 71–82 (1996), incorporated by reference herein in its entirety). Following treatment with either INA or BTH or pathogen infection, at least three pathogenesis-related (PR) protein genes, namely, PR-1, PR-2, and PR-5 are coordinately induced concomitant with the onset of resistance (Uknes et al., 1992, 1993). In tobacco, the best characterized species, treatment with a pathogen or an immunization compound induces the expression of at least nine sets of genes (Ward et al., Plant Cell 3, 1085–1094 (1991), incorporated by reference herein in its entirety). Transgenic disease-resistant plants have been created by transforming plants with various SAR genes (U.S. Pat. No. 5,614,395).

A number of Arabidopsis mutants have been isolated that have modified SAR signal transduction (Delaney, 1997) The first of these mutants are the so-called lsd (lesions simulating disease) mutants and acd2 (accelerated cell death) (Dietrich et al., Cell 77, 565–577 (1994), incorporated by reference herein in its entirety; Greenberg et al., Cell 77, 551–563 (1994), incorporated by reference herein in its entirety).

These mutants all have some degree of spontaneous necrotic lesion formation on their leaves, elevated levels of SA, mRNA accumulation for the SAR genes, and significantly enhanced disease resistance. At least seven different lsd mutants have been isolated and characterized (Dietrich et al., 1994; Weymann et al., *Plant Cell* 7, 2013–2022 (1995), incorporated by reference herein in its entirety). Another interesting class of mutants are cim (constitutive immunity) mutants (Lawton et al., "The molecular biology of systemic acquired resistance" in *Mechanisms of Defence Responses in Plants*, B. Fritig and M. Legrand, eds (Dordrecht, The Netherlands: Kluwer Academic Publishers), pp. 422–432 (1993), incorporated by reference herein in its entirety). See also, U.S. Pat. No. 5,792,904 and International PCT Application WO 94/16077, both of which are incorporated by reference herein in their entireties. Like lsd mutants and acd2, cim mutants have elevated SA and SAR gene expression and resistance, but in contrast to lsd or acd2, do not display detectable lesions on their leaves. cpr1 (constitutive expresser of PR genes) may be a type of cim mutant; however, because the presence of microscopic lesions on the leaves of cpr1 has not been ruled out, cpr1 might be a type of lsd mutant (Bowling et al., *Plant Cell* 6, 1845–1857 (1994), incorporated by reference herein in its entirety).

Mutants have also been isolated that are blocked in SAR signaling. ndr1 (non-race-specific disease resistance) is a mutant that allows growth of both *Pseudomonas syringae* containing various avirulence genes and also normally avirulent isolates of *Peronospora parasitica* (Century et al., *Proc. Natl. Acad.Sci. USA* 92, 6597–6601(1995), incorporated by reference herein in its entirety). Apparently this mutant is blocked early in SAR signaling. npr1 (nonexpresser of PR genes) is a mutant that cannot induce expression of the SAR signaling pathway following INA treatment (Cao et al., *Plant Cell* 6, 1583–1592 (1994), incorporated by reference herein in its entirety). eds (enhanced disease susceptibility) mutants have been isolated based on their ability to support bacterial infection following inoculation of a low bacterial concentration (Glazebrook et al., *Genetics* 143, 973–982 (1996), incorporated by reference herein in its entirety; Parker et al., *Plant Cell* 8, 2033–2046 (1996), incorporated by reference herein in its entirety). Certain eds mutants are phenotypically very similar to npr1, and, recently, eds5 and eds53 have been shown to be allelic to npr1 (Glazebrook et al., 1996). nim1 (noninducible immunity) is a mutant that supports *P. parasitica* (i.e., causal agent of downy mildew disease) growth following INA treatment (Delaney et al., 1995; U.S. Pat. No. 5,792,904). Although nim1 can accumulate SA following pathogen infection, it cannot induce SAR gene expression or disease resistance, suggesting that the mutation blocks the pathway downstream of SA. nim1 is also impaired in its ability to respond to INA or BTH, suggesting that the block exists downstream of the action of these chemicals (Delaney et al., 1995; Lawton et al., 1996).

Recently, two allelic Arabidopsis genes have been isolated and characterized, mutants of which are responsible for the nim1 and npr1 phenotypes, respectively (Ryals et al., *Plant Cell* 9, 425–439 (1997), incorporated by reference herein in its entirety; Cao et al., *Cell* 88, 57–63 (1997), incorporated by reference herein in its entirety). The wild-type NIM1 gene product is involved in the signal transduction cascade leading to both SAR and gene-for-gene disease resistance in Arabidopsis (Ryals et al., 1997). Ryals et al., 1997 also report the isolation of five additional alleles of nim1 that show a range of phenotypes from weakly impaired in chemically induced PR- 1 gene expression and fungal resistance to very strongly blocked. Transformation of the wild-type NPR1 gene into npr1 mutants not only complemented the mutations, restoring the responsiveness of SAR induction with respect to PR-gene expression and disease resistance, but also rendered the transgenic plants more resistant to infection by *P. syringae* in the absence of SAR induction (Cao et al., 1997).

II. NF-κB/IκB Signal Transduction Pathways

NF-κB/IκB signaling pathways have been implicated in disease resistance responses in a range of organisms from Drosophila to mammals. In mammals, NF-κB/IκB signal transduction can be induced by a number of different stimuli including exposure of cells to lipopolysaccharide, tumor necrosis factor, interleukin 1 (IL-1), or virus infection (Baeuerle and Baltimore, *Cell* 87, 13–20 (1996); Baldwin, *Annu. Rev. Immunol.* 14, 649–681 (1996)). The activated pathway leads to the synthesis of a number of factors involved in inflammation and immune responses, such as IL-2, IL-6, IL-8 and granulocyte/macrophage-colony stimulating factor (deMartin et al., *Gene* 152, 253–255 (1995)). In transgenic mouse studies, the knock-out of NF-κB/IκB signal transduction leads to a defective immune response including enhanced susceptibility to bacterial and viral pathogens (Beg and Baltimore, *Science* 274, 782–784 (1996); Van Antwerp et al., *Science* 274, 787–789 (1996); Wang et al., *Science* 274, 784–787 (1996); Baeuerle and Baltimore (1996)). In Arabidopsis, SAR is functionally analogous to inflammation in that normal resistance processes are potentiated following SAR activation leading to enhanced disease resistance (Bi et al., 1995; Cao et al., 1994; Delaney et al., 1995; Delaney et al., 1994; Gaffney et al., 1993; Mauch-Mani and Slusarenko 1996; Delaney, 1997). Furthermore, inactivation of the pathway leads to enhanced susceptibility to bacterial, viral and fungal pathogens. Interestingly, SA has been reported to block NF-κB activation in mammalian cells (Kopp and Ghosh, *Science* 265, 956–959 (1994)), while SA activates signal transduction in Arabidopsis. Bacterial infection of Drosophila activates a signal transduction cascade leading to the synthesis of a number of antifungal proteins such as cercropin B, defensin, diptericin and drosomycin (Ip et al., *Cell* 75, 753–763 (1993); Lemaitre et al., *Cell* 86, 973–983 (1996)). This induction is dependent on the gene product of dorsal and dif, two NF-κB homologs, and is repressed by cactus, an IκB homolog, in the fly. Mutants that have decreased synthesis of the antifungal and antibacterial proteins have dramatically lowered resistance to infection.

Despite much research and the use of sophisticated and intensive crop protection measures, including genetic transformation of plants, losses due to disease remain in the billions of dollars annually. Therefore, there is a continuing need to develop new crop protection measures based on the ever-increasing understanding of the genetic basis for disease resistance in plants.

SUMMARY OF THE INVENTION

In view of the above, a preferred aspect of the present invention pertains to a novel method of protecting plants from pathogen attack through synergistic disease resistance attained by applying a microbicide to immunomodulated plants. Immunomodulated plants are those in which SAR is activated, typically exhibiting greater-than-wild-type SAR gene expression, and are therefore referred to as "SAR-on" plants. Immunomodulated plants for use in the method of the invention may be obtained in at least three different ways: by applying to plants a chemical inducer of SAR such as BTH, INA, or SA; through a selective breeding program in which plants are selected based on constitutive expression of SAR genes and/or a disease-resistant phenotype; or by genetically engineering plants by transforming them with one or more SAR genes such as a functional form of the NIM1 gene. The microbicide applied to the immunomodulated plants may be either a conventional microbicide such as the fungicide metalaxyl (ridomil) or, if applied to immunomodulated plants obtained through selective breeding or genetic engineering, the microbicide may be a chemical inducer of SAR such as BTH, INA, or SA.

Immunomodulation provides a certain level of disease resistance in a plant. Similarly, application of a microbicide to a plant provides a certain level of disease resistance. The expected result of combining immunomodulation with microbicide application would be a level of control reflecting the additive levels of control provided by the individual methods of providing disease resistance. However, by concurrently applying a microbicide to an immunomodulated plant, the disease resistance is unexpectedly synergistically enhanced; i.e., the level of disease resistance is greater than the expected additive levels of disease resistance.

Accordingly, the present invention concerns the cultivation of immunomodulated plants and the application of a suitable amount of a conventional microbicide thereto. Especially preferred embodiments of the invention concern plants genetically engineered to contain and express a functional form of the NIM1 gene or a homologue or variant thereof.

Thus, the present invention provides a method for protecting a plant from pathogen attack, comprising the steps of providing an immunomodulated plant having a first level of disease resistance; and applying to the immunomodulated plant at least one microbicide that confers a second level of disease resistance; whereby application of the microbicide to the immunomodulated plant confers a synergistically enhanced third level of disease resistance that is greater than the sum of the first and second levels of disease resistance.

In one embodiment, the immunomodulated plant is a constitutive immunity (cim) mutant plant. In a preferred form of this embodiment, the cim mutant plant is selected from a population of plants according to the following steps: evaluating the expression of SAR genes in uninfected plants that are phenotypically normal in that the uninfected plants lack a lesion mimic phenotype; and selecting uninfected plants that constitutively express SAR genes in the absence of viral, bacterial, or fungal infection.

In another embodiment, the immunomodulated plant is a lesion mimic mutant plant. In a preferred form of this embodiment, the lesion mimic mutant plant is selected from a population of plants according to the following steps: evaluating the expression of SAR genes in uninfected plants that have a lesion mimic phenotype; and selecting uninfected plants that constitutively express SAR genes in the absence of viral, bacterial, or fungal infection.

In yet another embodiment, the immunomodulated plant is obtained by recombinant expression in a plant of an SAR gene. In a preferred form of this embodiment, the SAR gene comprises a DNA molecule that encodes a NIM 1 protein involved in the signal transduction cascade leading to systemic acquired resistance in plants. In one example, the NIM1 protein comprises the amino acid sequence set forth in SEQ ID NO:2. In another example, the DNA molecule hybridizes under the following conditions to the coding sequence set forth in SEQ ID NO:1: hybridization in 1% BSA; 520 mM $NaPO_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In still another example, the DNA molecule comprises the coding sequence set forth in SEQ ID NO:1. In yet another example, the DNA molecule hybridizes under the following conditions to a DNA molecule that encodes a NIM1 protein comprising the amino acid sequence set forth in SEQ ID NO:2: hybridization in 1% BSA; 520 mM $NaPO_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C.

In a further embodiment, the SAR gene encodes an altered form of a NIM1 protein that acts as a dominant-negative regulator of the SAR signal transduction pathway. In one preferred form of this embodiment, the altered form of the NIM1 protein has alanines instead of serines in amino acid positions corresponding to positions 55 and 59 of SEQ ID NO:2. In one example, the altered form of the NIM1 protein comprises the amino acid sequence shown in SEQ ID NO:8. In another example, the DNA molecule comprises the nucleotide sequence shown in SEQ ID NO:7. In still another example, the DNA molecule hybridizes under the following conditions to the nucleotide sequence set forth in SEQ ID NO:7: hybridization in 1% BSA; 520 mM $NaPO_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In another preferred form of this embodiment, the altered form of the NIM1 protein has an N-terminal truncation of amino acids corresponding approximately to amino acid positions 1–125 of SEQ ID NO:2. In one example, the altered form of the NIM1 protein comprises the amino acid sequence shown in SEQ ID NO:10. In another example, the DNA molecule comprises the nucleotide sequence shown in SEQ ID NO:9. In still another example, the DNA molecule hybridizes under the following conditions to the nucleotide sequence set forth in SEQ ID NO:9: hybridization in 1% BSA; 520 mM $NaPO_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In yet another preferred form of this embodiment, the altered form of the NIM1 protein has a C-terminal truncation of amino acids corresponding approximately to amino acid positions 522–593 of SEQ ID NO:2. In one example, the altered form of the NIM1 protein comprises the amino acid sequence shown in SEQ ID NO:12. In another example, the DNA molecule comprises the nucleotide sequence shown in SEQ ID NO:11. In still another example, the DNA molecule hybridizes under the following conditions to the nucleotide sequence set forth in SEQ ID NO:11: hybridization in 1% BSA; 520 mM $NaPO_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In still another preferred form of this embodiment, the altered form of the NIM1 protein has an N-terminal truncation of amino acids corresponding approximately to amino acid positions 1–125 of SEQ ID NO:2 and a C-terminal truncation of amino acids corresponding approximately to amino acid positions 522–593 of SEQ ID NO:2. In one example, the altered form of the NIM1 protein comprises the amino acid sequence shown in SEQ ID NO:14. In another example, the DNA molecule comprises the nucleotide sequence shown in SEQ ID NO:13. In still another example, the DNA molecule hybridizes under the following conditions to the nucleotide sequence set forth in SEQ ID NO:13: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C. In an additionally preferred form of this embodiment, the altered form of the NIM1 protein consists essentially of ankyrin motifs corresponding approximately to amino acid positions 103–362 of SEQ ID NO:2. In one example, the altered form of the NIM1 protein comprises the amino acid sequence shown in SEQ ID NO:16. In another example, the DNA molecule comprises the nucleotide sequence shown in SEQ ID NO:15. In still another example, the DNA molecule hybridizes under the following conditions to the nucleotide sequence set forth in SEQ ID NO:15: hybridization in 1% BSA; 520 mM NaPO$_4$, pH7.2; 7% lauryl sulfate, sodium salt; 1 mM EDTA; 250 mM sodium chloride at 55° C. for 18–24 h, and wash in 6×SSC for 15 min. (X3) 3×SSC for 15 min. (X1) at 55° C.

In an additional embodiment, the step of providing an immunomodulated plant comprises applying a chemical inducer of systemic acquired resistance to the plant. In one preferred form of this embodiment, the chemical inducer of systemic acquired resistance is a benzothiadiazole. In one example, the benzothiadiazole is benzo(1,2,3)thiadiazole-7-carbothioic acid S-methyl ester. In another preferred form of this embodiment, the chemical inducer of systemic acquired resistance is an isonicotinic acid compound. In still another preferred form of this embodiment, the chemical inducer of systemic acquired resistance is a salicylic acid compound.

In one preferred embodiment of the method of the invention, the microbicide is a fungicide selected from the following group: 4-[3-(4-chlorophenyl)-3-(3,4-dimethoxyphenyl)acryloyl]morpholine ("dimethomorph"); 5-methyl-1,2,4-triazolo[3,4-b][1,3]benzothiazole ("tricyclazole"); 3-allyloxy-1,2-benzothiazole-1,1-dioxide ("probonazole"); $\mu$-[2-(4-chlorophenyl)ethyl]--$\mu$-(1,1-dimethylethyl)-1H-1,2,4-triazole-1-ethanol, ("tebuconazol"); 1-[[3-(2-chlorophenyl)-2--(4-fluorophenyl)oxiran-2-yl]methyl]-1H-1,2,4-triazole, ("epoxyconazol"); $\mu$-(4-chlorophenyl)--$\mu$-(1-cyclopropylethyl)--1H-1,2,4-triazole--1-ethanol, ("cyproconazol"); 5-(4-chlorobenzyl)--2,2-dimethyl-1--(1H-2,4-triazol-1--ylmethyl)-cyclopentanol, ("metconazol"); 2-(2,4-dichlorophenyl)--3-(1H-1,2,4-triazol-1-yl)-propyl--1,1,2,2-tetrafluoroethyl-ether, ("tetraconazol"); methyl-(E)-2-{2-[6-(2-cyanophenoxy)pyrimidin--4-yloxy]phenyl}--3-methoxyacrylate, ("ICI A 5504", "azoxystrobin"); methyl-(E)--2-methoximino--2-$\mu$-(o-tolyloxy)--o-tolyl]acetate, ("BAS 490 F", "cresoxime methyl"); 2-(2-phenoxyphenyl)-(E)-2-methoximino--N-methylacetamide); [2-(2,5-dimethylphenoxymethyl)-phenyl]-(E)--2-methoximino-N-methylacetamide); (1R,3S/1S,3R)-2,2-dichloro--N-[(R)-1-(4-chlorophenyl)ethyl]--1-ethyl-3-methylcyclopropanecarboxamide, ("KTU 3616"); manganese thylenebis(dithiocarbamate)polymer-zinc complex, ("mancozeb"); 1-[2-(2,4-dichlorophenyl)-4-propyl-1,3-dioxolan--2-ylmethyl]--1H-1,2,4--triazole, ("propiconazole"); 1-{2-[2-chloro-4-(4-chlorophenoxy)phenyl]-4-methyl--1,3-dioxolan--2-ylmethy 1)--1H-1,2,4--triazole, ("difenoconazole"); 1-[2-(2,4-dichlorophenyl)pentyl--1H-1,2,4-triazole, ("penconazole"); cis-4-[3-(4-tert-butylphenyl)--2-methylpropyl]--2,6-dimethethymorpholine, ("fenpropimorph"); 1-[3-(4-tert-butylphenyl)--2-methylpropyl]-piperidine, ("fenpropidin"); 4-cyclopropyl-6-methyl-N-phenyl-2-pyrimidinamine ("cyprodinil"); (RS)-N-(2,6-dimethylphenyl--N-(methoxyacetyl)-alanine methyl ester ("metalaxyl", "ridomil"); (R)-N-(2,6-dimethylphenyl--N-(methoxyacetyl)-alanine methyl ester ("R-metalaxyl"); 1,2,5,6-tetrahydro--4H-pyrrolo[3,2,1-ij]quinolin-4-one ("pyroquilon"); and ethyl hydrogen phosphonate ("fosetyl"). Especially preferred fungicides are metalaxyl and fosetyl.

In another preferred embodiment of the method of the invention, the microbicide is either a benzothiadiazole compound, an isonicotinic acid compound, or a salicylic acid compound. In one such example, the benzothiadiazole compound is benzo(1,2,3)thiadiazole-7-carbothioic acid S-methyl ester.

In still another preferred embodiment of the method of the invention, two microbicides are concurrently applied to the immunomodulated plant. In an exemplary form of this embodiment, one of the microbicides is a fungicide selected from the following group: 4-[3-(4-chlorophenyl)-3-(3,4-dimethoxyphenyl)acryloyl]morpholine ("dimethomorph"); 5-methyl-1,2,4-triazolo[3,4-b][1,3]benzothiazole ("tricyclazole"); 3-allyloxy-1,2-benzothiazole-1,1dioxide ("probonazole"); $\mu$-[2-(4-chlorophenyl)ethyl]--$\mu$-(1,1-dimethylethyl)-1H-1,2,4-triazole-1-ethanol, ("tebuconazol"); 1-[[3-(2-chlorophenyl)-2--(4-fluorophenyl)oxiran-2-yl ]methyl]-1H-1,2,4-triazole, ("epoxyconazol"); $\mu$-(4-chlorophenyl)--$\mu$-(1-cyclopropylethyl)--1H-1,2,4-triazole--1-ethanol, ("cyproconazol"); 5-(4-chlorobenzyl)--2,2-dimethyl-1--(1H-2,4-triazol-1--ylmethyl)-cyclopentanol, ("metconazol"); 2-(2,4-dichlorophenyl)--3-(1H-1,2,4-triazol-1-yl)-propyl--1,1,2,2-tetrafluoroethyl-ether, ("tetraconazol"); methyl-(E)-2-{2-[6-(2-cyanophenoxy)pyrimidin--4-yloxy]phenyl}--3-methoxyacrylate, ("ICI A 5504", "azoxystrobin"); methyl-(E)--2-methoximino--2-$\mu$-(o-tolyloxy)--o-tolyl]acetate, ("BAS 490 F", "cresoxime methyl"); 2-(2-phenoxyphenyl)-(E)-2-methoximino--N-methylacetamide); [2-(2,5-dimethylphenoxymethyl)-phenyl]-(E)--2-methoximino-N-methylacetamide); (1R,3S/1S,3R)-2,2-dichloro--N-[(R)-1-(4-chlorophenyl)ethyl]--1-ethyl-3-methylcyclopropanecarboxamide, ("KTU 3616"); manganese ethylenebis(dithiocarbamate)polymer-zinc complex, ("mancozeb"); 1-[2-(2,4-dichlorophenyl)-4-propyl-1,3-dioxolan--2-ylmethyl]--1H-1,2,4--triazole, ("propiconazole"); 1-{2-[2-chloro-4-(4-chlorophenoxy)phenyl]-4-methyl--1,3-dioxolan--2-ylmethy 1)--1H-1,2,4--triazole, ("difenoconazole"); 1-[2-(2,4-dichlorophenyl)pentyl--1H-1,2,4-triazole, ("penconazole"); cis-4-[3-(4-tert-butylphenyl)--2-methylpropyl]--2,6-dimethylmorpholine, ("fenpropimorph"); 1-[3-(4-tert-butylphenyl)--2-methylpropyl]-piperidine, ("fenpropidin"); 4-cyclopropyl-6-methyl-N-phenyl-2-pyrimidinamine ("cyprodinil"); (RS)-N-(2,6-dimethylphenyl--N-(methoxyacetyl)-alanine methyl ester ("metalaxyl", "ridomil"); (R)-N-(2,6-dimethylphenyl--N-(methoxyacetyl)-alanine methyl ester ("R-metalaxyl"); 1,2,5,6-tetrahydro--4H-pyrrolo[3,2,1-ij]quinolin-4-one ("pyroquilon"); and ethyl hydrogen phosphonate ("fosetyl") and the other microbicide is either a benzothiadiazole compound, an isonicotinic acid compound, or a salicylic acid compound. In one such example, the fungicide is metalaxyl and the other microbicide is a benzothiadiazole compound.

BRIEF DESCRIPTION OF THE DRAWINGS

FIGS. 1A and 1B are sequence alignment of the NIM1 protein sequence with IκBα from mouse, rat, and pig. Vertical bars (|) above the sequences indicate amino acid identity between NIM1 and the IκBα sequences (matrix score equals 1.5); double dots (:) above the sequences indicate a similarity score >0.5; single dots (.) above the sequences indicate a similarity score <0.5 but >0.0; and a score <0.0 indicates no similarity and has no indicia above the sequences (see Examples). Locations of the mammalian IκBα ankyrin domains were identified according to de Martin et al., Gene 152, 253–255 (1995). The dots within a sequence indicate gaps between NIM1 and IκBα proteins. The five ankyrin repeats in IκBα are indicated by the dashed lines under the sequence. Amino acids are numbered relative to the NIM1 protein with gaps introduced where appropriate. Plus signs (+) are placed above the sequences every 10 amino acids.

FIG. 2 is an amino acid sequence comparison of regions of the NIM1 protein (numbers correspond to amino acid positions in SEQ ID NO:2) and rice EST protein products (SEQ ID NOs: 17–24).

BRIEF DESCRIPTION OF THE SEQUENCES IN THE SEQUENCE LISTING

Figure 3:
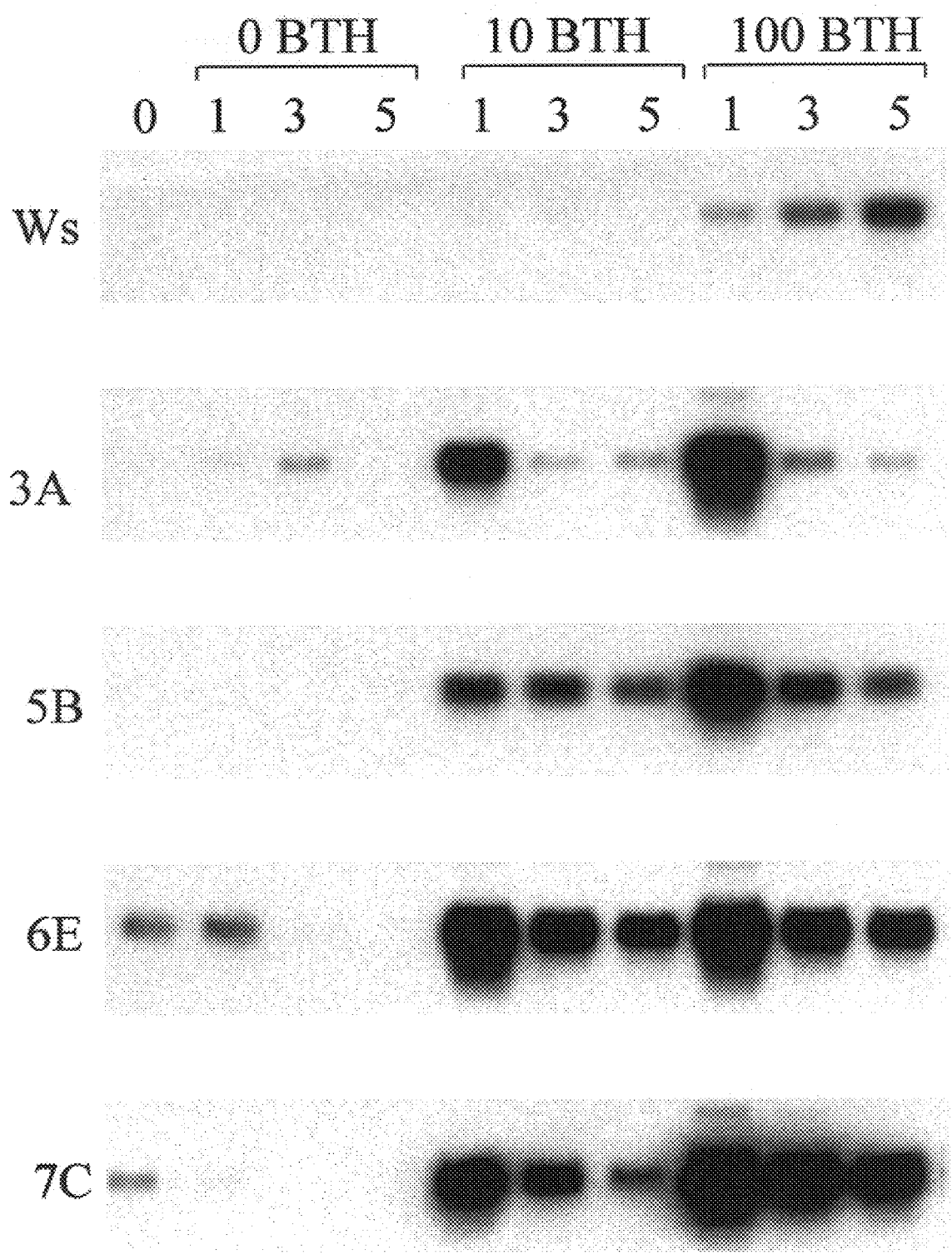
FIG. 3 presents the results of Northern analysis showing the time course of PR-1 gene expression in wild-type and NIM1-overexpressing lines following treatment with water or BTH. RNA was prepared from treated plants and analyzed as described in the Examples. "Ws" is the wild-type Arabidopsis thaliana Ws ecotype. "3A", "5B", "6E", and "7C" are individual NIM1-overexpressing plant lines produced according to Example 21. "0 BTH" is water treatment; "10 BTH" is 10 μM BTH treatment; "100 BTH" is 100 μM BTH treatment. "0" is day zero control samples; "1", "3", and "5" are samples at days 1, 3, and 5.

SEQ ID NO:1 is a 5655-bp genomic sequence comprising the coding region of the wild-type Arabidopsis thaliana NIM1 gene.

SEQ ID NO:2 is the amino acid sequence of the wild-type Arabidopsis thaliana NIM1 protein encoded by the coding region of SEQ ID NO:1.

SEQ ID NO:3 is the mouse IκBα amino acid sequence from FIGS. 1A and 1B.

SEQ ID NO:4 is the rat IκBα amino acid sequence from FIGS. 1A and 1B.

SEQ ID NO:5 is the pig IκBα amino acid sequence from FIGS. 1A and 1B.

SEQ ID NO:6 is the cDNA sequence of the Arabidopsis thaliana NIM1 gene.

SEQ ID NO's:7 and 8 are the DNA coding sequence and encoded amino acid sequence, respectively, of a dominant-negative form of the NIM1 protein having alanine residues instead of serine residues at amino acid positions 55 and 59.

SEQ ID NO's:9 and 10 are the DNA coding sequence and encoded amino acid sequence, respectively, of a dominant-negative form of the NIM1 protein having an N-terminal deletion.

SEQ ID NO's: 11 and 12 are the DNA coding sequence and encoded amino acid sequence, respectively, of a dominant-negative form of the NIM1 protein having a C-terminal deletion.

SEQ ID NO's:13 and 14 are the DNA coding sequence and encoded amino acid sequence, respectively, of an altered form of the NIM1 gene having both N-terminal and C-terminal amino acid deletions.

SEQ ID NO's: 15 and 16 are the DNA coding sequence and encoded amino acid sequence, respectively, of the ankyrin domain of NIM1.

SEQ ID NO:17 is the Rice-1 AA sequence 33–155 from FIG. 2.

SEQ ID NO:18 is the Rice-1 AA sequence 215–328 from FIG. 2.

SEQ ID NO:19 is the Rice-2 AA sequence 33–155 from FIG. 2.

SEQ ID NO:20 is the Rice-2 AA sequence 208–288 from FIG. 2.

SEQ ID NO:21 is the Rice-3 AA sequence 33–155 from FIG. 2.

SEQ ID NO:22 is the Rice-3 AA sequence 208–288 from FIG. 2.

SEQ ID NO:23 is the Rice-4 AA sequence 33–155 from FIG. 2.

SEQ ID NO:24 is the Rice-4 AA sequence 215–271 from FIG. 2.

SEQ ID NOs:25 through 32 are oligonucleotide primers.

Definitions acd: accelerated cell death mutant plant
AFLP: Amplified Fragment Length Polymorphism
avrRpt2: avirulence gene Rpt2, isolated from Pseudomonas syringae
BAC: Bacterial Artificial Chromosome
BTH: benzo(1,2,3)thiadiazole-7-carbothioic acid S-methyl ester
CIM: Constitutive IMmunity phenotype (SAR is constitutively activated)
cim: constitutive immunity mutant plant
cM: centimorgans
cpr1: constitutive expresser of PR genes mutant plant
Col-O: Arabidopsis ecotype Columbia
ECs: Enzyme combinations
Emwa: Peronospora parasitica isolate compatible in the Ws-O ecotype of Arabidopsis
EMS: ethyl methane sulfonate
INA: 2,6-dichloroisonicotinic acid
Ler: Arabidopsis ecotype Landsberg erecta
lsd: lesions simulating disease mutant plant
nahG: salicylate hydroxylase Pseudomonas putida that converts salicylic acid to catechol
NahG: Arabidopsis line transformed with nahG gene
ndr: non-race-specific disease resistance mutant plant
nim: non-inducible immunity mutant plant
NIM1: the wild type gene, involved in the SAR signal transduction cascade
NIM1: Protein encoded by the wild type NIM1 gene
nim1: mutant allele of NIM1, conferring disease susceptibility to the plant; also refers to mutant Arabidopsis thaliana plants having the nim1 mutant allele of NIM1
Noco: Peronospora parasitica isolate compatible in the Col-O ecotype of Arabidopsis
ORF: open reading frame
PCs: Primer combinations
PR: Pathogenesis Related
SA: salicylic acid
SAR: Systemic Acquired Resistance
SAR-on: Immunomodulated plants in which SAR is activated, typically exhibiting greater-than-wild-type SAR gene expression and having a disease resistant phenotype
SSLP: Simple Sequence Length Polymorphism
UDS: Universal Disease Susceptible phenotype
Wela: Peronospora parasitica isolate compatible in the Weiningen ecotype of Arabidopsis
Ws-O: Arabidopsis ecotype Issilewskija
WT: wild type
YAC: Yeast Artificial Chromosome

DETAILED DESCRIPTION OF THE INVENTION

The present invention provides a novel method of protecting plants from pathogen attack through synergistic disease resistance attained by applying a microbicide to immunomodulated plants. Immunomodulated plants are those in which SAR is activated and are therefore referred to as "SAR-on" plants. Immunomodulated plants for use in the method of the invention predictably exhibit greater-than-wild-type SAR gene expression and have a disease-resistant phenotype. Such plants may be obtained in at least three different ways: by applying to plants a chemical inducer of SAR such as BTH, INA, or SA; through a selective breeding program in which plants are selected based on constitutive expression of SAR genes and/or a disease-resistant phenotype; or by genetically engineering plants by transforming them with one or more SAR genes such as a functional form of the NIM1 gene. The microbicide applied to the immunomodulated plants may be either a conventional microbicide such as the fungicide metalaxyl (ridomil) or, if applied to immunomodulated plants obtained through selective breeding or genetic engineering, the microbicide may be a chemical inducer of SAR such as BTH, INA, or SA.

The method of the invention results in greater pathogen control than is achieved through either immunomodulation or microbicide application alone. Immunomodulation provides a certain level of disease resistance in a plant. Similarly, application of a microbicide to a plant provides a certain level of disease resistance. The expected result of combining immunomodulation with microbicide application would be a level of control reflecting the additive levels of control provided by the individual methods of providing disease resistance. However, by concurrently applying a microbicide to an immunomodulated plant, the control of pathogenic disease is unexpectedly synergistically enhanced; i.e., the level of disease control is greater than the expected additive levels of disease resistance.

In addition to greater disease resistance, another advantage of the present invention is that less microbicide is required to achieve the level of disease resistance provided by the method of the invention than is required for use with ordinary, wild-type plants. The result of this is both lower economic costs of microbicide, as well as less chance of adverse environmental consequences resulting from toxicity of some microbicides. Furthermore, the inventive method of protecting plants by combining the effects of immunomodulation and application of a microbicide results in a longer duration of antipathogenic action and altogether higher crop yields. Another advantage of this method is that because the two combined modes of action of pathogen control are completely different from one another, the threat of resistance developing is effectively prevented.

Examples of target crops for the areas of indication disclosed herein comprise, without limitation, the following species of plants: cereals (maize, wheat, barley, rye, oats, rice, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumber, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as tobacco, nuts, coffee, sugar cane, tea, vines, hops, bananas and natural rubber plants, as well as ornamentals (flowers, shrubs, broad-leaved trees and evergreens, such as conifers). This list does not represent any limitation.

The method of the present invention can be used to confer resistance to a wide array of plant pathogens, which include, but are not limited to the following: viruses or viroids such as tobacco or cucumber mosaic virus, ringspot virus or necrosis virus, pelargonium leaf curl virus, red clover mottle virus, tomato bushy stunt virus, and like viruses; Ascomycete fungi such as of the genera Venturia, Podosphaera, Erysiphe, Monolinia, Mycosphaerella, and Uncinula; Basidiomycete fungi such as from the genera Hemileia, Rhizoctonia, and Puccinia; Fungi imperfecti such as the genera Botrytis, Helminthosporium, Rhynchosporium, Fusarium (i.e., *F. monoliforme*), Septoria, Cercospora, Alternaria, Pyricularia, and Pseudocercosporella (i.e., *P. herpotrichoides*); Oomycete fungi such as from the genera Phytophthora (i.e., *P. parasitica*), Peronospora (i.e, *P. tabacina*), Bremia, Pythium, and Plasmopara; as well as other fungi such as *Scleropthora macrospora, Sclerophthora rayissiae, Sclerospora graminicola, Peronosclerospora sorghi, Peronosclerospora philippinensis, Peronosclerospora sacchari* and *Peronosclerospora maydis, Physopella zeae, Cercospora zeae-maydis, Colletotrichum graminicola, Gibberella zeae, Exserohilum turcicum, Kabatiellu zeae*, and *Bipolaris maydis*; bacteria such as *Pseudomonas syringae, Pseudomonas tabaci*, and *Erwinia stewartii*; insects such as aphids, e.g. *Myzus persicae*; and lepidoptera such as Heliothus spp.; and nematodes such as *Meloidogyne incognita.*

I. Obtaining Immunomodulated Plants

All three of the following general routes for obtaining immunomodulated plants are related in that they all fit into the SAR signal transduction pathway model set forth in Ryals et al., (1996). Upon activating the SAR signal transduction pathway to achieve disease resistance, the same set of SAR genes is turned "on" and disease resistance results, regardless of which of the three below-described routes is taken. The differences among these three routes pertain only to which point in the pathway SAR is turned on; the end result is same among these three routes. Therefore, analyses and results observed with regard to immunomodulated plants attained through one route may be extrapolated and applied to immunomodulated plants attained through a different route.

A. Application of a Chemical Inducer of Systemic Acquired Resistance

A first route for obtaining immunomodulated plants involves applying to a plant a chemical capable of inducing SAR. Particularly potent chemical inducers of SAR are benzothiadiazoles such as benzo(1,2,3)thiadiazole-7-carbothioic acid S-methyl ester (BTH). Derivatives of benzothiadiazoles that may further be used as regulators are described in U.S. Pat. Nos. 5,523,311 and 5,614,395, both of which are incorporated herein by reference. BTH-induced SAR, which supplies protection in the field against a broad spectrum of diseases in a variety of crops is described in detail in Friedrich et al., *Plant Journal* 10(1), 61–70 (1996); Lawton et al., *Plant Journal* 10(1), 71–82 (1996); and Gorlach et al., *Plant Cell* 8, 629–643 (1996), each of which is incorporated herein by reference. Other chemical inducers of SAR that may be used to obtain an immunomodulated plant for use in the method of the invention include isonicotinic acid compounds such as 2,6-dichloroisonicotinic acid (INA) and the lower alkyl esters thereof, as well as salicylic acid compounds (SA). Examples of suitable INA and SA compounds are described in U.S. Pat. No. 5,614,395.

B. Breeding Constitutive Immunity (CIM) Mutant Plants

A second route for obtaining immunomodulated plants is through a selective breeding program based on constitutive expression of SAR genes and/or a disease-resistant phenotype. Considerable data shows a tight correlation between the expression of SAR genes and systemic acquired resistance itself (Ward et al. (1991); Uknes et al. (1992); Uknes et al. (1993); Lawton, et al. (1993); and Alexander et al. (1993) *PNAS USA* 90, 7327–7331, herein incorporated by reference. In Arabidopsis, examples of well characterized SAR genes are PR-1, PR-2 and PR-5, with PR-1 expressed at the highest level with the lowest background.

To identify and select plants that constitutively express SAR genes, Northern analysis is performed to detect expression of SAR genes. Known SAR DNA sequences can be utilized in cross-hybridization experiments as described in Uknes et al. (1992). Methods for the hybridization and cloning of nucleic acid sequences are well known in the art. (See, for example, Molecular Cloning, A Laboratory Manual, 2nd Edition, Vol. 1–3, Sambrook et al. (eds.) Cold Spring Harbor Laboratory Press (1989) and the references cited therein).

At least two classes of SAR signal transduction mutants that constitutively express SAR genes have been isolated. One class has been designated as "lsd" mutants (lsd=lesion simulating disease), which are also referred to as "cim Class I" mutants. See, U.S. Pat. No. 5,792,904 and WO 94/16077. lsd (cim Class I) mutants form spontaneous lesions on the leaves, accumulated elevated concentrations of SA, high levels of PR-1, PR-2 and PR-5 mRNA, and are resistant to fungal and bacterial pathogens (Dietrich et al., 1994; Weymann et al., 1995). A second class has been designated as "cim" (cim=constitutive immunity) mutants, which are also referred to as "cim Class II" mutants. See, U.S. Pat. No. 5,792,904 and WO 94/16077. cim mutants have all the characteristics of lsd mutants except spontaneous lesions. That is, cim mutants are visibly phenotypically normal.

Once plants that constitutively express SAR genes are selected, they can be utilized in breeding programs to incorporate constitutive expression of the SAR genes and resistance to pathogens into plant lines. Progeny for further crossing are selected based on expression of the SAR genes and disease resistance as well as for other characteristics important for production and quality according to methods well known to those skilled in the art of plant breeding. For example, because lsd mutants display display lesion formation and necrosis, cim mutants with their normal phenotypes are preferable for use in such breeding programs and in the method of the present invention, although lsd mutants could be used if desired.

C. Transforming Plants with SAR Genes

A third route for obtaining immunomodulated plants is by transforming plants with an SAR gene, preferably a functional form of the NIM1 gene.

1. Recombinant Expression of the Wild-Type NIM1 Gene

Recombinant overexpression of the wild-type form of NIM1 (SEQ ID NO:1) gives rise to transgenic plants with a disease resistant phenotype. See, co-pending U.S. patent application Ser. No. 08/880,179, incorporated herein by reference. Increased levels of the active NIM1 protein produce the same disease-resistance effect as chemical induction with inducing chemicals such as BTH, INA, and SA. Preferably, the expression of the NIM1 gene is at a level that is at least two-fold above the expression level of the NIM1 gene in wild-type plants and is more preferably at least tenfold above the wild-type expression level. The section below entitled "Recombinant DNA Technology" sets forth protocols that may be used to recombinantly express the wild-type NIM1 gene in transgenic plants at higher-than-wild-type levels. Alternately, plants can be transformed with the wild-type NPR1 gene to produce disease resistant plants as described in Cao, et al. (1997).

2. Recombinant Expression of an Altered Form of the NIM Gene

Immunomodulated plants for use in the method of the present invention can also be created by recombinant expression of an altered form of the NIM1 gene, whereby the alteration of the NIM1 gene exploits both the recognition that the SAR pathway in plants shows functional parallels to the NF-κB/IκB regulation scheme in mammals and flies, as well as the discovery that the NIM1 gene product is a structural homologue of the mammalian signal transduction factor IκB subclass α. See, co-pending U.S. application Ser. No. 08/989,478, incorporated herein by reference.

The sequence of the NIM1 gene (SEQ ID NO:1) was used in BLAST searches, and matches were identified based on homology of one rather highly conserved domain in the NIM1 gene sequence to ankyrin domains found in a number of proteins such as spectrins, ankyrins, NF-κB and IκB (Michaely and Bennett, *Trends Cell Biol.* 2, 127–129 (1992)). Pair-wise visual inspections between the NIM1 protein (SEQ ID NO:2) and 70 known ankyrin-containing proteins were carried out, and striking similarities were found to members of the IκBα class of transcription regulators (Baeuerle and Baltimore 1996; Baldwin 1996). As shown in FIGS. 1A and 1B, the NIM1 protein (SEQ ID NO:2) shares significant homology with IκBα proteins from mouse, rat, and pig (SEQ ID NOs: 3, 4, and 5, respectively). NIM1 contains several important structural domains of IκBα throughout the entire length of the protein, including ankyrin domains (indicated by the dashed underscoring in FIGS. 1A and 1B), 2 amino-terminal serines (amino acids 55 and 59 of NIM1), a pair of lysines (amino acids 99 and 100 in NIM1) and an acidic C-terminus. Overall, NIM1 and IκBα share identity at 30% of the residues and conservative replacements at 50% of the residues. Thus, there is homology between IκBα and NIM1 throughout the proteins, with an overall similarity of 80%.

One way in which IκBα protein functions in signal transduction is by binding to the cytosolic transcription factor NF-κB and preventing it from entering the nucleus and altering transcription of target genes (Baeuerle and Baltimore, 1996; Baldwin, 1996). The target genes of NF-κB regulate (activate or inhibit) several cellular processes, including antiviral, antimicrobial and cell death responses (Baeuerle and Baltimore, 1996). When the signal transduction pathway is activated, IκBα is phosphorylated at two serine residues (amino acids 32 and 36 of Mouse IκBα). This programs ubiquitination at a double lysine (amino acids 21 and 22 of Mouse IκBα). Following ubiquitination, the NF-κB/IκB complex is routed through the proteosome where IκBα is degraded and NF-κB is released to the nucleus.

The phosphorylated serine residues important in IκBα function are conserved in NIM1 within a large contiguous block of conserved sequence from amino acids 35 to 84 (FIGS. 1A and 1B). In contrast to IκBα, where the double lysine is located about 15 amino acids toward the N-terminus of the protein, in NIM1 a double lysine is located about 40 amino acids toward the C-terminal end. Furthermore, a high degree of homology exists between NIM1 and IκBα in the serine/threonine rich carboxy terminal region which has been shown to be important in basal turnover rate (Sun et al., *Mol. Cell. Biol.* 16, 1058–1065 (1996)). According to the present invention based on the analysis of structural homology and the presence of elements known to be important for IκBα function, NIM1 is expected to function like the IκBα, having analogous effects on plant gene regulation.

Plants containing the wild-type NIM1 gene when treated with inducer chemicals are predicted to have more NIM1 gene product (I-κB homolog) or less phosphorylation of the NIM1 gene product (IκB homolog). In accordance with this model, the result is that the plant NF-κB homolog is kept out of the nucleus, and SAR gene expression and resistance responses are allowed to occur. In the nim1 mutant plants, a non-functional NIM1 gene product is present. Therefore, in accordance with this model, the NF-κB homolog is free to go to the nucleus and repress resistance and SAR gene expression.

Consistent with this idea, animal cells treated with salicylic acid show increased stability/abundance of IκB and a reduction of active NF-κB in the nucleus (Kopp and Ghosh, 1994). Mutations of IκB are known that act as super-repressors or dominant-negatives (Britta-Mareen Traenckner et al., *EMBO* 14: 2876–2883 (1995); Brown et al., *Science* 267: 1485–1488 (1996); Brockman et al., *Molecular and Cellular Biology* 15: 2809–2818 (1995); Wang et al., *Science* 274: 784–787 (1996)). These mutant forms of IκB bind to NF-κB but are not phosphorylated or ubiquitinated and therefore are not degraded. NF-κB remains bound to the IκB and cannot move into the nucleus.

In view of the above, altered forms of NIM1 that act as dominant-negative regulators of the SAR signal transduction pathway can be created. Plants transformed with these dominant-negative forms of NIM1 have the opposite phenotype as nim1 mutant plants in that the plants transformed with altered forms of NIM1 exhibit constitutive SAR gene expression and therefore a CIM phenotype; i.e, the transgenic plants are immunomodulated. Because of the position the NIM1 gene holds in the SAR signal transduction pathway, it is expected that a number of alterations to the gene, beyond those specifically disclosed herein, will result in constitutive expression of SAR genes and, therefore, a CIM phenotype. The section below entitled "Recombinant DNA Technology" sets forth protocols that may be used to recombinantly express the altered forms of the NIM1 gene in transgenic plants at higher-than-wild-type levels. Below are described several altered forms of the NIM1 gene that act as dominant-negative regulators of the SAR signal transduction pathway.

a. Changes of Serine Residues 55 and 59 to Alanine Residues:

Phosphorylation of serine residues in human IκBα is required for stimulus activated degradation of IκBα thereby activating NF-κB. Mutagenesis of the serine residues (S32 and S36) in human IκBα to alanine residues inhibits stimulus-induced phosphorylation, thus blocking IκBα proteosome-mediated degradation (Traenckner et al., 1995; Brown et al., 1996; Brockman et al., 1995; Wang et al., 1996). This altered form of IκBα can function as a dominant-negative form by retaining NF-κB in the cytoplasm thereby blocking downstream signaling events. Based on the amino acid sequence comparison between NIM1 and IκB shown in FIGS. 1A and 1B, serines 55 (S55) and 59 (S59) in NIM1 (SEQ ID NO:2) are homologous to S32 and S36 in human IκBα. To construct dominant-negative forms of NIM1, the serines at amino acid positions 55 and 59 are mutagenized to alanine residues. Thus, in a preferred embodiment, the NIM1 gene is altered so that the encoded product has alanines instead of serines in the amino acid positions corresponding to positions 55 and 59 of the Arabidopsis NIM1 amino acid sequence (SEQ ID NO:2).

b. N-terminal Deletion:

Deletion of amino acids 1–36 (Brockman et al., 1995; Sun et al., 1996) or 1–72 (Sun et al., 1996) of human IκBα, which includes ubiquination lysine residues K21 and K22 as well as phosphorylation sites S32 and S36, results in a dominant-negative IκBα phenotype in transfected human cell cultures. An N-terminal deletion of the first 125 amino acids of the NIM1 gene product will remove eight lysine residues that could serve as ubiquination sites as well as the putative phosphorylation sites at S55 and S59 discussed above. Thus, in a preferred embodiment, the NIM1 gene is altered so that the encoded product is missing approximately the first 125 amino acids compared to the native Arabidopsis NIM1 amino acid sequence (SEQ ID NO:2).

c. C-Terminal Deletion:

Deletion of amino acids 261–317 of human IκBα may result in enhanced intrinsic stability by blocking constitutive phosphorylation of serine and threonine residues in the C-terminus. This altered form of IκBα is expected to function as a dominant-negative form. A region rich in serine and threonine is present at amino acids 522–593 in the C-terminus of NIM1 . Thus, in a preferred embodiment, the NIM1 gene is altered so that the encoded product is missing approximately its C-terminal portion, including amino acides 522–593, compared to the native Arabidopsis NIM1 amino acid sequence (SEQ ID NO:2).

d. N-terminal/C-terminal Deletion Chimera and Ankyrin Domains:

Altered forms of the NIM1 gene product may also be produced as a result of C-terminal and N-terminal segment deletions or chimeras. In yet another embodiment of the present invention, constructs comprising the ankyrin domains from the NIM1 gene are provided.

3. Recombinant Expression of Other SAR Genes

Immunomodulated plants for use in the method of the present invention can also be created by recombinant expression of various SAR genes such as those described in Ward et al. (1991). See, for example, U.S. Pat. No. 5,614,395, which describes disease resistant plants created by overexpression of one or more PR-protein genes. Although it refers to recombinant expression of forms of the NIM1 gene particularly, the section below entitled "Recombinant DNA Technology" sets forth protocols that may also be used to recombinantly express other SAR genes such as PR-protein genes in transgenic plants at higher-than-wild-type levels.

II. Recombinant DNA Technology

The wild-type or altered form of the NIM1 gene conferring disease resistance to plants by enhancing SAR gene expression can be incorporated into plant cells using conventional recombinant DNA technology. Generally, this involves inserting DNA molecule encoding the selected form of NIM1 described above into an expression system to which the DNA molecule is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgt11, λgt10 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the chosen form of the NIM1 gene activates SAR in the transgenic plants.

A. Construction of Plant Expression Cassettes

Gene sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described infra. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN 1761ENX is useful for the cloning of cDNA sequences or gene sequences (including microbial ORF sequences) within its polylinker for the purpose of their expression under the control of the 35S promoter in transgenic plants. The entire 35S promoter-gene sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

b. Expression under a Chemically/Pathogen Regulatable Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB 1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB 1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-termninator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy etal. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN 1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Constitutive Expression, the Ubiquitin Promoter:

Ubiquitin is another gene product known to accumulate in many cell types and its promoter has been cloned from several species for use in transgenic plants (e.g. sunflower—Binet et al. Plant Science 79: 87–94 (1991) and maize—Christensen et al. Plant Molec. Biol. 12: 619–632 (1989)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The ubiquitin promoter is suitable for gene expression in transgenic plants, especially monocotyledons. Suitable vectors are derivatives of pAHC25 or any of the transformation vectors described in this application, modified by the introduction of the appropriate ubiquitin promoter and/or intron sequences.

e. Root Specific Expression:

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN 1761 ENX for the insertion of a selected gene and subsequent transfer of the entire promoter-gene-terminator cassette to a transformation vector of interest.

f. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

g. Pith-preferred Expression:

Patent Application WO 93/07278, which is herein incorporated by reference, describes the isolation of the maize trpA gene, which is preferentially expressed in pith cells. The gene sequence and promoter extending up to –1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

h. Leaf-specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15: 65–79 (1990)).

4. Targeting of the Gene Product within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai etal. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

B. Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304: 184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN 19 (Bevan, Nucl. Acids Res. (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bar gene from *Streptomyces viridochromogenes* is excised and inserted into the HpaI site of pCIB3060 (Thompson et at. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB 1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

C. Transformation

Once the coding sequence of interest has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, microinjection, and microprojectiles. In addition, bacteria from the genus Agrobacterium can be utilized to transform plant cells. Below are descriptions of representative techniques for transforming both dicotyledonous and monocotyledonous plants.

1. Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

More recently, tranformation of monocotyledons using Agrobacterium has been described. See, WO 94/00977 and U.S. Pat. No. 5,591,616, both of which are incorporated herein by reference.

III. Breeding

The immunomodulated plants obtained via tranformation with an SAR gene such as a form of the NIM1 gene can be any of a wide variety of plant species, including those of monocots and dicots; however, the immunomodulated plants used in the method of the invention are preferably selected from the list of agronomically important target crops set forth supra. The expression of the chosen form of the NIM1 gene in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female ferile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

In seeds production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a form of a NIM1 gene or a NIM1 protein that is expressed in said transformed plant at higher levels than in a wild type plant, together with a suitable carrier, together with lable instructions for the use thereof for conferring broad spectrum disease resistance to plants.

IV. Application of a Microbicide to Immunomodulated Plants

As described herein, the inventive method of protecting plants involves two steps: first, activating the SAR pathway to provide an immunomodulated plant, and second, applying a microbicide to such immunomodulated plants to attain synergistically enhanced disease resistance.

A. Conventional Microbicides

According to the method of the present invention, any commercial or conventional microbicide may be applied to immunomodulated plants obtained through any of the three above-described routes. Examples of suitable microbicides include, but are not limited to, the following fungicides: 4-[3-(4-chlorophenyl)-3-(3,4-dimethoxyphenyl)acryloyl] morpholine ("dimethomorph"), (reference: C. Tomlin (Editor): The Pesticide Manual, 10th edition, Farnham, UK, 1994, pages 351–352); 5-methyl-1,2,4-triazolo[3,4-b][1,3] benzothiazole ("tricyclazole"), (reference: C. Tomlin (Editor): The Pesticide Manual, 10th edition, Farnham, UK, 1994, pages 1017–1018); 3-allyloxy-1,2-benzothiazole-1,1-dioxide ("probonazole"), (reference: C. Tomlin (Editor): The Pesticide Manual, 10th edition, Farnham, UK, 1994, pages 831–832); α-[2-(4-chlorophenyl)ethyl]--α-(1,1-dimethylethyl)-1H-1,2,4-triazole-1-ethanol, ("tebuconazole"), (reference: EP-A-40 345); 1-[[3-(2-chlorophenyl)-2--(4-fluorophenyl)oxiran-2-yl]methyl]-1H 1,2,4-triazole, ("epoxyconazole"), (reference: EP- A-196 038); $\mu$-(4-chlorophenyl)--$\mu$-(1-cyclopropylethyl)- 1H-1,2, 4-triazole--1-ethanol, ("cyproconazole"), (reference: U.S. Pat. No. 4,664,696); 5-(4-chlorobenzyl)--2,2-dimethyl-1--(1H-1,2,4-triazol-1--ylmethyl)-cyclopentanol, ("metconazole"), (reference: EP-A-267 778); 2-(2,4-dichlorophenyl)--3-(1H-1,2,4-triazol-1-yl)-propyl--1,1,2,2-tetrafluoroethyl-ether, ("tetraconazole"), (reference: EP-A-234 242); methyl-(E)-2-{2-[6-(2-cyanophenoxy)pyrimidin--4-yloxy]phenyl}--3-methoxyacrylate, ("ICI A 5504", "azoxystrobin"), (reference: EP-A-382 375); methyl-(E)--2-methoximino--2-[α-(o-tolyloxy)--o-tolyl]acetate, ("BAS 490 F", "kresoxime methyl"), (reference: EP-A-400 417); 2-(2-phenoxyphenyl)-(E)-2-methoximino--N-methylacetamide, (reference: EP-A-398 692); [2-(2,5-dimethylphenoxymethyl)-phenyl]-(E)--2-methoximino-N-methylacetamide, (reference: EP-A-398 692); (1R,3S/1S, 3R)-2,2-dichloro--N-[(R)-1-(4-chlorophenyl)ethyl]--1-ethyl-3-methylcyclopropanecarboxamide, ("KTU 3616"), (reference: EP-A-341 475); manganese ethylenebis (dithiocarbamate)polymer-zinc complex, ("mancozeb"), (reference: U.S. Pat. No. 2,974,156); 1-[2-(2,4-dichlorophenyl)-4-propyl-1,3-dioxolan--2-ylmethyl]--1H-1, 2,4--triazole, ("propiconazole"), (reference: GB-1522657); 1-{2-[2-chloro-4-(4-chlorophenoxy)phenyl]-4-methyl--1,3-dioxolan--2-ylmethy 1)--1H-1,2,4--triazole, ("difenoconazole"), (reference: GB-209860); 1-[2-(2,4-dichlorophenyl)pentyl--1H-1,2,4-triazole, ("penconazole"), (reference: GB-1589852); cis-4-[3-(4-tert-butylphenyl)--2-methylpropyl]--2,6-dimethylmorpholine, ("fenpropimorph"), (reference: DE 2752135); 1-[3-(4-tert-butylphenyl)--2-methylpropyl]-piperidine, ("fenpropidin"), (reference: DE2752135); 4-cyclopropyl-6-methyl-N-phenyl-2-pyrimidinamine ("cyprodinil") (reference: EP-A-310550); (RS)-N-(2,6-dimethylphenyl--N-(methoxyacetyl)-alanine methyl ester ("metalaxyl"), (reference: GB-1500581); (R)-N-(2,6-dimethylphenyl--N-(methoxyacetyl)-alanine methyl ester ("R-metalaxyl"), (reference: GB-1500581); 1,2,5,6-tetrahydro--4H-pyrrolo[3,2,1-ij]quinolin-4-one ("pyroquilon"), (reference: GB-1394373); ethyl hydrogen phosphonate ("fosetyl"), (reference: C. Tomlin (Editor): *The Pesticide Manual,* 10th edition, Farnhan, UK, 1994, pages 530–532); and copper hydroxide (reference: C. Tomlin (Editor): *The Pesticide Manual,* 10th edition, Farnhan, UK, 1994, pages 229–230).

The chosen microbicide is preferably applied to the immunomodulated plants to be protected in the form of a composition with further carriers, surfactants or other application-promoting adjuvants customarily employed in formulation technology. Suitable carriers and adjuvants can be solid or liquid and are the substances ordinarily employed in formulation technology, e.g. natural or regenerated mineral substances, solvents, dispersants, wetting agents, tackifiers, thickeners, binders or fertilizers.

A preferred method of applying a microbicidal composition is application to the parts of the plants that are above the soil, especially to the leaves (foliar application). The frequency and rate of application depend upon the biological and climatic living conditions of the pathogen. The microbicide can, however, also penetrate the plant through the roots via the soil or via the water (systemic action) if the locus of the plant is impregnated with a liquid formulation (e.g. in rice culture) or if the microbicide is introduced in solid form into the soil, e.g. in the form of granules (soil application). In order to treat seed, the microbicide can also be applied to the seeds (coating), either by impregnating the tubers or grains with a liquid formulation of the microbicide, or by coating them with an already combined wet or dry formulation. In addition, in special cases, other methods of application to plants are possible, for example treatment directed at the buds or the fruit trusses.

The microbicide may be used in unmodified form or, preferably, together with the adjuvants conventionally employed in formulation technology, and is therefore formulated in known manner e.g. into emulsifiable concentrates, coatable pastes, directly sprayable or dilutable solutions, dilute emulsions, wettable powders, soluble powders, dusts, granules, or by encapsulation in e.g. polymer substances. As with the nature of the compositions, the methods of application, such as spraying, atomising, dusting, scattering, coating or pouring, are chosen in accordance with the intended objectives and the prevailing circumstances. Advantageous rates of application of the microbicide are normally from 50 g to 2 kg a.i./ha, preferably from 100 g to 1000 g a.i./ha, especially from 150 g to 700 g a.i./ha. In the case of the treatment of seed, the rates of application are from 0.5 g to 1000 g, preferably from 5 g to 100 g, a.i. per 100 kg of seed.

The formulations are prepared in known manner, e.g. by homogeneously mixing and/or grinding the microbicide with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable nonsorbent carriers are, for example, calcite or sand. In addition, a great number of pregranulated materials of inorganic or organic nature can be used, e.g. especially dolomite or pulverised plant residues.

Depending upon the nature of the microbicide, suitable surface-active compounds are non-ionic, cationic and/or anionic surfactants having good emulsifying, dispersing and wetting properties. The term "surfactants" will also be understood as comprising mixtures of surfactants.

Particularly advantageous application-promoting adjuvants are also natural or synthetic phospholipids of the cephalin and lecithin series, e.g. phosphatidylethanolamine, phosphatidylserine, phosphatidylglycerol and lysolecithin.

The agrochemical compositions generally comprise 0.1 to 99%, preferably 0.1 to 95%, active microbicidal ingredient, 99.9 to 1%, preferably 99.9 to 5%, of a solid or liquid adjuvant and 0 to 25%, preferably 0.1 to 25%, of a surfactant.

Whereas commercial products will preferably be formulated as concentrates, the end user will normally employ dilute formulations.

B. Plant Activating Microbicides

If applied to immunomodulated plants obtained through the second or third above-described route (selective breeding or genetic engineering), the microbicide may alternately be a chemical inducer of SAR (plant activating microbicide) such as a benzothiadiazole compound, an isonicotinic acid compound, or a salicylic acid compound, which are described in U.S. Pat. Nos. 5,523,311 and 5,614,395. Hence, two methods of immunomodulation are concurrently employed. By applying plant activating microbicides to immunomodulated plants obtained through either a selective breeding route or a genetic engineering route, "extra-immunomodulation" results, and synergistically enhanced disease resistance is achieved.

As described below, transgenic immunomodulated plants overexpressing NIM1 responded much faster and to much lower doses of BTH, as shown by PR-1 gene expression and resistance to *P. parasitica*, than wild-type plants. See, Example 35 and the Northern blots in FIG. 3. Synergistically enhanced disease resistance in NIM1-overexpressors can be achieved with only 10 $\mu$M BTH application, a concentration normally insufficient for any efficacy at all. Normnally phytotoxic or otherwise undesirable concentrations of SAR-inducing chemicals can be avoided by taking advantage of this synergy. In addition, one can take advantage of the alteration of the time-course of SAR activation that occurs when SAR-inducing chemicals are applied to already-immunomodulated plants such as NIM1-overexpressors. Furthermore, economic gains can be realized as a result of the decreased quantity of SAR-inducing chemicals required to provide a given level of protection to plants.

C. Conventional Microbicides in Conjunction With Plant Activating Microbicides For even greater disease resistance, both a conventional microbicide and a plant activating microbicide may be applied to immunomodulated plants obtained through either a selective breeding route or a genetic engineering route. This results in an even higher level of synergistic disease resistance compared to the level of disease resistance obtained through immunomodulation alone, through immunomodulation plus only one type of microbicide, or through the simultaneous application of both types of microbicides (conventional and plant activating). See, for example, Table 35 in Example 19.

V. Disease Resistance Evaluation

Disease resistance evaluation is performed by methods known in the art. See, Uknes et al, (1993) Molecular Plant Microbe Interactions 6: 680–685; Gorlach et al., (1996) Plant Cell 8: 629–643; Alexander et al., Proc. Natl. Acad. Sci. USA 90: 7327–7331 (1993). For example, several representative disease resistance assays are described below.

A. *Phytophthora parasitica* (Black Shank) Resistance Assay

Assays for resistance to *Phytophthora parasitica*, the causative organism of black shank, are performed on six-week-old plants grown as described in Alexander et al., Proc. Natl. Acad. Sci. USA 90: 7327–7331 (1993). Plants are watered, allowed to drain well, and then inoculated by applying 10 ml of a sporangium suspension (300 sporangia/ml) to the soil. Inoculated plants are kept in a greenhouse maintained at 23–25° C. day temperature, and 20–22° C. night temperature. The wilt index used for the assay is as follows: 0=no symptoms; 1=no symptoms; 1=some sign of wilting, with reduced turgidity; 2=clear wilting symptoms, but no rotting or stunting; 3=clear wilting symptoms with stunting, but no apparent stem rot; 4=severe wilting, with visible stem rot and some damage to root system; 5=as for 4, but plants near death or dead, and with severe reduction of root system. All assays are scored blind on plants arrayed in a random design.

B. *Pseudomonas syringae* Resistance Assay

*Pseudomonas syringae* pv. tabaci strain #551 is injected into the two lower leaves of several 6–7-week-old plants at a concentration of $10^6$ or $3\times10^6$ per ml in $H_2O$. Six individual plants are evaluated at each time point. Pseudomonas tabaci infected plants are rated on a 5 point disease severity scale, 5=100% dead tissue, 0=no symptoms. A T-test (LSD) is conducted on the evaluations for each day and the groupings are indicated after the Mean disease rating value. Values followed by the same letter on that day of evaluation are not statistically significantly different.

C. *Cercospora nicotianae* Resistance Assay

A spore suspension of *Cercospora nicotianae* (ATCC #18366) (100,000–150,000 spores per ml) is sprayed to imminent run-off onto the surface of the leaves. The plants are maintained in 100% humidity for five days. Thereafter the plants are misted with water 5–10 times per day. Six individual plants are evaluated at each time point. *Cercospora nicotianae* is rated on a % leaf area showing disease symptoms basis. A T-test (LSD) is conducted on the evaluations for each day and the groupings are indicated after the Mean disease rating value. Values followed by the same letter on that day of evaluation are not statistically significantly different.

D. *Peronospora parasitica* Resistance Assay

Assays for resistance to *Peronospora parasitica* are performed on plants as described in Uknes et al, (1993). Plants are inoculated with a combatible isolate of *P. parasitica* by spraying with a conidial suspension (approximately $5\times10^4$ spores per milliliter). Inoculated plants are incubated under humid conditions at 17° C. in a growth chamber with a 14-hr day/10-hr night cycle. Plants are examined at 3–14 days, preferably 7–12 days, after inoculation for the presence of conidiophores. In addition, several plants from each treatment are randomly selected and stained with lactophenol-trypan blue (Keogh et al., *Trans. Br. Mycol. Soc.* 74: 329–333 (1980)) for microscopic examination.

EXAMPLES

The invention is illustrated in further detail by the following detailed procedures, preparations, and examples. The examples are for illustration only, and are not to be construed as limiting the scope of the present invention.

Standard recombinant DNA and molecular cloning techniques used here are well known in the art and are described by Sambrook, et al., *Molecular Cloning, eds.*, Cold Spring Harbor Laboratory Press, Cold Spring Harbor, N.Y. (1989) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

I. Synergistic Disease Resistance Effects Achieved by Coordinate Application to Plants of a Chemical Inducer of Systemic Acquired Resistance with a Conventional Microbicide In this set of examples, SAR was induced in plants by application of a chemical inducer of SAR such as a benzothiadiazole. In addition, conventional microbicides were applied to the plants. Plants were then subjected to disease pressure from various pathogens. The combination of both methods of combating pathogens (inducing chemical+microbicide) produced a greater-than-additive, i.e., synergistic, disease-resistant effect. This effect was determined as the synergy factor (SF), i.e., the ratio of observed (O) effect to expected (E) effect.

The expected effect (E) for a given combination of active ingredients can be described by the so-called Colby formula and can be calculated as follows (Colby, S. R., "Calculating synergistic and antagonistic responses of herbicide combination". *Weeds*, Vol. 15, pages 20–22 (1967)):

ppm=milligrams of active ingredient (=a.i.) per liter of spray mixture,

X=% action caused by active ingredient I at a rate of application of p ppm of active ingredient, Y=% action caused by active ingredient II at a rate of application of q ppm active ingredient, E=expected effect of active ingredients I+II at a rate of application of p+q ppm of active ingredient (additive action).

Colby's formula reads $$E = X + Y - \frac{X \times Y}{100}.$$

Example 1

Action Against *Erysiphe graminis* On Barley

Residual-protective action: Barley plants about 8 cm in height were sprayed to drip point with an aqueous spray mixture (max. 0.02% active ingredient) and were dusted 3 to 4 days later with conidia of the fungus. The infected plants were stood in a greenhouse at 22°. Fungus infestation was generally evaluated 10 days after infection.

Systemic action: Barley plants about 8 cm in height were watered with an aqueous spray mixture (max. 0.002% active ingredient, based on the volume of the soil). Care was taken that the spray mixture did not come into contact with parts of the plants above the soil. The plants were dusted with conidia of the fungus 3 to 4 days later. The infected plants were stood in a greenhouse at 22°. Fungus infestation was generally evaluated 10 days after infection.

TABLE 1

Action against *Erysiphe graminis* on barley
component I: benzothiadiazole-7-carboxylic acid
component II: metconazol

| | mg a.i. per liter (ppm) | | | % action | | SF |
|---|---|---|---|---|---|---|
| Test no. | comp. I | comp. II | I:II | O (observed) | E (expected) | O/E |
| 1 | 0.6 | | | 0 | | |
| 2 | 2 | | | 40 | | |
| 3 | 6 | | | 89 | | |
| 4 | | 0.6 | | 10 | | |
| 5 | | 2 | | 40 | | |
| 6 | | 6 | | 51 | | |
| 7 | | 20 | | 65 | | |
| 8 | 0.6 | 0.6 | 1:1 | 37 | 10 | 3.7 |
| 9 | 0.6 | 2 | 1:3 | 59 | 40 | 1.5 |
| 10 | 0.6 | 6 | 1:10 | 81 | 51 | 1.6 |
| 11 | 0.6 | 20 | 1:30 | 78 | 65 | 1.2 |
| 12 | 2 | 6 | 1:3 | 78 | 71 | 1.1 |
| 13 | 2 | 20 | 1:10 | 98 | 79 | 1.2 |

TABLE 2

Action against *Erysiphe graminis* on barley
component I: benzothiadiazole-7-carboxylic acid
component II: tetraconazol

| | mg a.i. per liter (ppm) | | | % action | | SF |
|---|---|---|---|---|---|---|
| Test no. | comp. I | comp. II | I:II | O (observed) | E (expected) | O/E |
| 1 | 0.6 | | | 14 | | |
| 2 | 2 | | | 27 | | |
| 3 | | 0.6 | | 45 | | |
| 4 | | 2 | | 63 | | |
| 5 | 0.6 | 0.6 | 1:1 | 70 | 53 | 1.3 |
| 6 | 0.6 | 2 | 1:3 | 82 | 68 | 1.2 |
| 7 | 2 | 0.6 | 3:1 | 79 | 60 | 1.3 |

TABLE 3

Action against *Erysiphe graminis* on barley
component I: benzothiadiazole-7-carboxylic acid thiomethyl ester
component II: metconazol

| | mg a.i. per liter (ppm) | | | % action | | SF |
|---|---|---|---|---|---|---|
| Test no. | comp. I | comp. II | I:II | O (observed) | E (expected) | O/E |
| 1 | 0.6 | | | 0 | | |
| 2 | 2 | | | 33 | | |
| 3 | | 6 | | 17 | | |
| 4 | | 20 | | 33 | | |
| 5 | | 60 | | 50 | | |

TABLE 3-continued

Action against *Erysiphe graminis* on barley
component I: benzothiadiazole-7-carboxylic acid thiomethyl ester
component II: metconazol

| | mg a.i. per liter (ppm) | | | % action | | SF |
|---|---|---|---|---|---|---|
| Test no. | comp. I | comp. II | I:II | O (observed) | E (expected) | O/E |
| 6 | 0.6 | 6 | 1:10 | 33 | 17 | 1.9 |
| 7 | 0.6 | 20 | 1:30 | 50 | 33 | 1.5 |
| 8 | 0.6 | 60 | 1:100 | 83 | 50 | 1.7 |

Example 2

Action Against *Colletotrichum lagenarium* On *Cucumis sativus* L.

After a cultivation period of 10 to 14 days, cucumber plants were sprayed with a spray mixture prepared from a wettable powder formulation of the test compound. After 3 to 4 days, the plants were infected with a spore suspension ($1.0 \times 10^5$ spores/ml) of the fungus and incubated for 30 hours at high humidity and a temperature of 23° C. Incubation was then continued at normal humidity and 22° C. to 23° C. Evaluation of protective action was made 7 to 10 days after infection and was based on fungus infestation.

After a cultivation period of 10 to 14 days, cucumber plants were treated by soil application with a spray mixture prepared from a wettable powder formulation of the test compound. After 3 to 4 days, the plants were infected with a spore suspension ($1.5 \times 10^5$ spores/ml) of the fungus and incubated for 30 hours at high humidity and a temperature of 23° C. Incubation was then continued at normal humidity and 22° C. Evaluation of protective action was made 7 to 10 days after infection and was based on fungus infestation.

TABLE 4

Action Against *Colletotrichum lagenarium* On *Cucumis sativus* L./Foliar Application
component I: benzothiadiazole-7-carboxylic acid
component II: azoxystrobin

| | mg a.i. per liter (ppm) | | | % action | | SF |
|---|---|---|---|---|---|---|
| Test no. | comp. I | comp. II | I:II | O (observed) | E (expected) | O/E |
| 1 | 0.06 | | | 0 | | |
| 2 | 0.2 | | | 5 | | |
| 3 | 2 | | | 22 | | |
| 4 | | 0.06 | | 5 | | |
| 5 | | 0.2 | | 9 | | |
| 6 | | 0.6 | | 12 | | |
| 7 | | 6 | | 17 | | |
| 8 | 0.06 | 0.06 | 1:1 | 16 | 5 | 3.2 |
| 9 | 2 | 0.2 | 10:1 | 65 | 29 | 2.2 |
| 10 | 2 | 0.6 | 3:1 | 49 | 31 | 1.6 |
| 11 | 2 | 6 | 1:3 | 44 | 35 | 1.3 |

TABLE 5

Action Against *Colletotrichum lagenarium* On *Cucumis sativus* L./Soil Application
component I: benzothiadiazole-7-carboxylic acid
component II: azoxystrobin

| Test no. | mg a.i. per liter (ppm) comp. I | comp. II | I:II | % action O (observed) | E (expected) | SF O/E |
|---|---|---|---|---|---|---|
| 1 | 0.006 | | | 0 | | |
| 2 | 0.02 | | | 40 | | |
| 3 | 0.06 | | | 49 | | |
| 4 | 0.2 | | | 91 | | |
| 5 | | 0.2 | | 0 | | |
| 6 | | 0.6 | | 9 | | |
| 7 | | 2 | | 28 | | |
| 8 | | 6 | | 66 | | |
| 9 | 0.006 | 0.2 | 1:30 | 11 | 0 | * |
| 10 | | 0.6 | 1:100 | 30 | 9 | 3.3 |
| 11 | | 2 | 1:300 | 83 | 28 | 3.0 |
| 12 | 0.02 | 6 | 1:300 | 97 | 80 | 1.2 |
| 13 | 0.06 | 6 | 1:100 | 100 | 82 | 1.2 |

*synergy factor SF cannot be calculated

TABLE 6

Action Against *Colletotrichum lagenarium* On *Cucumis sativus* L./Foliar Application
component I: benzothiadiazole-7-carboxylic acid
component II: cresoxime methyl

| Test no. | mg a.i. per liter (ppm) comp. I | comp. II | I:II | % action O (observed) | E (expected) | SF O/E |
|---|---|---|---|---|---|---|
| 1 | 0.2 | | | 3 | | |
| 2 | 0.6 | | | 51 | | |
| 3 | | 2 | | 0 | | |
| 4 | | 20 | | 41 | | |
| 5 | 0.2 | 2 | 1:10 | 15 | 3 | 5 |
| 6 | 0.2 | 20 | 1:100 | 61 | 43 | 1.4 |

TABLE 7

Action Against *Colletotrichum lagenarium* On *Cucumis sativus* L./Foliar Application
component I: benzothiadiazole-7-carboxylic acid thiomethyl ester
component II: azoxystrobin

| Test no. | mg a.i. per liter (ppm) comp. I | comp. II | I:II | % action O (observed) | E (expected) | SF O/E |
|---|---|---|---|---|---|---|
| 1 | 0.6 | | | 16 | | |
| 2 | 0.2 | | | 22 | | |
| 3 | 6 | | | 60 | | |
| 4 | | 2 | | 18 | | |
| 5 | | 6 | | 75 | | |
| 6 | 0.06 | 2 | 1:30 | 43 | 31 | 1.4 |
| 7 | 0.2 | 2 | 1:10 | 57 | 36 | 1.6 |

TABLE 8

Action Against *Colletotrichum lagenarium* On *Cucumis sativus* L./Soil Application
component I: benzothiadiazole-7-carboxylic acid thiomethyl ester
component II: azoxystrobin

| Test no. | mg a.i. per liter (ppm) comp. I | comp. II | I:II | % action O (observed) | E (expected) | SF O/E |
|---|---|---|---|---|---|---|
| 1 | 0.006 | | | 0 | | |
| 2 | 0.02 | | | 6 | | |
| 3 | 0.06 | | | 23 | | |
| 4 | 0.2 | | | 36 | | |
| 5 | | 0.02 | | 1 | | |
| 6 | | 0.06 | | 5 | | |
| 7 | | 0.6 | | 27 | | |
| 8 | | 2 | | 61 | | |
| 9 | | 6 | | 93 | | |
| 10 | 0.006 | 0.02 | 1:3 | 26 | 1 | 26 |
| 11 | 0.006 | 0.6 | 1:100 | 44 | 27 | 1.6 |
| 12 | 0.006 | 2 | 1:300 | 84 | 61 | 1.4 |
| 13 | 0.02 | 0.02 | 1:1 | 23 | 7 | 3.3 |
| 14 | 0.02 | 2 | 1:100 | 77 | 64 | 1.2 |
| 15 | 0.06 | 0.02 | 3:1 | 42 | 24 | 1.8 |
| 16 | 0.06 | 2 | 1:30 | 92 | 70 | 1.3 |
| 17 | 0.2 | 2 | 1:10 | 93 | 75 | 1.2 |

Example 3

Action Against *Cercospora nicotianae* on Tobacco Plants

Tobacco plants (6 weeks old) were sprayed with a formulated solution of the test compound (concentration: max. 0.02% active ingredient). Four days after treatment, the plants were inoculated with a sporangia suspension of *Cercospora nicotianae* (150,000 spores/ml) and kept at high humidity for 4 to 5 days and then incubated further under a normal day/night sequence. Evalation of the symptoms in the tests was based on the leaf surface infested with fungus.

TABLE 9

Action Against *Cercospora nicotianae* On Tobacco Plants
component I: benzothiadiazole-7-carboxylic acid thiomethyl ester
component II: tebuconazol

| Test no. | mg a.i. per liter (ppm) comp. I | comp. II | I:II | % action O (observed) | E (expected) | SF O/E |
|---|---|---|---|---|---|---|
| 1 | 0.2 | | | 0 | | |
| 2 | 2 | | | 17 | | |
| 3 | 6 | | | 55 | | |
| 4 | 20 | | | 78 | | |
| 5 | | 2 | | 0 | | |
| 6 | | 6 | | 0 | | |
| 7 | 0.2 | 2 | 1:10 | 87 | 0 | * |
| 8 | 0.2 | 6 | 1:30 | 97 | 0 | * |
| 9 | 2 | 2 | 1:1 | 87 | 17 | 5.1 |
| 10 | 2 | 6 | 1:3 | 94 | 17 | 5.5 |
| 11 | 6 | 2 | 3:1 | 87 | 55 | 1.6 |
| 12 | 6 | 6 | 1:1 | 90 | 55 | 1.6 |
| 13 | 20 | 2 | 10:1 | 97 | 78 | 1.2 |
| 14 | 20 | 6 | 3:1 | 97 | 78 | 1.2 |

TABLE 10

Action Against *Cercospora nicotianae* On Tobacco Plants
component I: benzothiadiazole-7-carboxylic acid thiomethyl ester
component II: cyproconazol

| | mg a.i. per liter (ppm) | | | % action | | SF |
|---|---|---|---|---|---|---|
| Test no. | comp. I | comp. II | I:II | O (observed) | E (expected) | O/E |
| 1 | 0.2 | | | 0 | | |
| 2 | 2 | | | 17 | | |
| 3 | 6 | | | 55 | | |
| 4 | 20 | | | 78 | | |
| 5 | | 2 | | 0 | | |
| 6 | | 6 | | 0 | | |
| 7 | 0.2 | 2 | 1:10 | 78 | 0 | * |
| 8 | 0.2 | 6 | 1:30 | 84 | 0 | * |
| 9 | 2 | 2 | 1:1 | 90 | 17 | 5.3 |
| 10 | 2 | 6 | 1:3 | 94 | 17 | 5.5 |
| 11 | 6 | 2 | 3:1 | 87 | 55 | 1.6 |
| 12 | 6 | 6 | 1:1 | 93 | 55 | 1.7 |
| 13 | 20 | 2 | 10:1 | 100 | 78 | 1.3 |
| 14 | 20 | 6 | 3:1 | 100 | 78 | 1.3 |

TABLE 11

Action Against *Cercospora nicotianae* On Tobacco Plants
component I: benzothiadiazole-7-carboxylic acid
component II: fenpropimorph

| | kg of a.i. per ha | | | % action | | SF |
|---|---|---|---|---|---|---|
| Test no. | comp. I | comp. II | I:II | O (observed) | E (expected) | O/E |
| 0 | — | — | | 0 (control) | | |
| 1 | 0.2 | | | 0 | | |
| 2 | 0.6 | | | 3 | | |
| 3 | 2 | | | 69 | | |
| 4 | 6 | | | 79 | | |
| 5 | | 2 | | 13 | | |
| 6 | | 6 | | 23 | | |
| 7 | | 10 | | 42 | | |
| 8 | 0.2 | 2 | 1:10 | 52 | 13 | 4 |
| 9 | 0.2 | 6 | 1:30 | 61 | 23 | 2.7 |
| 10 | 0.6 | 2 | 1:3 | 71 | 16 | 4.4 |
| 11 | 6 | 6 | 1:1 | 100 | 83 | 1.2 |

TABLE 12

Action Against *Cercospora nicotianae* On Tobacco Plants
component I: benzothiadiazole-7-carboxylic acid
component II: difenoconazole

| | kg of a.i. per ha | | | % action | | SF |
|---|---|---|---|---|---|---|
| Test no. | comp. I | comp. II | I:II | O (observed) | E (expected) | O/E |
| 0 | — | — | | 0 (control) | | |
| 1 | 2 | | | 69 | | |
| 2 | 6 | | | 79 | | |
| 3 | 20 | | | 100 | | |
| 4 | | 0.6 | | 3 | | |
| 5 | | 2 | | 23 | | |
| 6 | | 6 | | 32 | | |
| 7 | 2 | 0.6 | 3:1 | 90 | 70 | 1.3 |
| 8 | 6 | 0.6 | 10:1 | 100 | 80 | 1.3 |

Example 4
Action Against *Pyricularia oryzae* on Rice Plants

Rice plants about 2 weeks old were placed together with the soil around the roots in a container filled with spray mixture (max. 0.006% active ingredient). 96 hours later, the rice plants were infected with a conidia suspension of the fungus. Fungus infestation was evaluated after incubating the infected plants for 5 days at 95–100% relative humidity and about 24° C.

TABLE 13

Action Against *Pyricularia oryzae* On Rice Plants
component I: benzothiadiazole-7-carboxylic acid thiomethyl ester
component II: KTU 3616

| | mg a.i. per liter (ppm) | | | % action | | SF |
|---|---|---|---|---|---|---|
| Test no. | comp. I | comp. II | I:II | O (observed) | E (expected) | O/E |
| 1 | 6 | | | 15 | | |
| 2 | | 0.02 | | 0 | | |
| 3 | | 0.06 | | 28 | | |
| 4 | | 0.2 | | 47 | | |
| 5 | | 0.6 | | 79 | | |
| 6 | | 2 | | 83 | | |
| 7 | | 6 | | 91 | | |
| 8 | 6 | 0.02 | 300:1 | 42 | 15 | 2.8 |
| 9 | 6 | 0.06 | 100:1 | 76 | 39 | 1.9 |
| 10 | 6 | 0.2 | 30:1 | 98 | 55 | 1.8 |
| 11 | 6 | 0.6 | 10:1 | 98 | 82 | 1.2 |
| 12 | 6 | 2 | 3:1 | 100 | 86 | 1.2 |
| 13 | 6 | 6 | 1:1 | 98 | 92 | 1.1 |

On a 12 m² plot, rice plants were sprayed with a spray mixture prepared with a wettable powder of the active ingredient. Infection was naturally. For evaluation, the leaf area infested with the fungus was measured 44 days post-application. The following results were obtained:

TABLE 14

Action Against *Pyricularia oryzae* On Rice Plants in the open
Component I: Compound ID(thiomethyl benzothiazole-7-carboxylate)
component II: Compound IIJ (pyroquilon)

| | kg of a.i. per ha | | | % action | | SF |
|---|---|---|---|---|---|---|
| Test no. | comp. I | comp. II | I:II | O (observed) | E (expected) | O/E |
| — | — | — | | 0 (control) | | |
| 1 | 0.25 | | | 22 | | |
| 2 | 0.5 | | | 50 | | |
| 3 | | 0.75 | | 46 | | |
| 4 | | 1.5 | | 82 | | |
| 5 | 0.25 | 0.75 | 1:3 | 80 | 58 | 1.4 |
| 6 | 0.5 | 0.75 | 1:1.5 | 85 | 73 | 1.2 |

Rice plants about 2 weeks old were placed together with the soil around the roots in a container filled with spray mixture. Fungus infestation was evaluated 36 days later. Infestation of the untreated plants corresponded to 0% action.

TABLE 15

Action Against *Pyricularia oryzae* On Rice Plants
Component I: benzothiadiazole-7-carboxylic acid thiomethyl ester
Component II: tricyclazole

| | mg a.i. per liter (ppm) | | | % action | | SF |
|---|---|---|---|---|---|---|
| Test no. | comp. I | comp. II | I:II | O (observed) | E (expected) | O/E |
| 1 | 0.5 | | | 65 | | |
| 2 | 0.25 | | | 39 | | |
| 3 | 0.1 | | | 18 | | |
| 4 | 0.05 | | | 5 | | |
| 5 | | 1 | | 74 | | |
| 6 | | 0.5 | | 71 | | |

TABLE 15-continued

Action Against *Pyricularia oryzae* On Rice Plants
Component I: benzothiadiazole-7-carboxylic acid thiomethyl ester
Component II: tricyclazole

| Test no. | mg a.i. per liter (ppm) comp. I | comp. II | I:II | % action O (observed) | E (expected) | SF O/E |
|---|---|---|---|---|---|---|
| 7 | | 0.25 | | 48 | | |
| 8 | | 0.1 | | 32 | | |
| 9 | 0.25 | 0.25 | 1:1 | 75 | 68 | 1.1 |
| 10 | 0.1 | 0.25 | 1:2.5 | 69 | 57 | 1.2 |
| 11 | 0.1 | 0.1 | 1:1 | 61 | 44 | 1.4 |
| 12 | 0.05 | 1 | 1:20 | 80 | 75 | 1.1 |
| 13 | 0.05 | 0.25 | 1:5 | 58 | 50 | 1.2 |

Example 5

Action Against Colletotrichum sp. (Anthracnose) and Cercospora sp. (Leaf Spot) on Chili Effects on crop yield: In a plot of land about 10 m² (test location: Cikampek, Java, Indonesia), chili plants were sprayed a total of 7 times at intervals of about 7 days with 500–700 liters spray mixture per hectare. Three days after the first spraying, the plants were infected artifically with the fungus.

TABLE 16

Action Against Colletotrichum: Evaluation was made by assessing infestation on the chili fruits after the fifth spraying.
component I: benzothiadiazole-7-carboxylic acid thiomethyl ester
component II: mancozeb

| Test no. | mg a.i. per liter (ppm) comp. I | comp. II | I:II | % action O (observed) | E (expected) | SF O/E |
|---|---|---|---|---|---|---|
| 1 | 5 | | | 55 | | |
| 2 | | 100 | | 12 | | |
| 3 | 5 | 100 | 1:20 | 77 | 59 | 1.3 |

TABLE 17

Action Against Cercospora: Evaluation was made by assessing infestation on the leaves after the sixth spraying.
component I: benzothiadiazole-7-carboxylic acid thiomethyl ester
component II: mancozeb

| Test no. | mg a.i. per liter (ppm) comp. I | comp. II | I:II | % action O (observed) | E (expected) | SF O/E |
|---|---|---|---|---|---|---|
| 1 | 5 | | | 76 | | |
| 2 | | 100 | | 8 | | |
| 3 | 5 | 100 | 1:20 | 87 | 78 | 1.1 |

TABLE 18

Action On Crop Yield: The chilis were harvested after the sixth spraying.
component I: benzothiadiazole-7-carboxylic acid thiomethyl ester
component II: mancozeb

| Test no. | mg a.i. per liter (ppm) comp. I | comp. II | I:II | Crop yield in kg per hactare O (observed) | E (expected) | SF O/E |
|---|---|---|---|---|---|---|
| 1 | 5 | | | 459 | | |
| 2 | | 100 | | 8 | | |
| 3 | 5 | 100 | 1:20 | 1400 | ca 460 | ca 3 |

Example 6

Action Against *Puccinia recondita* in Wheat 7-day-old wheat plants were sprayed to drip point with a spray mixture prepared from a formulated active ingredient, or combination of active ingredients. After 4 days, the treated plants were infected with a conidia suspension of the fungus, and the treated plants were subsequently incubated for 2 days at a relative atmospheric humidity of 90–100% and 20 C. 10 days post-infection, the fungus infestation was assessed.

TABLE 19

Action Against *Puccinia recondita* In Wheat
Component I: thiomethyl benzothiadiazole-7-carboxylate
Component II: propiconazole

| Test no. | mg a.i. per liter (ppm) comp. I | comp. II | I:II | % action O (observed) | E (expected) | SF O/E |
|---|---|---|---|---|---|---|
| — | — | — | — | 0(control) | | |
| 1 | 100 | | | 51 | | |
| 2 | | 5 | | 10 | | |
| 3 | 100 | 5 | 20:1 | 79 | 56 | 1.4 |

TABLE 20

Action Against *Puccinia recondita* In Wheat
Component I: benzothiadiazole-7-carboxylic acid
Component II: fenpropidine

| Test no. | kg of a.i. per ha comp. I | comp. II | I:II | % action O (observed) | E (expected) | SF O/E |
|---|---|---|---|---|---|---|
| — | — | — | — | 0 (control) | | |
| 1 | 6 | | | 20 | | |
| 2 | 20 | | | 40 | | |
| 3 | | 20 | | 40 | | |
| 4 | | 60 | | 60 | | |
| 5 | 6 | 20 | 1:3 | 73 | 52 | 1.4 |
| 6 | 6 | 20 | 1:10 | 75 | 68 | 1.1 |

Example 7

Action Against *Erysiphe graminis* in Wheat

In field trials (10 m²), winter wheat in the growth phase was sprayed with a spray mixture prepared with a wettable powder of the active ingredient. Infection was naturally. 10 days post-infection, the fungus infestation was assessed. The following results were obtained:

TABLE 21

Action Against *Erysiphe graminis* In Wheat
Component I: thiomethyl benzothiadiazole-7-carboxylate
Component II: propiconazole

| | g of a.i. per ha | | | % action | | SF |
|---|---|---|---|---|---|---|
| Test no. | comp. I | comp. II | I:II | O (observed) | E (expected) | O/E |
| — | — | — | | 0 (control) | | |
| 1 | 5 | | | 29 | | |
| 2 | | 50 | | 2 | | |
| 3 | | 100 | | 31 | | |
| 4 | 5 | 50 | 1:10 | 49 | 32 | 1.5 |
| 5 | 5 | 100 | 1:20 | 59 | 51 | 1.2 |

TABLE 22

Action Against *Erysiphe graminis* In Wheat
Component I: thiomethyl benzothiadiazole-7-carboxylate
Component II: cyprodinil

| | g of a.i. per ha | | | % action | | SF |
|---|---|---|---|---|---|---|
| Test no. | comp. I | comp. II | I:II | O (observed) | E (expected) | O/E |
| — | — | — | | 0 (control) | | |
| 1 | 5 | | | 29 | | |
| 2 | | 50 | | 2 | | |
| 3 | | 100 | | 31 | | |
| 4 | 5 | 50 | 1:10 | 49 | 32 | 1.5 |
| 5 | 5 | 100 | 1:20 | 59 | 51 | 1.2 |

Example 8

Action Against *Mycosphaerella fijiensis* in Bananas 40 banana plants in a 300 m² plot were sprayed at 17–19 day intervals with a spray mixture prepared with the wettable powder of the active ingredient; in total 6 times. Infection was naturally. For evaluation, the leaf infested with the fungus was measured. The following results were obtained:

TABLE 23

Action Against *Mycosphaerella fijiensis* In Bananas
Component I: thiomethyl benzothiadiazole-7-carboxylate
Component II: propiconazole

| | g of a.i. per ha | | | % action | | SF |
|---|---|---|---|---|---|---|
| Test no. | comp. I | comp. II | I:II | O (observed) | E (expected) | O/E |
| — | — | — | | 0 (control) | | |
| 1 | 50 | | | 19 | | |
| 2 | | 50 | | 26 | | |
| 3 | 50 | 50 | 1:1 | 46 | 40 | 1.15 |

Example 9

Action Against *Alternaria solani* in Tomatoes

Tomato plants on a 7 m² plot were sprayed at 7-day intervals with a spray mixture prepared with a wettable powder of the active ingredient; in total 9 times. Infection was naturally. For evaluation, the leaf infested with the fungus was measured. The following results were obtained:

TABLE 24

Action Against *Alternaria solani* In Tomatoes in the open
Component I: thiomethyl benzothiadiazole-7-carboxylate
Component II: cyprodinil

| | g of a.i. per ha | | | % action | | SF |
|---|---|---|---|---|---|---|
| Test no. | comp. I | comp. II | I:II | O (observed) | E (expected) | O/E |
| — | — | — | | 0 (control) | | |
| 1 | 2.5 | | | 32 | | |
| 2 | | 12.5 | | 30 | | |
| 3 | | 25 | | 51 | | |
| 4 | 2.5 | 12.5 | 1:5 | 79 | 53 | 1.5 |
| 5 | 2.5 | 25 | 1:10 | 80 | 67 | 1.2 |

Example 10

Action Against *Phytophthora infestans* in Tomatoes

Tomato plants cv. "Roter Gnom" were sprayed to drip point with a spray mixture prepared with the formulated active ingredient, or combination of active ingredients. After 4 days, the treated plants were sprayed with a sporangia suspension of the fungus and subsequently incubated in a cabinet for 2 days at 18–20° C. and a relative atmospheric humidity of 90–100%. 5 days post-infection, the fungus infestation was assessed. The following results were obtained:

TABLE 25

Action Against *Phytophthora infestans* In Tomatoes
Component I: thiomethyl benzothiadiazole-7-carboxylate
Component II: metalaxyl

| | mg of a.i. per liter | | | % action | | SF |
|---|---|---|---|---|---|---|
| Test no. | comp. I | comp. II | I:II | O (observed) | E (expected) | O/E |
| — | — | — | | 0 (control) | | |
| 1 | 5 | | | 14 | | |
| 2 | 25 | | | 36 | | |
| 3 | 100 | | | 61 | | |
| 4 | 500 | | | 72 | | |
| 5 | | 0.1 | | 13 | | |
| 6 | | 1 | | 23 | | |
| 7 | | 10 | | 35 | | |
| 8 | | 50 | | 68 | | |
| 9 | 5 | 0.1 | 50:1 | 50 | 25 | 2.0 |
| 10 | 5 | 1 | 5:1 | 62 | 34 | 1.8 |
| 11 | 5 | 10 | 1:2 | 87 | 44 | 2.0 |
| 12 | 5 | 50 | 1:10 | 84 | 73 | 1.2 |
| 13 | 25 | 50 | 1:2 | 92 | 80 | 1.2 |
| 14 | 100 | 10 | 10:1 | 85 | 75 | 1.1 |
| 15 | 100 | 50 | 2:1 | 95 | 88 | 1.1 |
| 16 | 500 | 10 | 50:1 | 97 | 82 | 1.2 |

TABLE 26

Action Against *Phytophthora infestans* In Tomatoes
Component I: benzothiadiazole-7-carboxylic acid
Component II: metalaxyl

| | mg of a.i. per liter | | | % action | | SF |
|---|---|---|---|---|---|---|
| Test no. | comp. I | comp. II | I:II | O (observed) | E (expected) | O/E |
| — | — | — | | 0 (control) | | |
| 1 | 0.1 | | | 0 | | |
| 2 | 0.5 | | | 9 | | |
| 3 | 1 | | | 22 | | |
| 4 | 5 | | | 45 | | |
| 5 | | 1 | | 13 | | |

TABLE 26-continued

Action Against *Phytophthora infestans* In Tomatoes
Component I: benzothiadiazole-7-carboxylic acid
Component II: metalaxyl

| | mg of a.i. per liter | | | % action | | SF |
|---|---|---|---|---|---|---|
| Test no. | comp. I | comp. II | I:II | O (observed) | E (expected) | O/E |
| 6 | | 10 | | 33 | | |
| 7 | | 50 | | 63 | | |
| 8 | | 100 | | 83 | | |
| 9 | 0.1 | 1 | 1:10 | 36 | 13 | 2.8 |
| 10 | 0.5 | 1 | 1:2 | 29 | 21 | 1.4 |
| 11 | 1 | 1 | 1:1 | 57 | 32 | 1.8 |
| 12 | 1 | 10 | 1:10 | 79 | 48 | 1.6 |
| 13 | 5 | 1 | 5:1 | 61 | 52 | 1.2 |

Example 11

Action Against *Pseudoperonospora cubensis* in Cucumbers

16–19-day-old cucumber plants ("Wisconsin") were sprayed to drip point with a spray mixture prepared with the formulated active ingredient, or combination of active ingredient, or combination of active ingredients. After 4 days, the treated plants were infected with sporangia of *Pseudoperonospora cubenswas* (strain 365, Ciba; max. 5000 per ml), and the treated plants were subsequently incubated for 1–2 days at 18–20 C. and a relative atmospheric humidity of 70–90%. 10 days post-infection, the fungus infestation was assessed and compared with the infestation on untreated plants. The following results were obtained:

TABLE 27

Action Against *Pseudoperonospora cubensis* In Cucumbers
Component I: benzothiadiazole-7-carboxylic acid
Component II: metalaxyl

| | mg of a.i. per liter | | | % action | | SF |
|---|---|---|---|---|---|---|
| Test no. | comp. I | comp. II | I:II | O (observed) | E (expected) | O/E |
| — | — | — | | 0 (control) | | |
| 1 | 0.05 | | | 0 | | |
| 2 | 0.5 | | | 6 | | |
| 3 | 5 | | | 66 | | |
| 4 | | 0.5 | | 31 | | |
| 5 | | 5 | | 66 | | |
| 6 | | 50 | | 91 | | |
| 7 | 0.05 | 0.5 | 1:10 | 66 | 31 | 2.1 |
| 8 | 0.05 | 5 | 1:100 | 83 | 66 | 1.3 |
| 9 | 0.5 | 0.5 | 1:1 | 83 | 35 | 2.4 |
| 10 | 0.5 | 5 | 1:10 | 83 | 68 | 1.2 |

Example 12

Action Against *Peronospora tabacina* on Tobacco Plants

Tobacco plants (6 weeks old) were sprayed with a formulated solution of the test compound. Four days after treatment, the plants were inoculated with a sporangia suspension of the fungus, kept at high humidity for 4 to 5 days and then incubated further under a normal day/night sequence. Evaluation of the symptoms in the tests was based on the leaf surface infested with fungus. The infestation of the untreated plants corresponded to 0% action.

TABLE 28

Action Against *Peronospora tabacina* On Tobacco Plants
Component I: benzothiadiazole-7-carboxylic acid thiomethyl ester
Component II: dimethomorph

| | mg of a.i. per liter (ppm) | | | % action | | SF |
|---|---|---|---|---|---|---|
| Test no. | comp. I | comp. II | I:II | O (observed) | E (expected) | O/E |
| 1 | 0.03 | | | 14 | | |
| 2 | 0.1 | | | 34 | | |
| 3 | 0.3 | | | 88 | | |
| 4 | | 0.3 | | 52 | | |
| 5 | | 1 | | 52 | | |
| 6 | 0.03 | 1 | 1:33 | 74 | 59 | 1.3 |
| 7 | 0.1 | 0.3 | 1:3 | 92 | 68 | 1.4 |
| 8 | 0.1 | 1 | 1:10 | 95 | 68 | 1.4 |

Example 13

Action Against *Peronospora parasitica* in *Arabidopsis thaliana*

The fungicides metalaxyl, fosetyl, and copper hydroxide, and the SAR activator benzo(1,2,3)-thiadiazole-7-carbothioc acid S-methyl ester (BTH), formulated as 25%, 80%, 70%, and 25% active ingredient (ai) respectively, with a wettable powder carrier, were applied as fine mist to leaves of three week-old plants. The wettable powder alone was applied as a control. Three days later, plants were inoculated with a *Peronospora parasitica* conidial suspension as described in Delaney et al. (1995). Ws plants were inoculated with the compatible *P. parasitica* isolate Emwa (1–2× $10^5$ spores/ml); Col plants were inoculated with the compatible *P. parasitica* isolate Noco2 (0.5–1×$10^5$ spores/ml). Following inoculation, plants were covered to maintain high humidity and were placed in a Percival growth chamber at 17° C. with a 14-hr day/10-hr night cycle (Uknes et al., 1993). Tissue was harvested 8 days after inoculation.

Fungal infection progression was followed for 12 days by viewing under a dissecting microscope to score development of conidiophores (Delaney, et al. (1994); Dietrich, et al. (1994)). Lactophenoltrypan blue staining of individual leaves was carried out to observe fungal growth within leaf tissue. Fungal growth was quantified using a rRNA fungal probe that was obtained by PCR according to White et al. (1990; PCR Protocols: A guide to Methods and Application, 315–322) using primers NS1 and NS2 and *P. parasitica* EmWa DNA as templates. RNA was purified from frozen tissue by phenol/chloroform extraction following lithium chloride precipitation (Lagrimini et al, 1987: PNAS, 84: 7542–7546). Samples (7.5 ug) were separated by electrophoresis through formaldehyde agarose gels and blotted to nylon membranes (Hybond-N+, Amersham) as described by Ausbel et al. (1987). Hybridizations and washing were according to Church and Gilbert (1984, *PNAS*, 81: 1991–1995). Relative amounts of the transcript were determined using a Phosphor Imager (Molecular Dynamics, Sunnyvale, Calif.) following manufacturers instructions. Sample loading was normalized by probing stripped filter blots with the constitutively expressed b-tubulin Arabidopsis cDNA. The infestation of the untreated plants corresponded to 0% fungal growth inhibition. The following results were obtained:

TABLE 29

Action Against *Peronospora parasitica* NoCo2 In *Arabidopsis thaliana* (Col-0)
Component I: benzo(1,2,3)thiadiazole-7-carbothioic acid S-methyl ester
Component II: metalaxyl

| | Components | | Fungal Growth Inhibition % | | Synergy Factor |
|---|---|---|---|---|---|
| Test no. | BTH | metalaxyl | O (observed) | E (expected) | O/E |
| control | — | — | 0 | | |
| 1 | 0.01 mM | — | 0 | | |
| 2 | — | 0.1 mg/l | 0 | | |
| 3 | 0.01 mM | 0.1 mg/l | 40.7 | 0 | ∞ |

TABLE 30

Action Against *Peronospora parasitica* Emwa In *Arabidopsis thaliana* (Ws)
Component I: benzo[1,2,3]thiadiazole-7-carbothioic acid-S-methyl ester
Component II: metalaxyl

| | Components | | Fungal Growth Inhibition % | | Synergy Factor |
|---|---|---|---|---|---|
| Test no. | BTH | metalaxyl | O (observed) | E (expected) | O/E |
| control | — | — | 0 | | |
| 1 | 0.01 mM | — | 20 | | |
| 2 | 0.003 mM | — | 0 | | |
| 3 | — | 2.5 mg/l | 75 | | |
| 4 | — | 0.5 mg/l | 50 | | |
| 5 | — | 0.1 mg/l | 50 | | |
| 6 | 0.01 mM | 2.5 mg/l | 100 | 90 | 1.1 |
| 7 | 0.01 mM | 0.5 mg/l | 95 | 70 | 1.4 |
| 8 | 0.01 mM | 0.1 mg/l | 88 | 70 | 1.3 |
| 9 | 0.003 mM | 2.5 mg/l | 100 | 75 | 1.3 |

TABLE 31

Action Against *Peronospora parasitica* Emwa In *Arabidopsis thaliana* (Ws)
Component I: benzo[1,2,3]thiadiazole-7-carbothioic acid-S-methyl ester
Component II: fosetyl

| | Components | | Fungal Growth Inhibition % | | Synergy Factor |
|---|---|---|---|---|---|
| Test no. | BTH | fosetyl | O (observed) | E (expected) | O/E |
| control | — | — | 0 | | |
| 1 | 0.01 mM | — | 30 | | |
| 2 | — | 1.0 g/l | 40 | | |
| 3 | — | 0.2 g/l | 10 | | |
| 4 | — | 0.04 g/l | 0 | | |
| 5 | 0.01 mM | 1.0 g/l | 100 | 70 | 1.4 |
| 6 | 0.01 mM | 0.2 g/l | 100 | 40 | 2.5 |
| 7 | 0.01 mM | 0.04 g/l | 95 | 30 | 3.2 |

TABLE 32

Action Against *Peronospora parasitica* Emwa In *Arabidopsis thaliana* (Ws)
Component I: benzo(1,2,3)thiadiazole-7-carbothioic acid-S-methyl ester
Component II: copper hydroxide

| | Components | | Fungal Growth Inhibition % | | Synergy Factor |
|---|---|---|---|---|---|
| Test no. | BTH | Cu(OH)$_2$ | O (observed) | E (expected) | O/E |
| control | — | — | 0 | | |
| 1 | 0.01 mM | — | 30 | | |
| 2 | — | 0.01 g/l | 0 | | |
| 3 | 0.01 mM | 0.01 g/l | 85 | 30 | 2.8 |

As can be seen in Table 29, synergistic disease-resistant effects were demonstrated in the wild-type Arabidopsis Col-0 plants. No fungal growth inhibition was observed by separately applying either 0.01 mM BTH or 0.0001 g/L metalaxyl to the plants, because these concentrations are normally insufficient for efficacy. However, by applying both of these compounds to the plants at these normally insufficient concentrations, 40.7% fungal growth inhibition was observed, which is clearly a synergistic effect. Tables 30–32 show synergistic disease-resistant effects in wild-type Arabidopsis Ws plants. Only 20–30% fungal growth inhibition was observed by applying 0.01 mM BTH to the Ws plants. However, by simultaneously applying BTH and either metalaxyl, fosetyl, or copper hydroxide to the plants, synergistic disease resistance was observed. These combined antifungal effects, which result in a decrease in the effective concentration of the fungicide and BTH required for pathogen control, allow the reduction of the chemical dose needed to stop fungal growth and therefore mitigate the incidence of foliar damage due to chemical tolerance.

II. Synergistic Disease Resistance Effects Achieved By Application Of Conventional Microbicides and/ or Chemical Inducers of Systemic Acquired Resistance To Constitutive Immunity (CIM) Mutant Plants In this set of examples, a high-throughput Northern blot screen was developed to identify mutant plants having high concentrations of PR-1 mRNA during normal growth, with the idea that these mutants also exhibit systemic acquired resistance. A number of mutants have been isolated using this screen and they have been shown to accumulate not only PR-1 but also PR-2 and PR-5 mRNAs (Lawton et al. (1993); Dietrich et al. (1994); and Weymann et al. (1 995). These mutants also have elevated levels of SA and are resistant to pathogen infection, confirming that this approach can be used to isolate SAR signal transduction mutants.

Two classes of SAR signal transduction mutants have been isolated using this screen. One class has been designated as lsd mutants (lsd=lesion simulating disease). This class of mutants is also referred to as "cim Class I" as disclosed in U.S. patent application Ser. No. 08/648,949, the disclosure of which is hereby incorporated by reference in its entirety. See also, WO 94/16077. This lsd class (aka cim Class I) formed spontaneous lesions on the leaves, accumulated elevated concentrations of SA, high levels of PR-1, PR-2 and PR-5 mRNA and was resistant to fungal and bacterial pathogens (Dietrich et al., 1994; Weymann et al., 1995).

The second class, called cim (cim=constitutive immunity), is described below and has all the characteristics of the lsd mutants except spontaneous lesions. This second class (cim) corresponds to the "cim Class II" mutants discussed in U.S. Pat. No. 5,792,904. See also, WO 94/16077. The cim3 mutant plant line described below falls into this cim class (cim Class II) and is a dominant mutation with wild-type appearance that expresses stable, elevated levels of SA, SAR gene mRNA and has broad spectrum disease resistance.

Example 14

Isolation and Characterization of cim Mutants with Constitutive SAR Gene Expression 1100 individual M2 mutagenized (EMS) Arabidopsis plants were grown in Aracon trays (Lehle Seeds, Round Rock, Tex.) in sets of approximately 100. Plants were grown as described in Uknes et al., 1993, supra, with special attention given to avoid over-watering and pathogen infection. Briefly, Metro Mix 360 was saturated with water and autoclaved three times for 70 minutes in 10-liter batches. The potting mix was stirred thoroughly in between each autoclaving. Seeds were surface sterilized in 20% Clorox for 5 minutes and washed with seven changes of sterile water before sowing. Planted seeds were vernalized for 3–4 days followed by growth in chambers with a 9 hour day and 15 hour night at 22° C. When the plants were three- to four-weeks-old, one or two leaves, weighing 50 to 100 mg, were harvested and total RNA was isolated using a rapid, mini-RNA preparation (Verwoerd et al. (1989) *Nuc. Acid Res.* 17, 2362). PR-1 gene expression was analyzed by Northern blot analysis (Lagrimini et al. (1 987) *Proc. Natl. Acad. Sci. USA* 84, 7542–7546; Ward et al., 1991). Each set of plants also contained a non-treated *A. thaliana* Col-0 and a 2-day INA-treated (0.25 mg/ml) control. All plants were maintained as described in Weymann et al., (1995).

80 putative mutants accumulating elevated levels of PR-1 mRNA were identified. Following progeny testing, five were chosen for further characterization. Putative cim mutants displayed elevated SAR gene expression in the absence of pathogen or inducing treatment. Progeny testing of the putative cim mutants confirmed that constitutive PR-1 expression was heritable. Of the cim mutants, two, cim2 and cim3, with the highest, most stable expression of PR-1 were characterized further.

Back crosses to Columbia utilized the recessive glabrous trait as a marker for identification of F1 progeny. Col-gl1 flower buds were emasculated prior to pollen shed, and pollen from the mutants was applied immediately and the following day. F1 plants were grown in soil and the out crossed plants were identified by the presence of trichomes.

Following crosses of cim2 and cim3 to ecotype Col-0 or La-er, a large proportion of F1 plants were identified with high SAR gene expression, suggesting these traits were dominant. In the case of cim2, some, but not all, F1 plants had constitutive SAR gene expression. Such a result would be expected if the cim2 mutant were dominant and carried as a heterozygote in the parent. Further genetic testing of cim2 showed continued variable segregation in the F2 generation, consistent with incomplete penetrance.

cim3 demonstrated a 1:1 segregation in the F1 generation whereupon two individual F1 plants expressing a high level of PR-1 mRNA were selfed to form an F2 population. F2 segregation, obtained by scoring PR-1 mRNA accumulation, showed 93 F2 plants with high PR-1 mRNA and 25 F2 plants without significant PR-1 mRNA accumulation giving a 3.7:1 ratio ($c^2$=1.77; 0.5>P>0.1), which is consistent with the hypothesis that cim3 is a dominant, single gene mutation. Subsequent outcrosses confirmed that cim3 was inherited as a dominant mutation.

For cim3, the original M2 plant identified in the screen and the M3 population appeared normal. However, as the cim3 plants were selfed some of the best expressing lines had low fertility.

Following the back cross to Col-gl1, plants with normal appearance and fertility and strong PR-1 expression were obtained.

When initially identified, cim3 also appeared slightly dwarfed with thin, distorted leaves. However, F2 plants resulting from a cross with ecotype Col-gl1 retained high SAR gene expression and could not be distinguished from wild-type plants. This suggested that the dwarfed, distorted-leaf leaf phenotype was caused by an independent mutation that was not associated with constitutive SAR gene expression. The cim3 mutant phenotype was also observed when plants were grown in sterile conditions confirming that PR-1 mRNA accumulation was not caused by a pathogen.

Example 15

SAR Gene Expression

In addition to PR-1, two other SAR genes, PR-2 and PR-5, are also highly expressed in cim3. Levels of SAR gene expression varied between the progeny, but were always more than 10-fold higher than the untreated control and similar to the levels obtained following a resistance-inducing INA (0.25 mg/ml) treatment of wild-type plants.

Example 16

Salicylic Acid Analysis

Endogenous concentrations of SA have been shown to increase following pathogen-induced necrosis in Arabidopsis (Uknes et al., 1993, supra). Salicylic acid and its glucose conjugate were analyzed as described in Uknes et al., 1993. Leaf tissue was harvested from 10 cim3 and 10 control, 4 week-old plants. Leaves from individual plants were harvested and analyzed for PR-1 gene expression. SA levels were measured from plants expressing PR-1. The concentration of free SA in cim3 was 3.4-fold higher than in non-infected wild-type Arabidopsis (233±35 vs. 69±8 ng/g fresh weight, respectively). The glucose conjugate of SA (SAG) was 13.1-fold higher in cim3 than in non-infected wild-type Arabidopsis (4519±473 vs. 344±58 ng/g fresh weight, respectively). These increased levels of SA and SAG are comparable to the levels that have been reported for either pathogen-infected tissue or the cpr mutant.

Example 17

Disease Resistance cim3 was evaluated for resistance to *Peronospora parasitica* (NoCo2), the causal agent of downy mildew disease of Arabidopsis. Thirty cim3 (confirmed by PR-1 RNA expression) and thirty control plants (ecotype Columbia), each about 4 weeks old, were inoculated with *P. parasitica*, as described in Uknes, et al. 1992, supra. Seven days later, plants were analyzed for sporulation and stained with trypan blue to visualize fungal structures, as described in Keogh et al. (1980) *Trans. Br. Mycol. Soc.* 74, 329–333, and in Koch and Slusarenko (1990) *Plant Cell* 2, 437–445. Wild-type (Col-0) plants support the growth of hyphae, conidia, and oospores, while wild type plants treated with INA (0.25 mg/ml) and cim3 plants showed no fungal growth. The cim3-mediated resistance is typically seen as a small group of dead cells at the site of pathogen infection. This type of resistance is similar to that seen in lsd mutants (Dietrich et al., 1994, supra; Weymann et al., 1995, supra), or in wild-type plants in which SAR has been induced (Uknes et al., 1992, supra). Occasionally, intermediate resistance phenotypes were observed, including trailing necrosis in the wake of the hyphal tip in cim3 plants. This trailing necrosis is similar to that found in wild-type plants treated with low doses of SA or INA (Uknes et al., 1992, supra; Uknes et al., 1993, supra). However, sporulation was never observed on cim3 plants while all control plants showed sporulation. No spontaneous lesions were observed on uninoculated cim3 leaves when stained with trypan blue.

In addition to resistance to the fungal pathogen *P. parasitica*, cim3 was also resistant to infection with the bacterial pathogen *Pseudomonas syringae* DC3000. Six-week-old wild-type (±INA treatment), and cim3 plants were inoculated with a suspension of *P. syringae* DC3000 and the progress of the disease was followed by monitoring the growth of the bacteria extracted from infected leaves over time. The difference in bacterial titers between Col-O, Col-O+INA and cim3 at either day 0 or day 2 was not statistically significant. However, by day four, there was a 31-fold decrease in bacterial growth between wild-type and cim3 plants (P<0.003; Sokal and Rohlf, 1981). The plants were also visually inspected for disease symptoms. Leaves from wild-type plants were severely chlorotic with disease symptoms spreading well beyond the initial zone of injection. In contrast, either wild-type plants pretreated with INA or cim3 plants were nearly devoid of disease symptoms.

For this example, cultures of *Pseudomonas syringae* pv. tomato strain DC3000 were grown on King's B media (agar plates or liquid) plus rifampicin (50 µg/ml) at 28° C. (Walen et al. (1991) *Plant Cell* 3, 49–59). An overnight culture was diluted and resuspended in 10 mM $MgCl_2$ to a density of $2-5 \times 10^5$ cells per ml and injected into Arabidopsis leaves. Injections were carried out by creating a small hole with a 28 gauge needle midway up the leaf and then injecting approximately 250 µl of the diluted bacterial solution with a 1 cc syringe. At various time points, random samples consisting of 3 random leaf punches from a #1 cork borer were taken from 10 plants from each treatment. The 3 leaf punches were placed in an eppendorf tube with 300 µl of 10 mM $MgCl_2$ and ground with a pestle. The resulting bacterial suspension was appropriately diluted and plated on King's B media plus rifampicin (50 µg/ml) and grown for 4 days at 28° C. Bacterial colonies were counted and the data were subjected to Student's t statistical analysis (Sokal and Rohlf (1981), Biometry, $2^{nd}$ed. New York: W.H. Freeman and Company).

Also for this example, 2,6-Dichloroisonicotinic acid (INA) was suspended in sterile, distilled water as a 25% active ingredient formulated in a wetable powder (0.25 mg/ml, 325 µM; Kessmann et al. (1994) *Annu. Rev. Phytopathol.* 32, 439–59). All plants were sprayed with water or INA solutions to the point of imminent runoff.

Example 18
The Role of SA in SAR Gene Expression and Disease Resistance

To investigate the relationship between SA, SAR gene expression and resistance in cim3, crosses were carried out with Arabidopsis plants expressing the salicylate hydroxylase (nahG) gene (Delaney et al., 1994). These "NahG plants"were made by transformation of the 35S driven nahG gene into Arabidopsis using Agrobacterium-mediated transformation. See, Huang, H. Ma, H. (1992) *Plant Mol. Biol. Rep.* 10, 372–383, herein incorporated by reference; Gaffney, et al. (1993) *Science* 261, 754–756, herein incorporated by reference; and Delaney, et al. (1994) *Science* 266, 1247–1250, herein incorporated by reference. Col-nahG Arabidopsis carries a dominant kanamycin resistance gene in addition to the dominant nahg gene, so Col-nahG was used as the pollen donor. F1 seed was hydrated in water for 30 minutes and then surface sterilized in 10% Clorox, 0.05% Tween 20 for five minutes and washed thoroughly in sterile water. Seeds were plated onto germination media (GM, Murashige and Skoog medium containing 10 g/L sucrose buffered with 0.5 g/L 2-(N-morpholino) ethanesulfonic acid, pH 5.7 with KOH) containing 25 mg/ml kanamycin to select for $F_1$ plants. See Valvekens et al. (1988) *Proc. Natl. Acad. Sci., USA* 85, 5536–5540. Kanamycin resistant $F_1$ plants were transferred to soil after 18 days. The presence of the nahG gene and PR-1 expression was confirmed in all experiments by Northern blot analysis.

Because both the cim3 mutant and nahG phenotypes are dominant, epistasis between the two genes could be analyzed in F1 plants. Seventy F1 plants from a cim3 X nahG cross were analyzed for PR-1 and nahG gene expression. In Northern blot analysis of mRNA expression, the presence of the nahG gene correlated with suppressed SAR gene expression. The presence of cim3 in each F1 was confirmed by assessing PR-1 mRNA in the resulting F2 segregants.

To determine if the cim3 mutation was epistatic to nahG with respect to disease resistance, 5 F1 plants from the cim3 X nahG cross, which had been confirmed for the presence of nahG and absence of PR-1 mRNA, were selfed and 20–30 F2 seed were planted. Expression of nahG and PR-1 mRNA was analyzed in individuals from this F2 population, which were then challanged with *P. parasitica* (NoCo2) to assess their disease susceptibility. Disease resistance conferred by cim3 was eliminated by the presence of the nahG gene, demonstrating that nahG is epistatic to cim3 for the SAR gene expression and disease resistance phenotypes.

Example 19
Synergistic Disease-Resistance Attained by Applying Microbicide and/or BTH to cim Mutants Three days before pathogen inoculation, the chemical inducer of systemic acquired resistance BTH (benzo(1,2,3) thiadiazole-7-carbothioic acid S-methyl ester) formulated as 25% active ingredient (ai) with a wettable powder carrier (Metraux et al., 1991) and/or the microbicide metalaxyl (CGA 48988XX) formulated as 25% ai, or the wettable powder alone was applied as a fine mist to leaves of 4 week-old plants. Plants were inoculated with a conidial suspension ($1.8 \times 10^5$ spores/ml) of the compatible pathogen *Peronospora parasitica* NoCo2. Following inoculation, plants were covered to maintain high humidity and were placed in a Percival growth chamber at 17° C. with a 14-hr day/10-hr night cycle (Uknes et al., 1993). Tissue was harvested 8 days after inoculation.

Fungal growth was determined using a rRNA fungal probe that was obtained by PCR according to White et al. (1990; PCR Protocols: A guide to Methods and Application, 315–322) using primers NS1 and NS2 and *P. parasitica* EmWa DNA as templates. RNA was purified from frozen tissue by phenol/chloroform extraction following lithium chloride precipitation (Lagrimini et al, 1987: PNAS, 84: 7542–7546). Samples (7.5 µg) were separated by electrophoresis through formaldehyde agarose gels and blotted to nylon membranes (Hybond-N+, Amersham) as described by Ausbel et al. (1987). Hybridizations and washing were according to Church and Gilbert (1984, *PNAS*, 81: 1991–1995). Relative amounts of the transcript were determined using a Phosphor Imager (Molecular Dynamics, Sunnyvale, Calif.) following manufacturers instructions. Sample loading was normalized by probing stripped filter blots with the constitutively expressed b-tubulin Arabidopsis cDNA. The infestation of the untreated plants corresponded to 0% fungal growth inhibition.

Application of metalaxyl alone, the "plant activator" BTH alone, or both metalaxyl and BTH to the cim3 mutants described above produced a greater-than-additive, i.e., synergistic, disease-resistant effect. This effect was determined as the synergy factor (SF), which is the ratio of observed (O) effect to expected (E) effect. The following results were obtained:

TABLE 33

Action Against *Peronospora parasitica* In Arabidopsis
Component I: cim3 mutation
Component II: metalaxyl

| | Components | | Fungal Growth Inhibition % | | Synergy Factor |
|---|---|---|---|---|---|
| Test no. | cim3 | metalaxyl | O (observed) | E (expected) | O/E |
| control | wt | — | 0 | | |
| 1 | cim3 | — | 12.5 | | |
| 2 | wt | 12.5 mg/l | 52.7 | | |
| 3 | wt | 2.5 mg/l | 0 | | |
| 4 | wt | 0.1 mg/l | 0 | | |
| 5 | wt | 0.02 mg/l | ND | | |
| 6 | cim3 | 12.5 mg/l | ND | ND | ND |
| 7 | cim3 | 2.5 mg/l | 82.2 | 12.5 | 6.6 |
| 8 | cim3 | 0.1 mg/l | 57.8 | 12.5 | 4.6 |
| 9 | cim3 | 0.02 mg/l | 55.6 | ND | ND | wt = wild-type Col-0
ND = not determined

TABLE 34

Action Against *Peronospora parasitica* In Arabidopsis
Component I: cim3 mutation
Component II: BTH

| | Components | | Fungal Growth Inhibition % | | Synergy Factor |
|---|---|---|---|---|---|
| Test no. | cim3 | BTH | O (observed) | E (expected) | O/E |
| control | wt | — | 0 | | |
| 1 | cim3 | — | 12.5 | | |
| 2 | wt | 0.1 mM | 85.7 | | |
| 3 | wt | 0.03 mM | 20.8 | | |
| 4 | wt | 0.01 mM | 0 | | |
| 5 | cim3 | 0.1 mM | ND | 98.2 | ND |
| 6 | cim3 | 0.03 mM | 73.1 | 33.3 | 2.2 |
| 7 | cim3 | 0.01 mM | 16.6 | 12.5 | 1.3 | wt = wild-type Col-0
ND = not determined

TABLE 35

Action Against *Peronospora parasitica* In Arabidopsis
Component I: cim3 mutation
Component II: BTH and metalaxyl (M)

| | Components | Fungal Growth Inhibition % | | Synergy Factor |
|---|---|---|---|---|
| Test no. | cim3 | BTH + M | O (observed) E (expected) | | O/E |
| control | wt | — | 0 | | |
| 1 | cim3 | — | 12.5 | | |
| 2 | wt | BTH 0.01 mM + M 0.5 mg/l | 100 | | |
| 3 | wt | BTH 0.01 mM + M 0.1 mg/l | 40.7 | | |
| 4 | wt | BTH 0.01 mM + M 0.02 mg/l | ND | | |
| 5 | cim3 | BTH 0.01 mM + M 0.5 mg/l | ND | 100 | ND |
| 6 | cim3 | BTH 0.01 mM + M 0.1 mg/l | 100 | 53.2 | 19 |

TABLE 35-continued

Action Against *Peronospora parasitica* In Arabidopsis
Component I: cim3 mutation
Component II: BTH and metalaxyl (M)

| | Components | Fungal Growth Inhibition % | | Synergy Factor |
|---|---|---|---|---|
| Test no. | cim3 | BTH + M | O (observed) E (expected) | | O/E |
| 7 | cim3 | BTH 0.01 mM + M 0.02 mg/l | 77.7 | ND | ND | wt = wild-type Col-0
ND = not determined

As can be seen from the above tables, synergistic disease-resistant effects were demonstrated in the cim3 plants by application of metalaxyl alone, by application of BTH alone, and by application of metalaxyl and BTH in combination. For example, in the untreated cim3 plant, 12.5% fungal growth inhibition was seen relative to the untreated wild-type plant; this demonstrates that the constitutive SAR gene expression in the cim3 mutant correlates with disease resistance. As shown in Table 30, however, by applying metalaxyl at 0.0001 g/l (a concentration normally insufficient for efficacy) to the immunomodulated (SAR-on) cim3 plant, the observed level of fungal growth inhibition increased to 57.8%. The synergy factor of 4.6 calculated from these data clearly demonstrates the synergistic effect achieved by applying a microbicide to an immunomodulated plant.

The data presented in Table 31 demonstrates that synergy is also achieved by applying a chemical inducer of systemic acquired resistance such as BTH to an immunomodulated (SAR-on) cim3 plant. For example, in wild-type plants, a 0.03 mM concentration of BTH is normally insufficient to confer effective disease resistance, providing only 20.8% fungal growth inhibition. However, in cim3 plants, this normally inadequate concentration of BTH provided 73.1% fungal growth inhibition, which was nearly as high as the level of inhibition provided by 0.1 mM BTH, the recommended concentration for efficacy. The synergy factor of 2.2 calculated from the data in Table 31 clearly demonstrates the synergistic effect achieved by applying BTH to a plant that is already immunomodulated through other means.

The effects on disease resistance were even more dramatic when both BTH and metalaxyl were applied to the cim3 plant. As set forth above in Example 13 (Table 29), in wild-type plants, no fungal growth inhibition is achieved by separately applying either 0.01 mM BTH or 0.0001 g/l metalaxyl, because these concentrations are normally insufficient for efficacy. However, by applying both of these compounds to the plants at these normally insufficient concentrations, 40.7% fungal growth inhibition was observed, which is a synergistic effect with respect to the wild-type plants. In the cim3 plants, the simultaneous application of 0.01 mM BTH and 0.0001 g/, metalaxyl resulted in 100% fungal growth inhibition, clearly demonstrating even further synergistic activity.

Thus, the combined use of of immunomodulated cim plants with low, normally ineffective concentrations of chemicals to achieve disease resistance provide advantages that should be apparent to those skilled in the agricultural arts. Normally toxic or otherwise undesirable concentrations of chemicals can be avoided by taking advantage of the synergies demonstrated herein. In addition, economic gains can be realized as a result of the decreased quantity of chemicals required to provide a given level of protection to plants.

III. Synergistic Disease Resistance Effects Achieved by Application of Conventional Microbicides and/or Chemical Inducers of Systemic Acquired Resistance To Transgenic Plants Containing Forms of the NIM1 Gene The NIM1 gene is a key component of the systemic acquired resistance (SAR) pathway in plants (Ryals et al.,1996). The NIM1 gene is associated with the activation of SAR by chemical and biological inducers and, in conjunction with such inducers, is required for SAR and SAR gene expression. The location of the NIM1 gene has been determined by molecular biological analysis of the genome of mutant plants known to carry the mutant nim1 gene, which gives the host plants extreme sensitivity to a wide variety of pathogens and renders them unable to respond to pathogens and chemical inducers of SAR. The wildtype NIM1 gene of Arapidopsis has been mapped and sequenced (SEQ ID NO:1). The wild-type NIM1 gene product (SEQ ID NO:2) is involved in the signal transduction cascade leading to both SAR and gene-for-gene disease resistance in Arabidopsis (Ryals et al., 1997). Recombinant overexpression of the wild-type form of NIM1 gives rise to immunomodulated plants with a constitutive immunity (CIM) phenotype and therefore confers disease resistance in transgenic plants. Increased levels of the active NIM1 protein produce the same disease-resistance effect as chemical induction with inducing chemicals such as BTH, INA, and SA. See, co-pending U.S. application Ser. No. 08/880,179, incorporated herein by reference, and co-pending International PCT Application No. PCT/EP97/07012 (WO 98/26082), incorporated herein by reference.

Furthermore, the NIM1 gene product has been shown to be a structural homologue of the mammalian signal transduction factor IκB subclass α (Ryals et al., 1997). Mutations of IκB have been described that act as super-repressors or dominant-negatives of the NF-κB/IκB regulation scheme. Thus, certain altered forms of NIM1 act as dominant-negative regulators of the SAR signal transduction pathway. These altered forms of NIM1 confer the opposite phenotype in plants transformed therewith as the nim1 mutant; i.e., immunomodulated plants transformed with altered forms of NIM1 exhibit constitutive SAR gene expression and a CIM phenotype. See, co-pending U.S. application Ser. No. 08/989,478, incorporated herein by reference.

Example 20
Transformation of Plants with Cosmid Clones Containing the Wild-type NIM1 Gene Cosmid D7 (deposited with the ATCC on Sep. 25, 1996, as ATCC 97736) was generated from a clone spanning the NIM1 gene region and therefore includes the wild-type NIM1 gene (SEQ ID NO:1). Cosmid E1 was also generated from a clone spanning the NIM1 gene region and therefore also includes the wild-type NIM1 gene (SEQ ID NO:1). Cosmids D7 and E1 were moved into Agrobacterium tumefaciens AGL-1 through conjugative transfer in a tri-parental mating with helper strain HB101 (pRK2013) as described in the U.S. patent application Ser. No. 08/880,179. These cosmids were then used to transform a kanamycin-sensitive nim1 mutant Arabidopsis line using vacuum infiltration (Mindrinos et al., 1994, Cell 78, 1089–1099). Seed from the infiltrated plants was harvested and allowed to germinate on GM agar plates containing 50 mg/ml kanamycin as a selection agent. Seedlings that survived the selection were transferred to soil approximately two weeks after plating.

Plants transferred to soil were grown in a phytotron for approximately one week after transfer. 300 mM INA was applied as a fine mist to completely cover the plants using a chromister. After two days, leaves were harvested for RNA extraction and PR-1 expression analysis. The plants were then sprayed with *Peronospora parasitica* (isolate EmWa) and grown under high humidity conditions in a growing chamber with 19° C. day/17° C. night temperatures and 8 h light/16 h dark cycles. Eight to ten days following fungal infection, plants were evaluated and scored positive or negative for fungal growth. Ws and nim1 plants were treated in the same way to serve as controls for each experiment.

Total RNA was extracted from the collected tissue using a LiCl/phenol extraction buffer (Verwoerd et al., 1989, Nuc Acid Res, 2362). RNA samples were run on a formaldehyde agarose gel and blotted to GeneScreen Plus (DuPont) membranes. Blots were hybridized with a $^{32}$P-labeled PR-1 cDNA probe. The resulting blots were exposed to film to determine which transformants were able to induce PR-1 expression after INA treatment.

To see if any of the D7 and E1 transformants overexpressed NIM1 due to insertion site (position) effect, primary transformants containing the D7 or E1 cosmids were selfed and the T2 seed collected. Seeds from one E1 line and 95 D7 lines were sown on soil and grown as described above. When the T2 plants had obtained at least four true leaves, a single leaf was harvested separately for each plant. RNA was extracted from this tissue and analyzed for PR-1 and NIM1 expression. Plants were then inoculated with *P. parasitica* (EmWa) and analyzed for fungal growth at 10 days following infection. A number of transformants showed less than normal fungal growth and four of them, namely, lines D7-2, D7-74, D7-89 and E1-1, showed no visible fungal growth at all. Plants showing higher than normal NIM1 and PR-1 expression and displaying fungal resistance demonstrate that overexpression of NIM1 confers disease resistance.

Example 21
NIM1 Overexpression Under its Native Promoter

Plants constitutively expressing the NIM1 gene were generated from transformation of Ws wild type plants with the BamHI-HindIII NIM1 genomic fragment (SEQ ID NO: 1—bases 1249–5655) containing 1.4 kb of promoter sequence. This fragment was cloned into pSGCG01 and transformed into the Agrobacterium strain GV3101 (pMP90, Koncz and Schell (1986) *Mol. Gen. Genet.* 204: 383–396). Ws plants were infiltrated as previously described. The resulting seed was harvested and plated on GM agar containing 50 μg/ml kanamycin. Surviving plantlets were transferred to soil and tested as described above for resistance to *Peronospora parasitica* isolate Emwa. Selected plants were selfed and selected for two subsequent generations to generate homozygous lines. Seeds from several of these lines were sown in soil and 15–18 plants per line were grown for three weeks and tested again for Emwa resistance without any prior treatment with an inducing chemical. Approximately 24 hours, 48 hours, and five days after fungal treatment, tissue was harvested, pooled and frozen for each line. Plants remained in the growth chamber until ten days after inoculation when they were scored for resistance to Emwa.

RNA was prepared from all of the collected samples and analyzed as previously described (Delaney et al, 1995). The blot was hybridized to the Arabidopsis gene probe PR-1 (Uknes et al, 1992). Five of the 13 transgenic lines analyzed showed early induction of PR1 gene expression. For these lines, PR-1 mRNA was evident by 24 or 48 hours following fungal treatment. These five lines also had no visible fungal growth. Leaves were stained with lactophenol blue as described (Dietrich et al., 1994) to verify the absence of fungal hyphae in the leaves. PR-1 gene expression was not induced in the other eight lines by 48 hours and these plants did not show resistance to Emwa.

A subset of the resistant lines were also tested for increased resistance to the bacterial pathogen *Pseudomonas syringae* DC3000 to evaluate the spectrum of resistance evident as described by Uknes et al. (1993). Experiments were done essentially as described by Lawton et al. (1996). Bacterial growth was slower in those lines that also demonstrated constitutive resistance to Emwa. This shows that plants overexpressing the NIM1 gene under its native promoter have constitutive immunity against pathogens.

To assess additional characteristics of the CIM phenotype in these lines, unifected plants are evaluated for free and glucose-conjugated salicylic acid and leaves are stained with lactophenol blue to evaluate for the presence of microscopic lesions. Resistance plants are sexually crossed with SAR mutants such as NahG and ndr1 to establish the epistatic relationship of the resistance phenotype to other mutants and evaluate how these dominant negative mutants of NIM1 may influence the salicylic acid-dependent feedback loop.

Example 22
35S Driven Overexpression of NIM1

The full-length NIM1 cDNA (SEQ ID NO: 6) was cloned into the EcoRI site of pCGN1761 ENX (Comai et al. (1990) *Plant Mol. Biol.* 15, 373–381). From the resulting plasmid, an XbaI fragment containing an enhanced CaMV 35S promoter, the NIM1 cDNA in the correct orientation for transcription, and a tml 3' terminator was obtained. This fragment was cloned into the binary vector pCIB200 and transformed into GV3101. Ws plants were infiltrated as previously described. The resulting seed was harvested and plated on GM agar containing 50 μg/ml kanamycin. Surviving plantlets were transferred to soil and tested as described above. Selected plants were selfed and selected for two subsequent generations to generate homozygous lines. Nine of the 58 lines tested demonstrated resistance when they were treated with Emwa without prior chemical treatment. Thus, overexpression of the NIM1 cDNA also results in disease-resistant plants.

Example 23
NIM1 Is A Homolog of IκBα

A multiple sequence alignment between the protein gene products of NIM1 and IkB was performed by which it was determined that the NIM1 gene product is a homolog of IκBα (FIGS. 1A and 1B). Sequence homology searches were performed using BLAST (Altschul et al., *J. Mol. Biol.* 215, 403–410 (1990)). The multiple sequence alignment was constructed using Clustal V (Higgins et al., *CABIOS* 5,151–153 (1989)) as part of the Lasergene Biocomputing Software package from DNASTAR (Madison, Wis.). The sequences used in the alignment were NIM1 (SEQ ID NO:2), mouse IκBα (SEQ ID NO:3, GenBank Accession #:1022734), rat IκBα (SEQ ID NO:4, GenBank accession Nos. 57674 and X63594; Tewari et al., *Nucleic Acids Res.* 20, 607 (1992)), and pig IκBα (SEQ ID NO:5, GenBank accession No. Z21968; de Martin et al., *EMBO J.* 12, 2773–2779 (1993); GenBank accession No. 517193, de Martin et al., *Gene* 152, 253–255 (1995)). Parameters used in the Clustal analysis were gap penalty of 10 and gap length penalty of 10. Evolutionary divergence distances were calculated using the PAM250 weight table (Dayhoff et al., "A model of evolutionary change in proteins. Matrices for detecting distant relationships." In *Atlas of Protein Sequence and Structure*, Vol. 5, Suppl. 3, M. O., Dayhoff, ed (National Biomedical Research Foundation, Washington, D.C.), pp. 345–358 (1978)). Residue similarity was calculated using a modified Dayhoff table (Schwartz and Dayhoff, "A model of evolutionary change in proteins." In *Atlas of Protein Sequence and Structure*, M. O. Dayhoff, ed (National Biomedical Research Foundation, Washington, D.C.) pp. 353–358 (1979); Gribskov and Burgess, *Nucleic Acids Res.* 14, 6745–6763 (1986)).

Homology searches indicate similarity of NIM1 to ankyrin domains of several proteins including: ankyrin, NF-κB and IκB. The best overall homology is to IκB and related molecules (FIGS. 1A and 1B). NIM1 contains 2 serines at amino acid positions 55 and 59; the serine at position 59 is in a context (D/ExxxxS) and position (N-terminal) consistent with a role in phosphorylation-dependent, ubiquitin-mediated, inducible degradation. All IκBα's have these N-terminal serines and they are required for inactivation of IκB and subsequent release of NF-κB. NIM1 has ankyrin domains (amino acids 262–290 and 323–371). Ankyrin domains are believed to be involved in protein-protein interactions and are a ubiquitous feature for IκB and NF-κB molecules. The C-termini of IκB's can be dissimilar. NIM1 has some homology to a QL-rich region (amino acids 491–499) found in the C-termini of some IκBs.

Example 24
Generation of Altered Forms of NIM1—Changes of Serine Residues 55 and 59 to Alanine Residues Phosphorylation of serine residues in human IκBα is required for stimulus-activated degradation of IκBα thereby activating NF-κB. Mutagenesis of the serine residues (S32–S36) in human IκBα to alanine residues inhibits stimulus-induced phosphorylation thus blocking IκBα proteosome-mediated degradation (E. Britta-Mareen Traenckner et al., *EMBO J.* 14: 2876–2883 (1995); Brown et al., *Science* 267: 1485–1488 (1996); Brockman et al., *Molecular and Cellular Biology* 15: 2809–2818 (1995); Wang et al., *Science* 274: 784–787 (1996)).

This altered form of IκBα functions as a dominant negative form by retaining NF-κB in the cytoplasm, thereby blocking downstream signaling events. Based on sequence comparisons between NIM1 and I-κB, serines 55 (S55) and 59 (S59) of NIM1 are homologous to S32 and S36 in human IκBα. To construct dominant-negative forms of NIM1, the serines at amino acid positions 55 and 59 are mutagenized to alanine residues. This can be done by any method known to those skilled in the art, such as, for example, by using the QuikChange Site Directed Mutagenesis Kit (#200518:Strategene).

Using a full length NIM1 cDNA (SEQ ID NO:6) including 42 bp of 5' untranslated sequence (UTR) and 187 bp of 3' UTR, the mutagenized construct can be made per the manufacturer's instructions using the following primers (SEQ ID NO:6, positions 192–226): 5'-CAA CAG CTT CGA AGC CGT CTT TGA CGC GCC GGA TG-3' (SEQ ID NO:25) and 5'-CAT CCG GCG CGT CAA AGA CGG CTT CGA AGC TGT TG-3' (SEQ ID NO:26), where the underlined bases denote the mutations. The strategy is as follows: The NIM1 cDNA cloned into vector pSE936 (Elledge et al., *Proc. Nat. Acad. Sci. USA* 88: 1731–1735 (1991)) is denatured and the primers containing the altered bases are annealed. DNA polymerase (Pfu) extends the primers by nonstrand-displacement resulting in nicked circular strands. DNA is subjected to restriction endonuclease digestion with DpnI, which only cuts methylated sites (nonmutagenized template DNA). The remaining circular dsDNA is transformed into *E.coli* strain XL1-Blue. Plasmids from resulting colonies are extracted and sequenced to verify the presence of the mutated bases and to confirm that no other mutations occurred.

The mutagenized NIM1 cDNA is digested with the restriction endonuclease EcoRI and cloned into pCGN1761 under the transcriptional regulation of the double 35S promoter of the cauliflower mosaic virus. The transformation cassette including the 35S promoter, NIM1 cDNA and tml terminator is released from pCGN 1761 by partial restriction digestion with XbaI and ligated into the XbaI and ligated into the XbaI site of dephosphorylated pCIB200. SEQ ID NO's:7 and 8 show the DNA coding sequence and encoded amino acid sequence, respectively, of this altered form of the NIM1 gene.

Example 25
Generation of Altered Forms of NIM1—N-terminal Deletion

Deletion of amino acids 1–36 (Brockman et al.; Sun et al.) or 1–72 (Sun et al.) of human IκBα, which includes K21, K22, S32 and S36, results in a dominant-negative IκBα phenotype in transfected human cell cultures. An N-terminal deletion of approximately the first 125 amino acids of the encoded product of the NIM1 cDNA removes eight lysine residues that may serve as potential ubiquitination sites and also removes putative phosphorylation sites at S55 and S59 (see Example 2). This altered gene construct may be produced by any means known to those skilled in the art. For example, using the method of Ho et al., Gene 77: 51–59 (1989), a NIM1 form may be generated in which DNA encoding approximately the first 125 amino acids is deleted. The following primers produce a 1612-bp PCR product (SEQ ID NO:6: 418 to 2011): 5'-gg aat tca-<u>ATG</u>GAT TCG GTT GTG ACT GTT TTG-3' (SEQ ID NO:27) and 5'-gga att cTA CAA ATC TGT ATA CCA TTG G-3' (SEQ ID NO:28) in which the synthetic start codon is underlined (<u>ATG</u>) and EcoRI linker sequence is in lower case. Amplification of fragments utilizes a reaction mixture comprising 0.1 to 100 ng of template DNA, 10 mM Tris pH 8.3/50 mM KCl/2 mM $MgCl_2$/0.001% gelatin/0.25 mM each dNTP/0.2 mM of each primer and 1 unit rTth DNA polymerase in a final volume of 50 mL and a Perkin Elmer Cetus 9600 PCR machine. PCR conditions are as follows: 94° C. 3 min: 35×(94° C. 30 sec: 52° C. 1 min: 72° C. 10 min. The PCR product is cloned directly into the pCR2.1 vector (Invitrogen). The PCR-generated insert in the PCR vector is released by restriction endonuclease digestion using EcoRI and ligated into the EcoRI site of dephosphorylated pCGN1761, under the transcriptional regulation of the double 35S promoter. The construct is sequenced to verify the presence of the synthetic starting ATG and to confirm that no other mutations occurred during PCR. The transformation cassette including the 35S promoter, modified NIM1 cDNA and tml terminator is released from pCGN 1761 by partial restriction digestion with XbaI and ligated into the XbaI site of pCIB200. SEQ ID NO's:9 and 10 show the DNA coding sequence and encoded amino acid sequence, respectively, of an altered form of the NIM1 gene having an N-terminal amino acid deletion.

Example 26
Generation of Altered Forms of NIM1—C-terminal Deletion

The deletion of amino acids 261–317 of human IκBα is believed to result in enhanced intrinsic stability by blocking the constitutive phosphorylation of serine and threonine residues in the C-terminus. A region rich in serine and threonine is present at amino acids 522–593 in the C-terminus of NIM1. The C-terminal coding region of the NIM1 gene may be modified by deleting the nucleotide sequences which encode amino acids 522–593. Using the method of Ho et al. (1989), the C-terminal coding region and 3' UTR of the NIM1 cDNA (SEQ ID NO:6: 1606–2011) is deleted by PCR, generating a 1623 bp fragment using the following primers: 5'-cggaattcGATCTCTTTAATTTGTGAATTT C-3' (SEQ ID NO:29) and 5'-ggaattc<u>TCA</u>ACAGTT CATAATCTGGTCG-3' (SEQ ID NO:30) in which a synthetic stop codon is underlined (TGA on complementary strand) and EcoRI linker sequences are in lower case. PCR reaction components are as previously described and cycling parameters are as follows: 94° C. 3 min: 35×(94° C. 30 sec: 52° C. 30 sec: 72° C. 2 min); 72° C. 10 min]. The PCR product is cloned directly into the pCR2.1 vector (Invitrogen). The PCR-generated insert in the PCR vector is released by restriction endonuclease digestion using EcoRI and ligated into the EcoRI site of dephosphorylated pCGN1761, which contains the double 35S promoter. The construct is sequenced to verify the presence of the synthetic in-frame stop codon and to confirm that no other mutations occurred during PCR. The transformation cassette including the promoter, modified NIM1 cDNA, and tml terminator is released from pCGN1761 by partial restriction digestion with XbaI and ligated into the XbaI site of dephosphorylated pCIB200. SEQ ID NO's: 11 and 12 show the DNA coding sequence and encoded amino acid sequence, respectively, of an altered form of the NIM1 gene having a C-terminal amino acid deletion.

Example 27
Generation of Altered Forms of NIM1—N-terminal/C-terminal Deletion Chimera An N-terminal and C-terminal deletion form of NIM1 is generated using a unique KpnI restriction site at position 819 (SEQ ID NO:6). The N-terminal deletion form (Example 25) is restriction endonuclease digested with EcoRI/KpnI and the 415 bp fragment corresponding to the modified N-terminus is recovered by gel electrophoresis. Likewise, the C-terminal deletion form (Example 26) is restriction endonuclease digested with EcoRI/KpnI and the 790 bp fragment corresponding to the modified C-terminus is recovered by gel electrophoresis. The fragments are ligated at 15° C., digested with EcoRI to eliminate EcoRI concatemers and cloned into the EcoRI site of dephosphorylated pCGN 1761. The N/C-terminal deletion form of NIM1 is under the transcriptional regulation of the double 35S promoter. Similarly, a chimeric form of NIM1 is generated which consists of the S55/S59 mutagenized putative phosphorylation sites (Example 24) fused to the C-terminal deletion (Example 26). The construct is generated as described above. The constructs are sequenced to verify the fidelity of the start and stop codons and to confirm that no mutations occurred during cloning. The respective transformation cassettes including the 35S promoter, NIM1 chimera and tml terminator are released from pCGN1761 by partial restriction digestion with XbaI and ligated into the XbaI site of dephosphorylated pCIB200. SEQ ID NO's:13 and 14 show the DNA coding sequence and encoded amino acid sequence, respectively, of an altered form of the NIM1 gene having both N-terminal and C-terminal amino acid deletions.

Example 28
Generation of Altered Forms of NIM1—Ankyrin Domains

NIM1 exhibits homology to ankyrin motifs at approximately amino acids 103–362. Using the method of Ho et al. (1989), the DNA sequence encoding the putative ankyrin domains (SEQ ID NO:1: 3093–3951) is PCR amplified (conditions: 94° C. 3 min:35×(94° C. 30 sec: 62° C. sec: 72°

C. 2 min): 72° C. 10 min) from the NIM1 cDNA (SEQ ID NO:6: 349–1128) using the following primers: 5'-ggaattca ATGGACTCCAACAACACCGCCGC-3' (SEQ ID NO:31) and 5'-ggaattcTCAACCTTCCAAAGTTGCTTCTGATG-3' (SEQ ID NO:32). The resulting product is restriction endonuclease digested with EcoRI and then spliced into the EcoRI site of dephosphorylated pCGN1761 under the transcriptional regulation of the double 35S promoter. The construct is sequenced to verify the presence of the synthetic start codon (ATG), an in-frame stop codon (TGA) and to confirm that no other mutations occurred during PCR. The transformation cassette including the 35S promoter, ankyrin domains, and tml terminator is released from pCGN 1761 by partial restriction digestion with XbaI and ligated into the XbaI site of dephosphorylated pCIB200. SEQ ID NO's: 15 and 16 show the DNA coding sequence and encoded amino acid sequence, respectively, of the ankyrin domain of NIM1.

Example 29
Construction of Chimeric Genes

To increase the likelihood of appropriate spatial and temporal expression of altered NIM1 forms, a 4407 bp HindIII/BamHI fragment (SEQ ID NO:1: bases 1249–5655) and/or a 5655 bp EcoRV/BamHI fragment (SEQ ID NO:1: bases 1–5655) containing the NIM1 promoter and gene is used for the creation of the altered NIM1 forms in Examples 24–28 above. Although the construction steps may differ, the concepts are comparable to the examples previously described herein. Strong overexpression of the altered forms may potentially be lethal. Therefore, the altered forms of the NIM1 gene described in Examples 24–28 may be placed under the regulation of promoters other than the endogenous NIM1 promoter, including but not limited to the nos promoter or small subunit of Rubisco promoter. Likewise, the altered NIM1 forms may be expressed under the regulation of the pathogen-responsive promoter PR-1 (U.S. Pat. No. 5,614,395). Such expression permits strong expression of the altered NIM1 forms only under pathogen attack or other SAR-activating conditions. Furthermore, disease resistance may be evident in the transformants expressing altered NIM1 forms under PR-1 promoter regulation when treated with concentrations of SAR activator compounds (i.e., BTH or INA) which normally do not activate SAR, thereby activating a feedback loop (Weymann et al., (1995) Plant Cell 7: 2013–2022).

Example 30
Transformation of Altered Forms of The NIM1 Into *Arabidopsis thaliana*

The constructs generated (Examples 24–29) are moved into *Agrobacterium tumefaciens* by electroporation into strain GV3101. These constructs are used to transform Arabidopsis ecotypes Col-0 and Ws-0 by vacuum infiltration (Mindrinos et al., *Cell* 78, 1089–1099 (1994)) or by standard root transformation. Seed from these plants is harvested and allowed to germinate on agar plates with kanamycin (or another appropriate antibiotic) as selection agent. Only plantlets that are transformed can detoxify the selection agent and survive. Seedlings that survive the selection are transferred to soil and tested for a CIM (constitutive immunity) phenotype. Plants are evaluated for observable phenotypic differences compared to wild type plants.

Example 31
Assessment of CIM Phenotype in Plants Transformed with the Wild-type NIM1 Gene or an Altered Form of the NIM1 Gene A leaf from each primary transformant is harvested, RNA is isolated (Verwoerd et al., 1989, Nuc Acid Res, 2362) and tested for constitutive PR-1 expression by RNA blot analysis (Uknes et al., 1992). Each transformant is evaluated for an enhanced disease resistance response indicative of constitutive SAR expression analysis (Uknes et al., 1992). Conidial suspensions of $5-10 \times 10^4$ spores/ml from two compatible *P. parasitica* isolates, Emwa and Noco (i.e. these fungal strains cause disease on wildtype Ws-O and Col-0 plants, respectively), are prepared, and transformants are sprayed with the appropriate isolate depending on the ecotype of the transformant. Inoculated plants are incubated under high humidity for 7 days. Plants are disease rated at day 7 and a single leaf is harvested for RNA blot analysis utilizing a probe which provides a means to measure fungal infection.

Transformants that exhibit a CIM phenotype are taken to the T1 generation and homozygous plants are identified. Transformants are subjected to a battery of disease resistance tests as described below. Fungal infection with Noco and Emwa is repeated and leaves are stained with lactophenol blue to identify the presence of fungal hyphae as described in Dietrich et al., (1994). Transformants are infected with the bacterial pathogen *Pseudomonas syringae* DC3000 to evaluate the spectrum of resistance evident as described in Uknes et al. (1993). Uninfected plants are evaluated for both free and glucose-conjugated SA and leaves are stained with lactophenol blue to evaluate for the presence of microscopic lesions. Resistant plants are sexually crossed with SAR mutants such as NahG (U.S. Pat. No. 5,614,395) and ndr1 to establish the epistatic relationship of the resistance phenotype to other mutants and evaluate how these dominant-negative mutants of NIM1 may influence the SA-dependent feedback loop.

Example 32
Isolation of NIM1 Homologs

NIM1 homologs are obtainable that hybridize under moderately stringent conditions either to the entire NIM1 gene from Arabidopsis or, preferably, to an oligonucleotide probe derived from the Arabidopsis NIM1 gene that comprises a contiguous portion of its coding sequence at least approximately 10 nucleotides in length. Factors that affect the stability of hybrids determine the stringency of the hybridization. One such factor is the melting temperature $T_m$, which can be easily calculated according to the formula provided in DNA PROBES, George H. Keller and Mark M. Manak, Macmillan Publishers Ltd, 1993, Section one: Molecular Hybridization Technology; page 8 ff. The preferred hybridization temperature is in the range of about 25° C. below the calculated melting temperature $T_m$, preferably in the range of about 12–15° C. below the calculated melting temperature $T_m$, and, in the case of oligonucleotides, in the range of about 5–10° C. below the melting temperature $T_m$.

Using the NIM1 cDNA (SEQ ID NO:6) as a probe, homologs of Arabidopsis NIM1 are identified through screening genomic or cDNA libraries from different crops such as, but not limited to those listed below in Example 33. Standard techniques for accomplishing this include hybridization screening of plated DNA libraries (either plaques or colonies; see, e.g. Sambrook et al., *Molecular Cloning*, eds., Cold Spring Harbor Laboratory Press. (1989)) and amplification by PCR using oligonucleotide primers (see, e.g. Innis et al., *PCR Protocols, a Guide to Methods and Applications* eds., Academic Press (1990)). Homologs identified are genetically engineered into the expression vectors herein and transformed into the above listed crops. Transformants are evaluated for enhanced disease resistance using relevant pathogens of the crop plant being tested.

NIM1 homologs in the genomes of cucumber, tomato, tobacco, maize, wheat and barley have been detected by DNA blot analysis. Genomic DNA was isolated from cucumber, tomato, tobacco, maize, wheat and barley, restriction digested with the enzymes BamHI, HindIII, XbaI, or SalI, electrophoretically separated on 0.8% agarose gels and transferred to nylon membrane by capillary blotting. Following UV-crosslinking to affix the DNA, the membrane was hybridized under low stringency conditions [(1% BSA; 520 mM NaPO$_4$, pH7.2; 7% lauryl sulfate, sodium salt; 1 mM EDTA; 250 mM sodium chloride) at 55° C. for 18–24 h] with $^{32}$P-radiolabelled *Arabidopsis thaliana* NIM1 cDNA. Following hybridization the blots were washed under low stringency conditions [6×SSC for 15 min. (X3) 3×SSC for 15 min. (X1) at 55° C.; 1×SSC is 0.15M NaCl, 15 mM Na-citrate (pH7.0)] and exposed to X-ray film to visualize bands that correspond to NIM1.

In addition, expressed sequence tags (EST) identified with similarity to the NIM1 gene can be used to isolate homologues. For example, several rice expressed sequence tags (ESTs) have been identified with similarity to the NIM1 gene. A multiple sequence alignment was constructed using Clustal V (Higgins, Desmond G. and Paul M. Sharp (1989), Fast and sensitive multiple sequence alignments on a microcomputer, *CABIOS* 5:151–153) as part of the DNA* (1228 South Park Street, Madison, Wis., 53715) Lasergene Biocomputing Software package for the Macintosh (1994). Certain regions of the NIM1 protein are homologous in amino acid sequence to 4 different rice cDNA protein products. The homologies were identified using the NIM1 sequences in a GenBank BLAST search. Comparisons of the regions of homology in NIM1 and the rice cDNA products are shown in FIG. 2 (See also, SEQ ID NO:2 and SEQ ID NO's:17–24). The NIM1 protein fragments show from 36 to 48% identical amino acid sequences with the 4 rice products. These rice EST's may be especially useful for isolation of NIM1 homologues from other monocots.

Homologues may also be obtained by PCR. In this method, comparisons are made between known homologues (e.g., rice and Arabidopsis). Regions of high amino acid and DNA similarity or identity are then used to make PCR primers. Regions rich in amino acid residues M and W are best followed by regions rich in amino acid residues F, Y, C, H, Q, K and E because these amino acids are encoded by a limited number of codons. Once a suitable region is identified, primers for that region are made with a diversity of substitutions in the 3$^{rd}$ codon position. This diversity of substitution in the third position may be constrained depending on the species that is being targeted. For example, because maize is GC rich, primers are designed that utilize a G or a C in the 3$^{rd}$ position, if possible. The PCR reaction is performed from cDNA or genomic DNA under a variety of standard conditions. When a band is apparent, it is cloned and/or sequenced to determine if it is a NIM1 homologue.

Example 33

Expression of a Form of NIM1 In Crop Plants

Those constructs conferring a CIM phenotype in Col-0 or Ws-0 are transformed into crop plants for evaluation. Alternatively, altered native NIM1 genes isolated from crops in the preceding example are put back into the respective crops. Although the NIM1 gene can be inserted into any plant cell falling within these broad classes, it is particularly useful in crop plant cells, such as rice, wheat, barley, rye, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. Transformants are evaluated for enhanced disease resistance. In a preferred embodiment of the invention, the expression of the NIM1 gene is at a level which is at least two-fold above the expression level of the native NIM1 gene in wild type plants and is preferably ten-fold above the wild type expression level.

Example 34

Synergistic Disease Resistance Attained by Applying A Conventional Microbicide to Transgenic Plants Overexpressing NIM1

The plant lines used in this example (6E and 7C) were generated from transformation of wild-type *Arabidopsis thaliana* plants (ecotype Ws) with the BamHI-HindIII NIM1 genomic fragment (SEQ ID NO:1—bases 1249–5655), as described above in Example 21. The fungicides metalaxyl, fosetyl, and copper hydroxide, formulated as 25%, 80%, and 70% active ingredient (ai), respectively, with a wettable powder carrier, were applied as fine mist to leaves of three week-old transgenic Ws plants constitutively expressing the NIM1 gene. The wettable powder alone was applied as a control. Three days later, plants were inoculated with a *Peronospora parasitica* isolate Emwa conidial suspension (1–2×10$^5$ spores/ml), as described in Delaney et al. (1995). Following inoculation, plants were covered to maintain high humidity and were placed in a Percival growth chamber at 17° C. with a 14-hr day/10-hr night cycle (Uknes et al., 1993). Tissue was harvested 8 days after inoculation.

Fungal infection progression was followed for 12 days by viewing under a dissecting microscope to score development of conidiophores (Delaney, et al. (1994); Dietrich, et al. (1994)). Lactophenoltrypan blue staining of individual leaves was carried out to observe fungal growth within leaf tissue. Fungal growth was quantified using a rRNA fungal probe obtained by PCR according to White et al. (1990; PCR Protocols: A guide to Methods and Application, 315–322) using primers NS1 and NS2 and *P. parasitica* EmWa DNA as templates. RNA was purified from frozen tissue by phenol/chloroform extraction following lithium chloride precipitation (Lagrimini et al, 1987: PNAS, 84: 7542–7546). Samples (7.5 µg) were separated by electrophoresis through formaldehyde agarose gels and blotted to nylon membranes (Hybond-N+, Amersham) as described by Ausbel et al. (1987). Hybridizations and washing were according to Church and Gilbert (1984, *PNAS*, 81: 1991–1995). Relative amounts of the transcript were determined using a Phosphor Imager (Molecular Dynamics, Sunnyvale, Calif.) following manufacturers instructions. Sample loading was normalized by probing stripped filter blots with the constitutively expressed b-tubulin Arabidopsis cDNA. The infestation of the untreated plants corresponded to 0% fungal growth inhibition.

Application of metalaxyl, fosetyl, or copper hydroxide to plant lines overexpressing NIM1 produced a greater-than-additive, i.e., synergistic, disease-resistant effect. This effect was determined as the synergy factor (SF), which is the ratio of observed (O) effect to expected (E) effect. The following results were obtained:

TABLE 36

Action Against *Peronospora parasitica* In Arabidopsis
Component I: NIM1 overexpression (line 6E)
Component II: metalaxyl

| Test no. | Components NIM1 | metalaxyl | Fungal Growth Inhibition % O (observed) | E (expected) | Synergy Factor O/E |
|---|---|---|---|---|---|
| control | wt | — | 0 | | |
| 1 | NIM1 | — | 10 | | |
| 2 | wt | 0.0125 g/l | 59 | | |
| 3 | wt | 0.0012 g/l | 27 | | |
| 4 | NIM1 | 0.0125 g/l | 76 | 69 | 1.1 |
| 5 | NIM1 | 0.0012 g/l | 56 | 37 | 1.5 | wt = wild-type Ws

TABLE 37

Action Against *Peronospora parasitica* In Arabidopsis
Component I: NIM1 overexpression (line 6E)
Component II: fosetyl

| Test no. | Components NIM1 | fosetyl | Fungal Growth Inhibition % O (observed) | E (expected) | Synergy Factor O/E |
|---|---|---|---|---|---|
| control | wt | — | 0 | | |
| 1 | NIM1 | — | 10 | | |
| 2 | wt | 5.0 g/l | 7 | | |
| 3 | wt | 0.5 g/l | 2 | | |
| 4 | wt | 0.05 g/l | 0 | | |
| 5 | NIM1 | 5.0 g/l | 93 | 17 | 5.5 |
| 6 | NIM1 | 0.5 g/l | 83 | 12 | 6.9 |
| 7 | NIM1 | 0.05 g/l | 42 | 10 | 4.2 | wt = wild-type Ws

TABLE 38

Action Against *Peronospora parasitica* In Arabidopsis
Component I: NIM1 overexpression (line 7C)
Component II: fosetyl

| Test no. | Components NIM1 | fosetyl | Fungal Growth Inhibition % O (observed) | E (expected) | Synergy Factor O/E |
|---|---|---|---|---|---|
| control | wt | — | 0 | | |
| 1 | NIM1 | -- | 14 | | |
| 2 | wt | 5.0 g/l | 7 | | |
| 3 | wt | 0.5 g/l | 2 | | |
| 4 | NIM1 | 5.0 g/l | 80 | 21 | 3.8 |
| 5 | NIM1 | 0.5 g/l | 56 | 16 | 3.5 | wt = wild-type Ws

TABLE 39

Action Against *Peronospora parasitica* In Arabidopsis
Component I: NIM1 overexpression (line 6E)
Component II: copper hydroxide

| Test no. | Components NIM1 | Cu(OH)$_2$ | Fungal Growth Inhibition % O (observed) | E (expected) | Synergy Factor O/E |
|---|---|---|---|---|---|
| control | wt | — | 0 | | |
| 1 | NIM1 | — | 10 | | |
| 2 | wt | 2.0 g/l | 0 | | |
| 3 | wt | 0.2 g/l | 0 | | |
| 4 | wt | 0.02 g/l | 0 | | |
| 5 | NIM1 | 2.0 g/l | 66 | 10 | 6.6 |
| 6 | NIM1 | 0.2 g/l | 14 | 10 | 1.4 |
| 7 | NIM1 | 0.02 g/l | 20 | 10 | 2.0 | wt = wild-type Ws

TABLE 40

Action Against *Peronospora parasitica* In Arabidopsis
Component I: NIM1 overexpression (line 7C)
Component II: copper hydroxide

| Test no. | Components NIM1 | Cu(OH)$_2$ | Fungal Growth Inhibition % O (observed) | E (expected) | Synergy Factor O/E |
|---|---|---|---|---|---|
| control | wt | — | 0 | | |
| 1 | NIM1 | — | 14 | | |
| 2 | wt | 2.0 g/l | 0 | | |
| 3 | wt | 0.2 g/l | 0 | | |
| 4 | wt | 0.02 g/l | 0 | | |
| 5 | NIM1 | 2.0 g/l | 77 | 14 | 5.5 |
| 6 | NIM1 | 0.2 g/l | 51 | 14 | 3.6 |
| 7 | NIM1 | 0.02 g/l | 55 | 14 | 3.9 | wt = wild-type Ws

As can be seen from the above tables, synergistic disease-resistant effects were demonstrated in plants overexpressing NIM1 by application of metalaxyl, fosetyl, and copper hydroxide. For example, in the untreated NIM1 plant (line 6E), 10% fungal growth inhibition was seen relative to the untreated wild-type plant; this demonstrates that the constitutive SAR gene expression in this NIM1 overexpressor correlates with disease resistance. As shown above in Table 37, however, by applying fosetyl at 5.0 g/l (a concentration normally insufficient for efficacy) to the immunomodulated (SAR-on) NIM1 overexpressing plant, the observed level of fungal growth inhibition increased to 93%. The synergy factor of 5.5 calculated from these data clearly demonstrates the synergistic effect achieved by applying a microbicide to an immunomodulated (Sar-on) plant. In another example, in the untreated NIM1 plant (line 7C), 14% fungal growth inhibition was seen relative to the untreated wild-type plant, demonstrating that the constitutive SAR gene expression in this NIM1 overexpressor correlates with disease resistance. As shown above in Table 40, however, by applying copper hydroxide at 2.0 g/l (a concentration normally insufficient for efficacy) to the immunomodulated (SAR-on) NIM1 overexpressing plant, the observed level of fungal growth inhibition increased to 77%. The synergy factor of 5.5 calculated from these data further demonstrates the synergistic effect achieved by applying a microbicide to an modulated (SAR-on) plant.

Thus, the combined use of of immunomodulated plants overexpressing NIM1 with low, normally ineffective concentrations of microbicides to achieve disease resistance provides advantages that should be apparent to those skilled in the agricultural arts. Normally toxic or otherwise undesirable concentrations of microbicides can be avoided by taking advantage of the synergies demonstrated herein. In addition, economic gains can be realized as a result of the decreased quantity of microbicides required to provide a given level of protection to plants.

Example 35
Synergistic Disease Resistance Attained by Applying a Chemical Inducer of SAR to Transgenic Plants Overexpressing NIM1

Transgenic plants containing the NIM1 genomic DNA fragment under its own promoter (Example 21) were also analyzed for response to different concentrations of BTH relative to the wild-type Ws line. Seeds from each line were sown and grown as previously described. At approximately three weeks post-planting, leaf samples were harvested from each line (day 0 controls), and the remaining plants were treated with $H_2O$, 10 μM BTH, or 100 μM BTH. Additional samples were harvested at days 1, 3, and 5 following treatment. After harvesting the day 3 samples, a subset of plants for each line was removed and treated with *Peronospora parasitica* isolate Emwa as described above. RNA was prepared from the harvested tissue and Northern analysis was performed using the Arabidopsis PR-1 gene probe. Plants were scored for fungal resistance 8 days following infection.

The results of Northern analysis for Ws and four of the NIM-overexpressing lines (3A, 5B, 6E, and 7C) are shown in FIG. 3. PR-1 gene expression in the wild-type Ws line was barely detectable after the low level 10 μM BTH treatment (a BTH concentration of 100–300 μM is normally required for efficacy). Ws plants from this treatment were also still susceptible to the fungal pathogen *P. parasitica* (Emwa). In all of the NIM1-overexpressing lines, however, there was a much stronger response for PR-1 gene expression following the low-level BTH treatment. In addition, all of the NIM1-overexpressing lines treated with 10 μM BTH showed complete or almost complete resistance to *P. parasitica*. Leaves stained with lactophenol blue to identify the presence of fungal hyphae (Dietrich et al. (1994)) confirmed the absence of fungal growth in the NIM1-overexpressing lines. PR-1 gene expression in leaf tissue following the 100 μM BTH treatment was also much stronger and quicker in the NIM1-overexpressing lines relative to wild-type. Thus, immunomodulated plants are able to respond much faster and to much lower doses of BTH, as shown by PR-1 gene expression and resistance to *P. parasitica*, than wild-type plants. This data demonstrates that synergistic disease resistance is achieved by applying a chemical inducer of systemic acquired resistance such as BTH to an immunomodulated (SAR-on) plant such as a NIM1-overexpressing plant.

Thus, the combined use of immunomodulated plants overexpressing NIM1 with low, normally ineffective concentrations of SAR-inducing chemicals such as BTH to achieve disease resistance provides advantages that should be apparent to those skilled in the agricultural arts. Normally toxic or otherwise undesirable concentrations of SAR-inducing chemicals can be avoided by taking advantage of the synergies demonstrated herein. In addition, economic gains can be realized as a result of the decreased quantity of SAR-inducing chemicals required to provide a given level of protection to plants.

What is claimed is:

1. A method for protecting a plant from pathogen attack, comprising the steps of:
　　(a) providing a plant transformed with a chimeric gene comprising a promoter active in plants operatively linked to a nucleotide sequence encoding SEQ ID NO:2, wherein said plant exhibits a first level of disease resistance; and
　　(b) applying to said plant a microbicide that confers a second level of disease resistance;
　　(c) whereby application of said microbicide to said plant confers a synergistically enhanced third level of disease resistance that is greater than the sum of the first and second levels of disease resistance.

2. A method according to claim 1, wherein said nucleotide sequence comprises the coding sequence set forth in SEQ ID NO:1.

3. A method according to claim 1, wherein said microbicide is a fungicide selected from the following group:

- 4-[3-(4-chlorophenyl)-3-(3,4-dimethoxyphenyl)acryloyl]morpholine ("dimethomorph");
- 5-methyl-1,2,4-triazolo[3,4-b][1,3]benzothiazole ("tricycliazole");
- 3-allyloxy-1,2-benzothiazole-1,1-dioxide ("probonazole");
- $\mu$-[2-(4-chlorophenyl)ethyl]--$\mu$-(1,1-dimethylethyl)-1H-1,2,4-triazole-1-ethanol,("tebuconazol");
- 1-[[3-(2-chlorophenyl)-2--(4-fluorophenyl)oxiran-2-yl]methyl]-1H-1,2,4-triazole, ("epoxyconazol");
- $\mu$-(4-chlorophenyl)--$\mu$-(1-cyclopropylethyl)--1H-1,2,4-triazole--1-ethanol, ("cyproconazol");
- 5-(4-chlorobenzyl)--2,2-dimethyl-1--(1H-1,2,4-triazol-1--ylmethyl)-cyclopentanol, ("metconazol");
- 2-(2,4-dichlorophenyl)--3-(1H-1,2,4-triazol-1-yl)-propyl--1,1,2,2-tetrafluoroethyl-ether, ("tetraconazol");
- methyl-(E)-2-{2-[6-(2-cyanophenoxy)pyrimidin--4-yloxy]phenyl}--3-methoxyacrylate, ("ICI A 5504", "azoxystrobin");
- methyl-(E)--2-methoximino--2-[$\mu$-(o-tolyloxy)--o-tolyl]acetate, ("BAS 490 F", "cresoxime methyl");
- 2-(2-phenoxyphenyl)-(E)-2-methoximino--N-methylacetamide);
- [2-(2,5-dimethylphenoxymethyl)-phenyl]-(E)--2-methoximino-N-methylacetamide);
- (1R,3S/1S,3R)-2,2-dichloro--N-[(R)-1-(4-chlorophenyl)ethyl]--1-ethyl-3-methylcyclopropanecarboxamide, ("KTU 3616");
- manganese ethylenebis(dithiocarbamate)polymer-zinc complex, ("mancozeb");
- 1-[2-(2,4-dichlorophenyl)-4-propyl-1,3-dioxolan--2-ylmethyl]--1H-1,2,4--triazole, ("propiconazole");
- 1-{2-[2-chloro-4-(4-chlorophenoxy)phenyl]-4-methyl--1,3-dioxolan--2-ylmethyl 1)--1H-1,2,4--triazole, ("difenoconazole");
- 1-[2-(2,4-dichlorophenyl)pentyl--1H-1,2,4-triazole, ("penconazole");
- cis-4-[3-(4-tert-butylphenyl)--2-methylpropyl]--2,6-dimethylmorpholine, ("fenpropimorph");
- 1-[3-(4-tert-butylphenyl)--2-methylpropyl]-piperidine, ("fenpropidin");
- 4-cyclopropyl-6-methyl-N-phenyl-2-pyrimidinamine ("cyprodinil");
- (RS)-N-(2,6-dimethylphenyl--N-(methoxyacetyl)-alanine methyl ester ("metalaxyl", "ridomil");
- (R)-N-(2,6-dimethylphenyl--N-(methoxyacetyl)-alanine methyl ester ("R-metalaxyl");
- 1,2,5,6-tetrahydro--4H-pyrrolo[3,2,1-ij]quinolin-4-one ("pyroquilon"); and
- ethyl hydrogen phosphonate ("fosetyl").

4. A method according to claim 1, wherein said microbicide is either a benzothiadiazole compound, an isonicotinic acid compound, or a salicylic acid compound.

5. A method according to claim 4, wherein said microbicide is a benzothiadiazole compound.

6. A method according to claim 5, wherein said benzothiadiazole compound is benzo(1,2,3)thiadiazole-7-carbothioic acid S-methyl ester.

7. A method according to claim 1, wherein said microbicide is 4-[3-(4-chlorophenyl)-3-(3,4-dimethoxyphenyl) acryloyl]morpholine ("dimethomorph").

8. A method according to claim 1, wherein said microbicide is 5-methyl-1,2,4-triazolo[3,4-b][1,3]benzothiazole ("tricyclazole").

9. A method according to claim 1, wherein said microbicide is 3-allyloxy-1,2-benzothiazole-1,1-dioxide ("probonazole").

10. A method according to claim 1, wherein said microbicide is $\mu$-[2-(4-chlorophenyl)ethyl]--$\mu$-(1,1-dimethylethyl)-1H-1,2,4-triazole-1-ethanol ("tebuconazol").

11. A method according to claim 1, wherein said microbicide is 1-[[3-(2-chlorophenyl)-2--(4-fluorophenyl)oxiran-2-yl]methyl]-1H-1,2,4-triazole ("epoxyconazol").

12. A method according to claim 1, wherein said microbicide is $\mu$-(4-chlorophenyl)--$\mu$-(1-cyclopropylethyl)--1H-1,2,4-triazole--1-ethanol ("cyproconazol").

13. A method according to claim 1, wherein said microbicide is 5-(4-chlorobenzyl)--2,2-dimethyl-1--(1H-1,2,4-triazol-1--ylmethyl)-cyclopentanol ("metconazol").

14. A method according to claim 1, wherein said microbicide is 2-(2,4-dichlorophenyl)--3-(1H-1,2,4-triazol-1-yl)-propyl--1,1,2,2-tetrafluoroethyl-ether ("tetraconazol").

15. A method according to claim 1, wherein said microbicide is methyl-(E)-2-{2-[6-(2-cyanophenoxy)pyrimidin--4-yloxy]phenyl}--3-methoxyacrylate ("ICI A 5504", "azoxystrobin").

16. A method according to claim 1, wherein said microbicide is methyl-(E)--2-methoximino--2-[$\mu$-(o-tolyloxy)--o-tolyl]acetate ("BAS 490 F", "cresoxime methyl").

17. A method according to claim 1, wherein said microbicide is 2-(2-phenoxyphenyl)-(E)-2-methoximino--N-methylacetamide.

18. A method according to claim 1, wherein said microbicide is [2-(2,5-dimethylphenoxymethyl)-phenyl]-(E)--2-methoximino-N-methylacetamide.

19. A method according to claim 1, wherein said microbicide is (1R,3S/1S,3R)-2,2-dichloro--N-[(R)-1-(4-chlorophenyl)ethyl]--1-ethyl-3-methylcyclopropanecarboxamide ("KTU 3616").

20. A method according to claim 1, wherein said microbicide is manganese ethylenebis(dithiocarbamate)polymer-zinc complex ("mancozeb").

21. A method according to claim 1, wherein said microbicide is 1-[2-(2,4-dichlorophenyl)-4-propyl-1,3-dioxolan--2-ylmethyl]--1H-1,2,4--triazole ("propiconazole").

22. A method according to claim 1, wherein said microbicide is 1-{2-[2-chloro-4-(4-chlorophenoxy)phenyl]-4-methyl--1,3-dioxolan--2-ylmethy 1)--1H-1,2,4--triazole ("difenoconazole").

23. A method according to claim 1, wherein said microbicide is 1-[2-(2,4-dichlorophenyl)pentyl--1H-1,2,4-triazole ("penconazole").

24. A method according to claim 1, wherein said microbicide is cis-4-[3-(4-tert-butylphenyl)--2-methylpropyl]--2,6-dimethylmorpholine ("fenpropimorph").

25. A method according to claim 1, wherein said microbicide is 1-[3-(4-tert-butylphenyl)--2-methylpropyl]-piperidine ("fenpropidin").

26. A method according to claim 1, wherein said microbicide is 4-cyclopropyl-6-methyl-N-phenyl-2-pyrimidinamine ("cyprodinil").

27. A method according to claim 1, wherein said microbicide is (RS)-N-(2,6-dimethylphenyl--N-(methoxyacetyl)-alanine methyl ester ("metalaxyl", "ridomil").

28. A method according to claim 1, wherein said microbicide is (R)-N-(2,6-dimethylphenyl--N-(methoxyacetyl)-alanine methyl ester ("R-metalaxyl").

29. A method according to claim 1, wherein said microbicide is 1,2,5,6-tetrahydro--4H-pyrrolo[3,2,1-ij]quinolin-4-one ("pyroquilon").

30. A method according to claim 1, wherein said microbicide is ethyl hydrogen phosphonate ("fosetyl").

31. A method according to claim 1, wherein said microbicide is copper hydroxide.

32. A method according to claim 1, wherein said plant is selected from the group consisting of: barley, cucumber, tobacco, rice, chili, wheat, banana, and tomato.

* * * * *

UNITED STATES PATENT AND TRADEMARK OFFICE
Certificate

Patent No. 6,031,153 B1

Patented: February 29, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: John Andrew Ryals, Cary; NC; Leslie Bethards Friedrich, Apex, NC; Scott Joseph Uknes, Apex, NC; Antonio Molina-Fernandez, Blanca, Spain; Wilhelm Ruess, Pfeffingen, Switzerland; Gertrude Knauf-Beiter, Mullheim, Germany; Ruth Beatrice Kung, Allschwil, Switzerland; Helmut Kessmann, Allschwil, Switzerland; Michael Oostendorp, Rheinfelden, Germany; and Kay Ann Lawton, Raleigh, NC.

Signed and Sealed this First Day of April 2003.

AMY J. NELSON
*Supervisory Patent Examiner*
Art Unit 1638

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 5655 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: exon
      (B) LOCATION: 2787..3347
      (D) OTHER INFORMATION: /product= "1st exon of NIM1"

(ix) FEATURE:
      (A) NAME/KEY: exon
      (B) LOCATION: 3427..4162
      (D) OTHER INFORMATION: /product= "2nd exon of NIM1"

(ix) FEATURE:
      (A) NAME/KEY: exon
      (B) LOCATION: 4271..4474
      (D) OTHER INFORMATION: /product= "3rd exon of NIM1"

(ix) FEATURE:
    (A) NAME/KEY: exon
    (B) LOCATION: 4586..4866
    (D) OTHER INFORMATION: /product= "4th exon of NIM1"

(ix) FEATURE:
    (A) NAME/KEY: CDS
    (B) LOCATION: join(2787..3347, 3427..4162, 4271..4474, 4586..4866)

(xi) SEQUENCE DESCRIPTION: SEQ ID NO:1:

```
TGTGATGCAA GTCATGGGAT ATTGCTTTGT GTTAAGTATA CAAAACCATC ACGTGGATAC      60
ATAGTCTTCA AACCAACCAC TAAACAGTAT CAGGTCATAC CAAAGCCAGA AGTGAAGGGT     120
TGGGATATGT CATTGGGTTT AGCGGTAATC GGATTGAACC CTTTCCGGTA TAAAATACAA     180
AGGCTTTCGC AGTCTCGGCG TATGTGTATG TCTCGGGGTA TCTACCATTT GAATCACAGA     240
ACTTTTATGT GCGAAGTTTT CGATTCTGAT TCGTTTACCT GGAAGAGATT AGAAAATTTG     300
CGTCTACCAA AAACAGACAG ATTAATTTTT TCCAACCCGA TACAAGTTTC GGGGTTCTTG     360
CATTGGATAT CACGGAACAA CAATGTGATC CGGTTTTGTC TCAAAACCGA AACTTGGTCC     420
TTCTTCCATA CTCCGAACTC TGATGTTTTC TCAGGATTAG TCAGATACGA AGGGAAGCTA     480
GGTGCTATTC GTCAGTGGAC AAACAAAGAT CAAGAAGATG TTCACGAGTT ATGGGTTTTA     540
AAGAGCAGTT TTGAAAAGTC GTGGGTAAAA GTGAAAGATA TTAAAAGCAT TGGAGTAGAT     600
TTGATTACGT GGACTCCAAG CAACGACGTT GTATTGTTTC GTAGTAGTGA TCGTGGTTGC     660
CTCTACAACA TAAACGCAGA GAAGTTGAAT TTAGTTTATG CAAAAAAAGA GGGATCTGAT     720
TGTTCTTTCG TTTGTTTTCC GTTTTGTTCT GATTACGAGA GGGTTGATCT GAACGGAAGA     780
AGCAACGGGC CGACACTTTA AAAAAAAAAT AAAAAAAATG GGCCGACAAA TGCAAACGTA     840
GTTGACAAGG ATCTCAAGTC TCAAGTCTCA ATTGGCTCGC TCATTGTGGG GCATAAAATAT    900
ATCTAGTGAT GTTAATTGT TTTTTATAAG GTAAAAAGGA ATATTGAATT TTGTTTCTTA      960
GGTTTATGTA ATAATACCAA ACATTGTTTT ATGAATATTT AATCTGATTT TTTGGCTAGT    1020
TATTTTATTA TATCAAGGGT TCCTGTTTAT AGTTGAAAAC AGTTACTGTA TAGAAAATAG    1080
TGTCCCAATT TTCTCTCTTA ATAATATAT TAGTTAATAA AAGATATTTT AATATATTAG     1140
ATATACATAA TATCTAAAGC AACACATATT TAGCACAAC ACGTAATATC TTACTATTGT     1200
TTACATATAT TTATAGCTTA CCAATATAAC CCGTATCTAT GTTTTATAAG CTTTTATACA    1260
ATATATGTAC GGTATGCTGT CCACGTATAT ATATTCTCCA AAAAAAACGC ATGGTACACA    1320
AAATTTATTA AATATTTGGC AATTGGGTGT TTATCTAAAG TTTATCACAA TATTTATCAA    1380
CTATAATAGA TGGTAGAAGA TAAAAAAATT ATATCAGATT GATTCAATTA AATTTTATAA    1440
TATATCATTT TAAAAAATTA ATTAAAAGAA AACTATTTCA TAAAATTGTT CAAAAGATAA    1500
TTAGTAAAAT TAATTAAATA TGTGATGCTA TTGAGTTATA GAGAGTTATT GTAAATTTAC    1560
TTAAAATCAT ACAAATCTTA TCCTAATTTA ACTTATCATT TAAGAAATAC AAAAGTAAAA    1620
AACGCGGAAA GCAATAATTT ATTTACCTTA TTATAACTCC TATATAAAGT ACTCTGTTTA    1680
TTCAACATAA TCTTACGTTG TTGTATTCAT AGGCATCTTT AACCTATCTT TTCATTTTCT    1740
GATCTCGATC GTTTTCGATC CAACAAAATG AGTCTACCGG TGAGGAACCA AGAGGTGATT    1800
ATGCAGATTC CTTCTTCTTC TCAGTTTCCA GCAACATCGA GTCCGGAAAA CACCAATCAA    1860
GTGAAGGATG AGCCAAATTT GTTTAGACGT GTTATGAATT TGCTTTTACG TCGTAGTTAT    1920
TGAAAAAGCT GATTTATCGC ATGATTCAGA ACGAGAAGTT GAAGGCAAAT AACTAAAGAA    1980
```

```
GTCTTTTATA TGTATACAAT AATTGTTTTT AAATCAAATC CTAATTAAAA AAATATATTC      2040

ATTATGACTT TCATGTTTTT AATGTAATTT ATTCCTATAT CTATAATGAT TTTGTTGTGA      2100

AGAGCGTTTT CATTTGCTAT AGAACAAGGA GAATAGTTCC AGGAAATATT CGACTTGATT      2160

TAATTATAGT GTAAACATGC TGAACACTGA AAATTACTTT TTCAATAAAC GAAAAATATA      2220

ATATACATTA CAAAACTTAT GTGAATAAAG CATGAAACTT AATATACGTT CCCTTTATCA      2280

TTTTACTTCA AAGAAAATAA ACAGAAATGT AACTTTCACA TGTAAATCTA ATTCTTAAAT      2340

TTAAAAAATA ATATTTATAT ATTTATATGA AAATAACGAA CCGGATGAAA AATAAATTTT      2400

ATATATTTAT ATCATCTCCA AATCTAGTTT GGTTCAGGGG CTTACCGAAC CGGATTGAAC      2460

TTCTCATATA CAAAAATTAG CAACACAAAA TGTCTCCGGT ATAAATACTA ACATTTATAA      2520

CCCGAACCGG TTTAGCTTCC TGTTATATCT TTTTAAAAAA GATCTCTGAC AAAGATTCCT      2580

TTCCTGGAAA TTTACCGGTT TTGGTGAAAT GTAAACCGTG GGACGAGGAT GCTTCTTCAT      2640

ATCTCACCAC CACTCTCGTT GACTTGACTT GGCTCTGCTC GTCAATGGTT ATCTTCGATC      2700

TTTAACCAAA TCCAGTTGAT AAGGTCTCTT CGTTGATTAG CAGAGATCTC TTTAATTTGT      2760

GAATTTCAAT TCATCGGAAC CTGTTG ATG GAC ACC ACC ATT GAT GGA TTC GCC      2813
                               Met Asp Thr Thr Ile Asp Gly Phe Ala
                                1               5

GAT TCT TAT GAA ATC AGC AGC ACT AGT TTC GTC GCT ACC GAT AAC ACC        2861
Asp Ser Tyr Glu Ile Ser Ser Thr Ser Phe Val Ala Thr Asp Asn Thr
 10              15                  20                  25

GAC TCC TCT ATT GTT TAT CTG GCC GCC GAA CAA GTA CTC ACC GGA CCT        2909
Asp Ser Ser Ile Val Tyr Leu Ala Ala Glu Gln Val Leu Thr Gly Pro
                 30                  35                  40

GAT GTA TCT GCT CTG CAA TTG CTC TCC AAC AGC TTC GAA TCC GTC TTT        2957
Asp Val Ser Ala Leu Gln Leu Leu Ser Asn Ser Phe Glu Ser Val Phe
             45                  50                  55

GAC TCG CCG GAT GAT TTC TAC AGC GAC GCT AAG CTT GTT CTC TCC GAC        3005
Asp Ser Pro Asp Asp Phe Tyr Ser Asp Ala Lys Leu Val Leu Ser Asp
         60                  65                  70

GGC CGG GAA GTT TCT TTC CAC CGG TGC GTT TTG TCA GCG AGA AGC TCT        3053
Gly Arg Glu Val Ser Phe His Arg Cys Val Leu Ser Ala Arg Ser Ser
 75                  80                  85

TTC TTC AAG AGC GCT TTA GCC GCC GCT AAG AAG GAG AAA GAC TCC AAC        3101
Phe Phe Lys Ser Ala Leu Ala Ala Ala Lys Lys Glu Lys Asp Ser Asn
 90                  95                 100                 105

AAC ACC GCC GCC GTG AAG CTC GAG CTT AAG GAG ATT GCC AAG GAT TAC        3149
Asn Thr Ala Ala Val Lys Leu Glu Leu Lys Glu Ile Ala Lys Asp Tyr
             110                 115                 120

GAA GTC GGT TTC GAT TCG GTT GTG ACT GTT TTG GCT TAT GTT TAC AGC        3197
Glu Val Gly Phe Asp Ser Val Val Thr Val Leu Ala Tyr Val Tyr Ser
         125                 130                 135

AGC AGA GTG AGA CCG CCG CCT AAA GGA GTT TCT GAA TGC GCA GAC GAG        3245
Ser Arg Val Arg Pro Pro Pro Lys Gly Val Ser Glu Cys Ala Asp Glu
     140                 145                 150

AAT TGC TGC CAC GTG GCT TGC CGG CCG GCG GTG GAT TTC ATG TTG GAG        3293
Asn Cys Cys His Val Ala Cys Arg Pro Ala Val Asp Phe Met Leu Glu
 155                 160                 165

GTT CTC TAT TTG GCT TTC ATC TTC AAG ATC CCT GAA TTA ATT ACT CTC        3341
Val Leu Tyr Leu Ala Phe Ile Phe Lys Ile Pro Glu Leu Ile Thr Leu
170                 175                 180                 185

TAT CAG GTAAAACACC ATCTGCATTA AGCTATGGTT ACACATTCAT GAATATGTTC        3397
Tyr Gln
```

-continued

```
TTACTTGAGT ACTTGTATTT GTATTTCAG AGG CAC TTA TTG GAC GTT GTA GAC             3450
                                  Arg His Leu Leu Asp Val Val Asp
                                      190             195

AAA GTT GTT ATA GAG GAC ACA TTG GTT ATA CTC AAG CTT GCT AAT ATA             3498
Lys Val Val Ile Glu Asp Thr Leu Val Ile Leu Lys Leu Ala Asn Ile
                    200             205             210

TGT GGT AAA GCT TGT ATG AAG CTA TTG GAT AGA TGT AAA GAG ATT ATT             3546
Cys Gly Lys Ala Cys Met Lys Leu Leu Asp Arg Cys Lys Glu Ile Ile
            215                 220                 225

GTC AAG TCT AAT GTA GAT ATG GTT AGT CTT GAA AAG TCA TTG CCG GAA             3594
Val Lys Ser Asn Val Asp Met Val Ser Leu Glu Lys Ser Leu Pro Glu
        230                 235                 240

GAG CTT GTT AAA GAG ATA ATT GAT AGA CGT AAA GAG CTT GGT TTG GAG             3642
Glu Leu Val Lys Glu Ile Ile Asp Arg Arg Lys Glu Leu Gly Leu Glu
    245                 250                 255

GTA CCT AAA GTA AAG AAA CAT GTC TCG AAT GTA CAT AAG GCA CTT GAC             3690
Val Pro Lys Val Lys Lys His Val Ser Asn Val His Lys Ala Leu Asp
260                 265                 270                 275

TCG GAT GAT ATT GAG TTA GTC AAG TTG CTT TTG AAA GAG GAT CAC ACC             3738
Ser Asp Asp Ile Glu Leu Val Lys Leu Leu Leu Lys Glu Asp His Thr
                280                 285                 290

AAT CTA GAT GAT GCG TGT GCT CTT CAT TTC GCT GTT GCA TAT TGC AAT             3786
Asn Leu Asp Asp Ala Cys Ala Leu His Phe Ala Val Ala Tyr Cys Asn
            295                 300                 305

GTG AAG ACC GCA ACA GAT CTT TTA AAA CTT GAT CTT GCC GAT GTC AAC             3834
Val Lys Thr Ala Thr Asp Leu Leu Lys Leu Asp Leu Ala Asp Val Asn
        310                 315                 320

CAT AGG AAT CCG AGG GGA TAT ACG GTG CTT CAT GTT GCT GCG ATG CGG             3882
His Arg Asn Pro Arg Gly Tyr Thr Val Leu His Val Ala Ala Met Arg
    325                 330                 335

AAG GAG CCA CAA TTG ATA CTA TCT CTA TTG GAA AAA GGT GCA AGT GCA             3930
Lys Glu Pro Gln Leu Ile Leu Ser Leu Leu Glu Lys Gly Ala Ser Ala
340                 345                 350                 355

TCA GAA GCA ACT TTG GAA GGT AGA ACC GCA CTC ATG ATC GCA AAA CAA             3978
Ser Glu Ala Thr Leu Glu Gly Arg Thr Ala Leu Met Ile Ala Lys Gln
                360                 365                 370

GCC ACT ATG GCG GTT GAA TGT AAT AAT ATC CCG GAG CAA TGC AAG CAT             4026
Ala Thr Met Ala Val Glu Cys Asn Asn Ile Pro Glu Gln Cys Lys His
            375                 380                 385

TCT CTC AAA GGC CGA CTA TGT GTA GAA ATA CTA GAG CAA GAA GAC AAA             4074
Ser Leu Lys Gly Arg Leu Cys Val Glu Ile Leu Glu Gln Glu Asp Lys
        390                 395                 400

CGA GAA CAA ATT CCT AGA GAT GTT CCT CCC TCT TTT GCA GTG GCG GCC             4122
Arg Glu Gln Ile Pro Arg Asp Val Pro Pro Ser Phe Ala Val Ala Ala
    405                 410                 415

GAT GAA TTG AAG ATG ACG CTG CTC GAT CTT GAA AAT AGA G                       4162
Asp Glu Leu Lys Met Thr Leu Leu Asp Leu Glu Asn Arg
420                 425                 430

GTATCTATCA AGTCTTATTT CTTATATGTT TGAATTAAAT TTATGTCCTC TCTATTAGGA           4222

AACTGAGTGA ACTAATGATA ACTATTCTTT GTGTCGTCCA CTGTTTAG TT GCA CTT             4278
                                                    Val Ala Leu
                                                            435

GCT CAA CGT CTT TTT CCA ACG GAA GCA CAA GCT GCA ATG GAG ATC GCC             4326
Ala Gln Arg Leu Phe Pro Thr Glu Ala Gln Ala Ala Met Glu Ile Ala
                440                 445                 450

GAA ATG AAG GGA ACA TGT GAG TTC ATA GTG ACT AGC CTC GAG CCT GAC             4374
Glu Met Lys Gly Thr Cys Glu Phe Ile Val Thr Ser Leu Glu Pro Asp
            455                 460                 465
```

```
CGT CTC ACT GGT ACG AAG AGA ACA TCA CCG GGT GTA AAG ATA GCA CCT         4422
Arg Leu Thr Gly Thr Lys Arg Thr Ser Pro Gly Val Lys Ile Ala Pro
        470                 475                 480

TTC AGA ATC CTA GAA GAG CAT CAA AGT AGA CTA AAA GCG CTT TCT AAA         4470
Phe Arg Ile Leu Glu Glu His Gln Ser Arg Leu Lys Ala Leu Ser Lys
    485                 490                 495

ACC G GTATGGATTC TCACCCACTT CATCGGACTC CTTATCACAA AAAACAAAAC            4524
Thr
500

TAAATGATCT TTAAACATGG TTTTGTTACT TGCTGTCTGA CCTTGTTTTT TTTATCATCA       4584

G  TG GAA CTC GGG AAA CGA TTC TTC CCG CGC TGT TCG GCA GTG CTC           4629
   Val Glu Leu Gly Lys Arg Phe Phe Pro Arg Cys Ser Ala Val Leu
               505                 510                 515

GAC CAG ATT ATG AAC TGT GAG GAC TTG ACT CAA CTG GCT TGC GGA GAA         4677
Asp Gln Ile Met Asn Cys Glu Asp Leu Thr Gln Leu Ala Cys Gly Glu
                520                 525                 530

GAC GAC ACT GCT GAG AAA CGA CTA CAA AAG AAG CAA AGG TAC ATG GAA         4725
Asp Asp Thr Ala Glu Lys Arg Leu Gln Lys Lys Gln Arg Tyr Met Glu
            535                 540                 545

ATA CAA GAG ACA CTA AAG AAG GCC TTT AGT GAG GAC AAT TTG GAA TTA         4773
Ile Gln Glu Thr Leu Lys Lys Ala Phe Ser Glu Asp Asn Leu Glu Leu
        550                 555                 560

GGA AAT TCG TCC CTG ACA GAT TCG ACT TCT TCC ACA TCG AAA TCA ACC         4821
Gly Asn Ser Ser Leu Thr Asp Ser Thr Ser Ser Thr Ser Lys Ser Thr
    565                 570                 575

GGT GGA AAG AGG TCT AAC CGT AAA CTC TCT CAT CGT CGT CGG TGA             4866
Gly Gly Lys Arg Ser Asn Arg Lys Leu Ser His Arg Arg Arg *
580                 585                 590

GACTCTTGCC TCTTAGTGTA ATTTTTGCTG TACCATATAA TTCTGTTTTC ATGATGACTG       4926

TAACTGTTTA TGTCTATCGT TGGCGTCATA TAGTTTCGCT CTTCGTTTTG CATCCTGTGT       4986

ATTATTGCTG CAGGTGTGCT TCAAACAAAT GTTGTAACAA TTTGAACCAA TGGTATACAG       5046

ATTTGTAATA TATATTTATG TACATCAACA ATAACCCATG ATGGTGTTAC AGAGTTGCTA       5106

GAATCAAAGT GTGAAATAAT GTCAAATTGT TCATCTGTTG GATATTTTCC ACCAAGAACC       5166

AAAAGAATAT TCAAGTTCCC TGAACTTCTG GCAACATTCA TGTTATATGT ATCTTCCTAA       5226

TTCTTCCTTT AACCTTTTGT AACTCGAATT ACACAGCAAG TTAGTTTCAG GTCTAGAGAT       5286

AAGAGAACAC TGAGTGGGCG TGTAAGGTGC ATTCTCCTAG TCAGCTCCAT TGCATCCAAC       5346

ATTTGTGAAT GACACAAGTT AACAATCCTT TGCACCATTT CTGGGTGCAT ACATGGAAAC       5406

TTCTTCGATT GAAACTTCCC ACATGTGCAG GTGCGTTCGC TGTCACTGAT AGACCAAGAG       5466

ACTGAAAGCT TTCACAAATT GCCCTCAAAT CTTCTGTTTC TATCGTCATG ACTCCATATC       5526

TCCGACCACT GGTCATGAGC CAGAGCCCAC TGATTTTGAG GGAATTGGGC TAACCATTTC       5586

CGAGCTTCTG AGTCCTTCTT TTTGATGTCC TTTATGTAGG AATCAAATTC TTCCTTCTGA       5646

CTTGTGGAT                                                              5655
```

(2) INFORMATION FOR SEQ ID NO:2:

(i) SEQUENCE CHARACTERISTICS:
        (A) LENGTH: 593 amino acids
        (B) TYPE: amino acid
        (D) TOPOLOGY: linear (ii) MOLECULE TYPE: protein -continued (xi) SEQUENCE DESCRIPTION: SEQ ID NO:2:

```
Met Asp Thr Thr Ile Asp Gly Phe Ala Asp Ser Tyr Glu Ile Ser Ser
  1               5                  10                  15

Thr Ser Phe Val Ala Thr Asp Asn Thr Asp Ser Ser Ile Val Tyr Leu
             20                  25                  30

Ala Ala Glu Gln Val Leu Thr Gly Pro Asp Val Ser Ala Leu Gln Leu
             35                  40                  45

Leu Ser Asn Ser Phe Glu Ser Val Phe Asp Ser Pro Asp Asp Phe Tyr
 50                  55                  60

Ser Asp Ala Lys Leu Val Leu Ser Asp Gly Arg Glu Val Ser Phe His
 65                  70                  75                  80

Arg Cys Val Leu Ser Ala Arg Ser Ser Phe Phe Lys Ser Ala Leu Ala
                 85                  90                  95

Ala Ala Lys Lys Glu Lys Asp Ser Asn Asn Thr Ala Ala Val Lys Leu
                100                 105                 110

Glu Leu Lys Glu Ile Ala Lys Asp Tyr Glu Val Gly Phe Asp Ser Val
            115                 120                 125

Val Thr Val Leu Ala Tyr Val Tyr Ser Ser Arg Val Arg Pro Pro Pro
    130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
                180                 185                 190

Val Val Asp Lys Val Val Ile Glu Asp Thr Leu Val Ile Leu Lys Leu
            195                 200                 205

Ala Asn Ile Cys Gly Lys Ala Cys Met Lys Leu Leu Asp Arg Cys Lys
    210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255

Gly Leu Glu Val Pro Lys Val Lys Lys His Val Ser Asn Val His Lys
            260                 265                 270

Ala Leu Asp Ser Asp Ile Glu Leu Val Lys Leu Leu Leu Lys Glu
    275                 280                 285

Asp His Thr Asn Leu Asp Asp Ala Cys Ala Leu His Phe Ala Val Ala
290                 295                 300

Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
                325                 330                 335

Ala Met Arg Lys Glu Pro Gln Leu Ile Leu Ser Leu Leu Glu Lys Gly
            340                 345                 350

Ala Ser Ala Ser Glu Ala Thr Leu Glu Gly Arg Thr Ala Leu Met Ile
    355                 360                 365

Ala Lys Gln Ala Thr Met Ala Val Glu Cys Asn Asn Ile Pro Glu Gln
    370                 375                 380

Cys Lys His Ser Leu Lys Gly Arg Leu Cys Val Glu Ile Leu Glu Gln
385                 390                 395                 400
```

```
Glu Asp Lys Arg Glu Gln Ile Pro Arg Asp Val Pro Pro Ser Phe Ala
                405                 410                 415
Val Ala Ala Asp Glu Leu Lys Met Thr Leu Leu Asp Leu Glu Asn Arg
                420                 425                 430
Val Ala Leu Ala Gln Arg Leu Phe Pro Thr Glu Ala Gln Ala Ala Met
                435                 440                 445
Glu Ile Ala Glu Met Lys Gly Thr Cys Glu Phe Ile Val Thr Ser Leu
            450                 455                 460
Glu Pro Asp Arg Leu Thr Gly Thr Lys Arg Thr Ser Pro Gly Val Lys
465                 470                 475                 480
Ile Ala Pro Phe Arg Ile Leu Glu Glu His Gln Ser Arg Leu Lys Ala
                485                 490                 495
Leu Ser Lys Thr Val Glu Leu Gly Lys Arg Phe Pro Arg Cys Ser
                500                 505                 510
Ala Val Leu Asp Gln Ile Met Asn Cys Glu Asp Leu Thr Gln Leu Ala
                515                 520                 525
Cys Gly Glu Asp Asp Thr Ala Glu Lys Arg Leu Gln Lys Lys Gln Arg
            530                 535                 540
Tyr Met Glu Ile Gln Glu Thr Leu Lys Lys Ala Phe Ser Glu Asp Asn
545                 550                 555                 560
Leu Glu Leu Gly Asn Ser Ser Leu Thr Asp Ser Thr Ser Ser Thr Ser
                565                 570                 575
Lys Ser Thr Gly Gly Lys Arg Ser Asn Arg Lys Leu Ser His Arg Arg
                580                 585                 590
Arg
```

(2) INFORMATION FOR SEQ ID NO:3:

(i) SEQUENCE CHARACTERISTICS:
        (A) LENGTH: 314 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Met Phe Gln Pro Ala Gly His Gly Gln Asp Trp Ala Met Glu Gly Pro
1               5                   10                  15
Arg Asp Gly Leu Lys Lys Glu Arg Leu Val Asp Asp Arg His Asp Ser
                20                  25                  30
Gly Leu Asp Ser Met Lys Asp Glu Glu Tyr Glu Gln Met Val Lys Glu
                35                  40                  45
Leu Arg Glu Ile Arg Leu Gln Pro Gln Glu Ala Pro Leu Ala Ala Glu
    50                  55                  60
Pro Trp Lys Gln Gln Leu Thr Glu Asp Gly Asp Ser Phe Leu His Leu
65                  70                  75                  80
Ala Ile Ile His Glu Glu Lys Pro Leu Thr Met Glu Val Ile Gly Gln
                85                  90                  95
Val Lys Gly Asp Leu Ala Phe Leu Asn Phe Gln Asn Asn Leu Gln Gln
                100                 105                 110
Thr Pro Leu His Leu Ala Val Ile Thr Asn Gln Pro Gly Ile Ala Glu
                115                 120                 125
Ala Leu Leu Lys Ala Gly Cys Asp Pro Glu Leu Arg Asp Phe Arg Gly
            130                 135                 140
```

```
Asn Thr Pro Leu His Leu Ala Cys Glu Gln Gly Cys Leu Ala Ser Val
145                 150                 155                 160

Ala Val Leu Thr Gln Thr Cys Thr Pro Gln His Leu His Ser Val Leu
                165                 170                 175

Gln Ala Thr Asn Tyr Asn Gly His Thr Cys Leu His Leu Ala Ser Thr
            180                 185                 190

His Gly Tyr Leu Ala Ile Val Glu His Leu Val Thr Leu Gly Ala Asp
        195                 200                 205

Val Asn Ala Gln Glu Pro Cys Asn Gly Arg Thr Ala Leu His Leu Ala
210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
                260                 265                 270

Thr Leu Glu Asn Leu Gln Met Leu Pro Glu Ser Glu Asp Glu Glu Ser
            275                 280                 285

Tyr Asp Thr Glu Ser Glu Phe Thr Glu Asp Glu Leu Pro Tyr Asp Asp
        290                 295                 300

Cys Val Phe Gly Gly Gln Arg Leu Thr Leu
305                 310

(2) INFORMATION FOR SEQ ID NO:4:

(i) SEQUENCE CHARACTERISTICS:
        (A) LENGTH: 314 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:4:

Met Phe Gln Pro Ala Gly His Gly Gln Asp Trp Ala Met Glu Gly Pro
1               5                   10                  15

Arg Asp Gly Leu Lys Lys Glu Arg Leu Val Asp Asp Arg His Asp Ser
                20                  25                  30

Gly Leu Asp Ser Met Lys Asp Glu Asp Tyr Glu Gln Met Val Lys Glu
            35                  40                  45

Leu Arg Glu Ile Arg Leu Gln Pro Gln Glu Ala Pro Leu Ala Ala Glu
50                  55                  60

Pro Trp Lys Gln Gln Leu Thr Glu Asp Gly Asp Ser Phe Leu His Leu
65                  70                  75                  80

Ala Ile Ile His Glu Glu Lys Thr Leu Thr Met Glu Val Ile Gly Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Gly Ile Ala Glu
        115                 120                 125

Ala Leu Leu Lys Ala Gly Cys Asp Pro Glu Leu Arg Asp Phe Arg Gly
130                 135                 140

Asn Thr Pro Leu His Leu Ala Cys Glu Gln Gly Cys Leu Ala Ser Val
145                 150                 155                 160

Ala Val Leu Thr Gln Thr Cys Thr Pro Gln His Leu His Ser Val Leu
                165                 170                 175
```

```
Gln Ala Thr Asn Tyr Asn Gly His Thr Cys Leu His Leu Ala Ser Ile
            180                 185                 190

His Gly Tyr Leu Gly Ile Val Glu His Leu Val Thr Leu Gly Ala Asp
            195                 200                 205

Val Asn Ala Gln Glu Pro Cys Asn Gly Arg Thr Ala Leu His Leu Ala
            210                 215                 220

Val Asp Leu Gln Asn Pro Asp Leu Val Ser Leu Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Leu Gly Gln Leu
            260                 265                 270

Thr Leu Glu Asn Leu Gln Thr Leu Pro Glu Ser Glu Asp Glu Glu Ser
            275                 280                 285

Tyr Asp Thr Glu Ser Glu Phe Thr Glu Asp Leu Pro Tyr Asp Asp
            290                 295                 300

Cys Val Phe Gly Gly Gln Arg Leu Thr Leu
305                 310
```

(2) INFORMATION FOR SEQ ID NO:5:

(i) SEQUENCE CHARACTERISTICS:
        (A) LENGTH: 314 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

```
Met Phe Gln Pro Ala Glu Pro Gly Gln Glu Trp Ala Met Glu Gly Pro
1               5                   10                  15

Arg Asp Ala Leu Lys Lys Glu Arg Leu Asp Asp Arg His Asp Ser
                20                  25                  30

Gly Leu Asp Ser Met Lys Asp Glu Glu Tyr Glu Gln Met Val Lys Glu
            35                  40                  45

Leu Arg Glu Ile Arg Leu Glu Pro Gln Glu Ala Pro Arg Gly Ala Glu
50                  55                  60

Pro Trp Lys Gln Gln Leu Thr Glu Asp Gly Asp Ser Phe Leu His Leu
65                  70                  75                  80

Ala Ile Ile His Glu Glu Lys Ala Leu Thr Met Glu Val Val Arg Gln
                85                  90                  95

Val Lys Gly Asp Leu Ala Phe Leu Asn Phe Gln Asn Asn Leu Gln Gln
            100                 105                 110

Thr Pro Leu His Leu Ala Val Ile Thr Asn Gln Pro Glu Ile Ala Glu
            115                 120                 125

Ala Leu Leu Glu Ala Gly Cys Asp Pro Glu Leu Arg Asp Phe Arg Gly
            130                 135                 140

Asn Thr Pro Leu His Leu Ala Cys Glu Gln Gly Cys Leu Ala Ser Val
145                 150                 155                 160

Gly Val Leu Thr Gln Pro Arg Gly Thr Gln His Leu His Ser Ile Leu
                165                 170                 175

Gln Ala Thr Asn Tyr Asn Gly His Thr Cys Leu His Leu Ala Ser Ile
            180                 185                 190

His Gly Tyr Leu Gly Ile Val Glu Leu Leu Val Ser Leu Gly Ala Asp
            195                 200                 205
```

```
Val Asn Ala Gln Glu Pro Cys Asn Gly Arg Thr Ala Leu His Leu Ala
    210                 215                 220

Val Asp Leu Gln Asn Pro Asp Leu Val Ser Leu Leu Lys Cys Gly
225                 230                 235                 240

Ala Asp Val Asn Arg Val Thr Tyr Gln Gly Tyr Ser Pro Tyr Gln Leu
                245                 250                 255

Thr Trp Gly Arg Pro Ser Thr Arg Ile Gln Gln Gln Leu Gly Gln Leu
            260                 265                 270

Thr Leu Glu Asn Leu Gln Met Leu Pro Glu Ser Glu Asp Glu Glu Ser
        275                 280                 285

Tyr Asp Thr Glu Ser Glu Phe Thr Glu Asp Glu Leu Pro Tyr Asp Asp
    290                 295                 300

Cys Val Leu Gly Gly Gln Arg Leu Thr Leu
305                 310
```

(2) INFORMATION FOR SEQ ID NO:6:

(i) SEQUENCE CHARACTERISTICS:
        (A) LENGTH: 2011 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Arabidopsis thaliana (ix) FEATURE:
        (A) NAME/KEY: misc_feature
        (B) LOCATION: 1..2011
        (D) OTHER INFORMATION: /note= "NIM1 cDNA sequence"

(ix) FEATURE:
        (A) NAME/KEY: CDS
        (B) LOCATION: 43..1824
        (D) OTHER INFORMATION: /product= "NIM1 protein"

(xi) SEQUENCE DESCRIPTION: SEQ ID NO:6:

```
GATCTCTTTA ATTTGTGAAT TCAATTCAT CGGAACCTGT TG ATG GAC ACC ACC         54
                                              Met Asp Thr Thr
                                                1

ATT GAT GGA TTC GCC GAT TCT TAT GAA ATC AGC AGC ACT AGT TTC GTC      102
Ile Asp Gly Phe Ala Asp Ser Tyr Glu Ile Ser Ser Thr Ser Phe Val
 5              10                  15                  20

GCT ACC GAT AAC ACC GAC TCC TCT ATT GTT TAT CTG GCC GCC GAA CAA      150
Ala Thr Asp Asn Thr Asp Ser Ser Ile Val Tyr Leu Ala Ala Glu Gln
                25                  30                  35

GTA CTC ACC GGA CCT GAT GTA TCT GCT CTG CAA TTG CTC TCC AAC AGC      198
Val Leu Thr Gly Pro Asp Val Ser Ala Leu Gln Leu Leu Ser Asn Ser
            40                  45                  50

TTC GAA TCC GTC TTT GAC TCG CCG GAT GAT TTC TAC AGC GAC GCT AAG      246
Phe Glu Ser Val Phe Asp Ser Pro Asp Asp Phe Tyr Ser Asp Ala Lys
        55                  60                  65

CTT GTT CTC TCC GAC GGC CGG GAA GTT TCT TTC CAC CGG TGC GTT TTG      294
Leu Val Leu Ser Asp Gly Arg Glu Val Ser Phe His Arg Cys Val Leu
    70                  75                  80

TCA GCG AGA AGC TCT TTC TTC AAG AGC GCT TTA GCC GCC GCT AAG AAG      342
Ser Ala Arg Ser Ser Phe Phe Lys Ser Ala Leu Ala Ala Ala Lys Lys
85                  90                  95                 100

GAG AAA GAC TCC AAC AAC ACC GCC GCC GTG AAG CTC GAG CTT AAG GAG      390
Glu Lys Asp Ser Asn Asn Thr Ala Ala Val Lys Leu Glu Leu Lys Glu
                105                 110                 115
```

```
ATT GCC AAG GAT TAC GAA GTC GGT TTC GAT TCG GTT GTG ACT GTT TTG        438
Ile Ala Lys Asp Tyr Glu Val Gly Phe Asp Ser Val Val Thr Val Leu
        120                 125                 130

GCT TAT GTT TAC AGC AGC AGA GTG AGA CCG CCG CCT AAA GGA GTT TCT        486
Ala Tyr Val Tyr Ser Ser Arg Val Arg Pro Pro Pro Lys Gly Val Ser
            135                 140                 145

GAA TGC GCA GAC GAG AAT TGC TGC CAC GTG GCT TGC CGG CCG GCG GTG        534
Glu Cys Ala Asp Glu Asn Cys Cys His Val Ala Cys Arg Pro Ala Val
150                 155                 160

GAT TTC ATG TTG GAG GTT CTC TAT TTG GCT TTC ATC TTC AAG ATC CCT        582
Asp Phe Met Leu Glu Val Leu Tyr Leu Ala Phe Ile Phe Lys Ile Pro
165                 170                 175                 180

GAA TTA ATT ACT CTC TAT CAG AGG CAC TTA TTG GAC GTT GTA GAC AAA        630
Glu Leu Ile Thr Leu Tyr Gln Arg His Leu Leu Asp Val Val Asp Lys
                185                 190                 195

GTT GTT ATA GAG GAC ACA TTG GTT ATA CTC AAG CTT GCT AAT ATA TGT        678
Val Val Ile Glu Asp Thr Leu Val Ile Leu Lys Leu Ala Asn Ile Cys
                    200                 205                 210

GGT AAA GCT TGT ATG AAG CTA TTG GAT AGA TGT AAA GAG ATT ATT GTC        726
Gly Lys Ala Cys Met Lys Leu Leu Asp Arg Cys Lys Glu Ile Ile Val
                        215                 220                 225

AAG TCT AAT GTA GAT ATG GTT AGT CTT GAA AAG TCA TTG CCG GAA GAG        774
Lys Ser Asn Val Asp Met Val Ser Leu Glu Lys Ser Leu Pro Glu Glu
        230                 235                 240

CTT GTT AAA GAG ATA ATT GAT AGA CGT AAA GAG CTT GGT TTG GAG GTA        822
Leu Val Lys Glu Ile Ile Asp Arg Arg Lys Glu Leu Gly Leu Glu Val
245                 250                 255                 260

CCT AAA GTA AAG AAA CAT GTC TCG AAT GTA CAT AAG GCA CTT GAC TCG        870
Pro Lys Val Lys Lys His Val Ser Asn Val His Lys Ala Leu Asp Ser
                265                 270                 275

GAT GAT ATT GAG TTA GTC AAG TTG CTT TTG AAA GAG GAT CAC ACC AAT        918
Asp Asp Ile Glu Leu Val Lys Leu Leu Leu Lys Glu Asp His Thr Asn
                    280                 285                 290

CTA GAT GAT GCG TGT GCT CTT CAT TTC GCT GTT GCA TAT TGC AAT GTG        966
Leu Asp Asp Ala Cys Ala Leu His Phe Ala Val Ala Tyr Cys Asn Val
                        295                 300                 305

AAG ACC GCA ACA GAT CTT TTA AAA CTT GAT CTT GCC GAT GTC AAC CAT       1014
Lys Thr Ala Thr Asp Leu Leu Lys Leu Asp Leu Ala Asp Val Asn His
        310                 315                 320

AGG AAT CCG AGG GGA TAT ACG GTG CTT CAT GTT GCT GCG ATG CGG AAG       1062
Arg Asn Pro Arg Gly Tyr Thr Val Leu His Val Ala Ala Met Arg Lys
325                 330                 335                 340

GAG CCA CAA TTG ATA CTA TCT CTA TTG GAA AAA GGT GCA AGT GCA TCA       1110
Glu Pro Gln Leu Ile Leu Ser Leu Leu Glu Lys Gly Ala Ser Ala Ser
                345                 350                 355

GAA GCA ACT TTG GAA GGT AGA ACC GCA CTC ATG ATC GCA AAA CAA GCC       1158
Glu Ala Thr Leu Glu Gly Arg Thr Ala Leu Met Ile Ala Lys Gln Ala
                    360                 365                 370

ACT ATG GCG GTT GAA TGT AAT AAT ATC CCG GAG CAA TGC AAG CAT TCT       1206
Thr Met Ala Val Glu Cys Asn Asn Ile Pro Glu Gln Cys Lys His Ser
                        375                 380                 385

CTC AAA GGC CGA CTA TGT GTA GAA ATA CTA GAG CAA GAA GAC AAA CGA       1254
Leu Lys Gly Arg Leu Cys Val Glu Ile Leu Glu Gln Glu Asp Lys Arg
        390                 395                 400

GAA CAA ATT CCT AGA GAT GTT CCT CCC TCT TTT GCA GTG GCG GCC GAT       1302
Glu Gln Ile Pro Arg Asp Val Pro Pro Ser Phe Ala Val Ala Ala Asp
405                 410                 415                 420
```

| | | |
|---|---|---|
| GAA TTG AAG ATG ACG CTG CTC GAT CTT GAA AAT AGA GTT GCA CTT GCT<br>Glu Leu Lys Met Thr Leu Leu Asp Leu Glu Asn Arg Val Ala Leu Ala<br>                     425                    430                   435 | 1350 |

```
GAA TTG AAG ATG ACG CTG CTC GAT CTT GAA AAT AGA GTT GCA CTT GCT    1350
Glu Leu Lys Met Thr Leu Leu Asp Leu Glu Asn Arg Val Ala Leu Ala
            425                 430                 435

CAA CGT CTT TTT CCA ACG GAA GCA CAA GCT GCA ATG GAG ATC GCC GAA    1398
Gln Arg Leu Phe Pro Thr Glu Ala Gln Ala Ala Met Glu Ile Ala Glu
            440                 445                 450

ATG AAG GGA ACA TGT GAG TTC ATA GTG ACT AGC CTC GAG CCT GAC CGT    1446
Met Lys Gly Thr Cys Glu Phe Ile Val Thr Ser Leu Glu Pro Asp Arg
            455                 460                 465

CTC ACT GGT ACG AAG AGA ACA TCA CCG GGT GTA AAG ATA GCA CCT TTC    1494
Leu Thr Gly Thr Lys Arg Thr Ser Pro Gly Val Lys Ile Ala Pro Phe
        470                 475                 480

AGA ATC CTA GAA GAG CAT CAA AGT AGA CTA AAA GCG CTT TCT AAA ACC    1542
Arg Ile Leu Glu Glu His Gln Ser Arg Leu Lys Ala Leu Ser Lys Thr
485                 490                 495                 500

GTG GAA CTC GGG AAA CGA TTC TTC CCG CGC TGT TCG GCA GTG CTC GAC    1590
Val Glu Leu Gly Lys Arg Phe Phe Pro Arg Cys Ser Ala Val Leu Asp
                505                 510                 515

CAG ATT ATG AAC TGT GAG GAC TTG ACT CAA CTG GCT TGC GGA GAA GAC    1638
Gln Ile Met Asn Cys Glu Asp Leu Thr Gln Leu Ala Cys Gly Glu Asp
            520                 525                 530

GAC ACT GCT GAG AAA CGA CTA CAA AAG AAG CAA AGG TAC ATG GAA ATA    1686
Asp Thr Ala Glu Lys Arg Leu Gln Lys Lys Gln Arg Tyr Met Glu Ile
            535                 540                 545

CAA GAG ACA CTA AAG AAG GCC TTT AGT GAG GAC AAT TTG GAA TTA GGA    1734
Gln Glu Thr Leu Lys Lys Ala Phe Ser Glu Asp Asn Leu Glu Leu Gly
        550                 555                 560

AAT TTG TCC CTG ACA GAT TCG ACT TCT TCC ACA TCG AAA TCA ACC GGT    1782
Asn Leu Ser Leu Thr Asp Ser Thr Ser Ser Thr Ser Lys Ser Thr Gly
565                 570                 575                 580

GGA AAG AGG TCT AAC CGT AAA CTC TCT CAT CGT CGT CGG TGA            1824
Gly Lys Arg Ser Asn Arg Lys Leu Ser His Arg Arg Arg *
                585                 590

GACTCTTGCC TCTTAGTGTA ATTTTTGCTG TACCATATAA TTCTGTTTTC ATGATGACTG  1884

TAACTGTTTA TGTCTATCGT TGGCGTCATA TAGTTTCGCT CTTCGTTTTG CATCCTGTGT  1944

ATTATTGCTG CAGGTGTGCT TCAAACAAAT GTTGTAACAA TTTGAACCAA TGGTATACAG  2004

ATTTGTA                                                           2011
```

(2) INFORMATION FOR SEQ ID NO:7:

(i) SEQUENCE CHARACTERISTICS:
        (A) LENGTH: 2011 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 43..1824
        (D) OTHER INFORMATION: /product= "altered form of NIM1"
            /note= "Serine residues at amino acid positions 55
            and 59 in wild-type NIM1 gene product have been
            changed to Alanine residues."

(ix) FEATURE:
        (A) NAME/KEY: misc_feature
        (B) LOCATION: 205..217
        (D) OTHER INFORMATION: /note= "nucleotides 205 and 217
            changed from T's to G's compared to wild-type sequence."

(xi) SEQUENCE DESCRIPTION: SEQ ID NO:7:

-continued

```
GATCTCTTTA ATTTGTGAAT TTCAATTCAT CGGAACCTGT TG ATG GAC ACC ACC         54
                                               Met Asp Thr Thr
                                                 1

ATT GAT GGA TTC GCC GAT TCT TAT GAA ATC AGC AGC ACT AGT TTC GTC       102
Ile Asp Gly Phe Ala Asp Ser Tyr Glu Ile Ser Ser Thr Ser Phe Val
  5              10                  15                  20

GCT ACC GAT AAC ACC GAC TCC TCT ATT GTT TAT CTG GCC GCC GAA CAA       150
Ala Thr Asp Asn Thr Asp Ser Ser Ile Val Tyr Leu Ala Ala Glu Gln
                 25                  30                  35

GTA CTC ACC GGA CCT GAT GTA TCT GCT CTG CAA TTG CTC TCC AAC AGC       198
Val Leu Thr Gly Pro Asp Val Ser Ala Leu Gln Leu Leu Ser Asn Ser
             40                  45                  50

TTC GAA GCC GTC TTT GAC GCG CCG GAT GAT TTC TAC AGC GAC GCT AAG       246
Phe Glu Ala Val Phe Asp Ala Pro Asp Asp Phe Tyr Ser Asp Ala Lys
         55                  60                  65

CTT GTT CTC TCC GAC GGC CGG GAA GTT TCT TTC CAC CGG TGC GTT TTG       294
Leu Val Leu Ser Asp Gly Arg Glu Val Ser Phe His Arg Cys Val Leu
     70                  75                  80

TCA GCG AGA AGC TCT TTC TTC AAG AGC GCT TTA GCC GCC GCT AAG AAG       342
Ser Ala Arg Ser Ser Phe Phe Lys Ser Ala Leu Ala Ala Ala Lys Lys
 85                  90                  95                 100

GAG AAA GAC TCC AAC AAC ACC GCC GCC GTG AAG CTC GAG CTT AAG GAG       390
Glu Lys Asp Ser Asn Asn Thr Ala Ala Val Lys Leu Glu Leu Lys Glu
                105                 110                 115

ATT GCC AAG GAT TAC GAA GTC GGT TTC GAT TCG GTT GTG ACT GTT TTG       438
Ile Ala Lys Asp Tyr Glu Val Gly Phe Asp Ser Val Val Thr Val Leu
            120                 125                 130

GCT TAT GTT TAC AGC AGC AGA GTG AGA CCG CCG CCT AAA GGA GTT TCT       486
Ala Tyr Val Tyr Ser Ser Arg Val Arg Pro Pro Pro Lys Gly Val Ser
        135                 140                 145

GAA TGC GCA GAC GAG AAT TGC TGC CAC GTG GCT TGC CGG CCG GCG GTG       534
Glu Cys Ala Asp Glu Asn Cys Cys His Val Ala Cys Arg Pro Ala Val
    150                 155                 160

GAT TTC ATG TTG GAG GTT CTC TAT TTG GCT TTC ATC TTC AAG ATC CCT       582
Asp Phe Met Leu Glu Val Leu Tyr Leu Ala Phe Ile Phe Lys Ile Pro
165                 170                 175                 180

GAA TTA ATT ACT CTC TAT CAG AGG CAC TTA TTG GAC GTT GTA GAC AAA       630
Glu Leu Ile Thr Leu Tyr Gln Arg His Leu Leu Asp Val Val Asp Lys
                185                 190                 195

GTT GTT ATA GAG GAC ACA TTG GTT ATA CTC AAG CTT GCT AAT ATA TGT       678
Val Val Ile Glu Asp Thr Leu Val Ile Leu Lys Leu Ala Asn Ile Cys
            200                 205                 210

GGT AAA GCT TGT ATG AAG CTA TTG GAT AGA TGT AAA GAG ATT ATT GTC       726
Gly Lys Ala Cys Met Lys Leu Leu Asp Arg Cys Lys Glu Ile Ile Val
        215                 220                 225

AAG TCT AAT GTA GAT ATG GTT AGT CTT GAA AAG TCA TTG CCG GAA GAG       774
Lys Ser Asn Val Asp Met Val Ser Leu Glu Lys Ser Leu Pro Glu Glu
    230                 235                 240

CTT GTT AAA GAG ATA ATT GAT AGA CGT AAA GAG CTT GGT TTG GAG GTA       822
Leu Val Lys Glu Ile Ile Asp Arg Arg Lys Glu Leu Gly Leu Glu Val
245                 250                 255                 260

CCT AAA GTA AAG AAA CAT GTC TCG AAT GTA CAT AAG GCA CTT GAC TCG       870
Pro Lys Val Lys Lys His Val Ser Asn Val His Lys Ala Leu Asp Ser
                265                 270                 275

GAT GAT ATT GAG TTA GTC AAG TTG CTT TTG AAA GAG GAT CAC ACC AAT       918
Asp Asp Ile Glu Leu Val Lys Leu Leu Leu Lys Glu Asp His Thr Asn
            280                 285                 290
```

```
CTA GAT GAT GCG TGT GCT CTT CAT TTC GCT GTT GCA TAT TGC AAT GTG      966
Leu Asp Asp Ala Cys Ala Leu His Phe Ala Val Ala Tyr Cys Asn Val
        295                 300                 305

AAG ACC GCA ACA GAT CTT TTA AAA CTT GAT CTT GCC GAT GTC AAC CAT     1014
Lys Thr Ala Thr Asp Leu Leu Lys Leu Asp Leu Ala Asp Val Asn His
310                 315                 320

AGG AAT CCG AGG GGA TAT ACG GTG CTT CAT GTT GCT GCG ATG CGG AAG     1062
Arg Asn Pro Arg Gly Tyr Thr Val Leu His Val Ala Ala Met Arg Lys
325                 330                 335                 340

GAG CCA CAA TTG ATA CTA TCT CTA TTG GAA AAA GGT GCA AGT GCA TCA     1110
Glu Pro Gln Leu Ile Leu Ser Leu Leu Glu Lys Gly Ala Ser Ala Ser
            345                 350                 355

GAA GCA ACT TTG GAA GGT AGA ACC GCA CTC ATG ATC GCA AAA CAA GCC     1158
Glu Ala Thr Leu Glu Gly Arg Thr Ala Leu Met Ile Ala Lys Gln Ala
                360                 365                 370

ACT ATG GCG GTT GAA TGT AAT AAT ATC CCG GAG CAA TGC AAG CAT TCT     1206
Thr Met Ala Val Glu Cys Asn Asn Ile Pro Glu Gln Cys Lys His Ser
        375                 380                 385

CTC AAA GGC CGA CTA TGT GTA GAA ATA CTA GAG CAA GAA GAC AAA CGA     1254
Leu Lys Gly Arg Leu Cys Val Glu Ile Leu Glu Gln Glu Asp Lys Arg
390                 395                 400

GAA CAA ATT CCT AGA GAT GTT CCT CCC TCT TTT GCA GTG GCG GCC GAT     1302
Glu Gln Ile Pro Arg Asp Val Pro Pro Ser Phe Ala Val Ala Ala Asp
405                 410                 415                 420

GAA TTG AAG ATG ACG CTG CTC GAT CTT GAA AAT AGA GTT GCA CTT GCT     1350
Glu Leu Lys Met Thr Leu Leu Asp Leu Glu Asn Arg Val Ala Leu Ala
            425                 430                 435

CAA CGT CTT TTT CCA ACG GAA GCA CAA GCT GCA ATG GAG ATC GCC GAA     1398
Gln Arg Leu Phe Pro Thr Glu Ala Gln Ala Ala Met Glu Ile Ala Glu
                440                 445                 450

ATG AAG GGA ACA TGT GAG TTC ATA GTG ACT AGC CTC GAG CCT GAC CGT     1446
Met Lys Gly Thr Cys Glu Phe Ile Val Thr Ser Leu Glu Pro Asp Arg
        455                 460                 465

CTC ACT GGT ACG AAG AGA ACA TCA CCG GGT GTA AAG ATA GCA CCT TTC     1494
Leu Thr Gly Thr Lys Arg Thr Ser Pro Gly Val Lys Ile Ala Pro Phe
470                 475                 480

AGA ATC CTA GAA GAG CAT CAA AGT AGA CTA AAA GCG CTT TCT AAA ACC     1542
Arg Ile Leu Glu Glu His Gln Ser Arg Leu Lys Ala Leu Ser Lys Thr
485                 490                 495                 500

GTG GAA CTC GGG AAA CGA TTC TTC CCG CGC TGT TCG GCA GTG CTC GAC     1590
Val Glu Leu Gly Lys Arg Phe Phe Pro Arg Cys Ser Ala Val Leu Asp
            505                 510                 515

CAG ATT ATG AAC TGT GAG GAC TTG ACT CAA CTG GCT TGC GGA GAA GAC     1638
Gln Ile Met Asn Cys Glu Asp Leu Thr Gln Leu Ala Cys Gly Glu Asp
                520                 525                 530

GAC ACT GCT GAG AAA CGA CTA CAA AAG AAG CAA AGG TAC ATG GAA ATA     1686
Asp Thr Ala Glu Lys Arg Leu Gln Lys Lys Gln Arg Tyr Met Glu Ile
        535                 540                 545

CAA GAG ACA CTA AAG AAG GCC TTT AGT GAG GAC AAT TTG GAA TTA GGA     1734
Gln Glu Thr Leu Lys Lys Ala Phe Ser Glu Asp Asn Leu Glu Leu Gly
550                 555                 560

AAT TTG TCC CTG ACA GAT TCG ACT TCT TCC ACA TCG AAA TCA ACC GGT     1782
Asn Leu Ser Leu Thr Asp Ser Thr Ser Ser Thr Ser Lys Ser Thr Gly
565                 570                 575                 580

GGA AAG AGG TCT AAC CGT AAA CTC TCT CAT CGT CGT CGG TGA             1824
Gly Lys Arg Ser Asn Arg Lys Leu Ser His Arg Arg Arg *
            585                 590
```

```
GACTCTTGCC TCTTAGTGTA ATTTTTGCTG TACCATATAA TTCTGTTTTC ATGATGACTG    1884

TAACTGTTTA TGTCTATCGT TGGCGTCATA TAGTTTCGCT CTTCGTTTTG CATCCTGTGT    1944

ATTATTGCTG CAGGTGTGCT TCAAACAAAT GTTGTAACAA TTTGAACCAA TGGTATACAG    2004

ATTTGTA                                                              2011
```

(2) INFORMATION FOR SEQ ID NO:8:

(i) SEQUENCE CHARACTERISTICS:
        (A) LENGTH: 593 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asp Thr Thr Ile Asp Gly Phe Ala Asp Ser Tyr Glu Ile Ser Ser
 1               5                  10                  15

Thr Ser Phe Val Ala Thr Asp Asn Thr Asp Ser Ser Ile Val Tyr Leu
                20                  25                  30

Ala Ala Glu Gln Val Leu Thr Gly Pro Asp Val Ser Ala Leu Gln Leu
            35                  40                  45

Leu Ser Asn Ser Phe Glu Ala Val Phe Asp Ala Pro Asp Asp Phe Tyr
        50                  55                  60

Ser Asp Ala Lys Leu Val Leu Ser Asp Gly Arg Glu Val Ser Phe His
65                  70                  75                  80

Arg Cys Val Leu Ser Ala Arg Ser Ser Phe Lys Ser Ala Leu Ala
                    85                  90                  95

Ala Ala Lys Lys Glu Lys Asp Ser Asn Asn Thr Ala Ala Val Lys Leu
                100                 105                 110

Glu Leu Lys Glu Ile Ala Lys Asp Tyr Glu Val Gly Phe Asp Ser Val
            115                 120                 125

Val Thr Val Leu Ala Tyr Val Tyr Ser Ser Arg Val Arg Pro Pro Pro
        130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
                180                 185                 190

Val Val Asp Lys Val Val Ile Glu Asp Thr Leu Val Ile Leu Lys Leu
            195                 200                 205

Ala Asn Ile Cys Gly Lys Ala Cys Met Lys Leu Leu Asp Arg Cys Lys
        210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255

Gly Leu Glu Val Pro Lys Val Lys Lys His Val Ser Asn Val His Lys
                260                 265                 270

Ala Leu Asp Ser Asp Asp Ile Glu Leu Val Lys Leu Leu Leu Lys Glu
            275                 280                 285

Asp His Thr Asn Leu Asp Asp Ala Cys Ala Leu His Phe Ala Val Ala
        290                 295                 300
```

```
Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
                325                 330                 335

Ala Met Arg Lys Glu Pro Gln Leu Ile Leu Ser Leu Leu Glu Lys Gly
            340                 345                 350

Ala Ser Ala Ser Glu Ala Thr Leu Glu Gly Arg Thr Ala Leu Met Ile
        355                 360                 365

Ala Lys Gln Ala Thr Met Ala Val Glu Cys Asn Asn Ile Pro Glu Gln
    370                 375                 380

Cys Lys His Ser Leu Lys Gly Arg Leu Cys Val Glu Ile Leu Glu Gln
385                 390                 395                 400

Glu Asp Lys Arg Glu Gln Ile Pro Arg Asp Val Pro Pro Ser Phe Ala
                405                 410                 415

Val Ala Ala Asp Glu Leu Lys Met Thr Leu Leu Asp Leu Glu Asn Arg
            420                 425                 430

Val Ala Leu Ala Gln Arg Leu Phe Pro Thr Glu Ala Gln Ala Ala Met
        435                 440                 445

Glu Ile Ala Glu Met Lys Gly Thr Cys Glu Phe Ile Val Thr Ser Leu
    450                 455                 460

Glu Pro Asp Arg Leu Thr Gly Thr Lys Arg Thr Ser Pro Gly Val Lys
465                 470                 475                 480

Ile Ala Pro Phe Arg Ile Leu Glu Glu His Gln Ser Arg Leu Lys Ala
                485                 490                 495

Leu Ser Lys Thr Val Glu Leu Gly Lys Arg Phe Phe Pro Arg Cys Ser
            500                 505                 510

Ala Val Leu Asp Gln Ile Met Asn Cys Glu Asp Leu Thr Gln Leu Ala
        515                 520                 525

Cys Gly Glu Asp Asp Thr Ala Gly Lys Arg Leu Gln Lys Lys Gln Arg
    530                 535                 540

Tyr Met Glu Ile Gln Glu Thr Leu Lys Lys Ala Phe Ser Glu Asp Asn
545                 550                 555                 560

Leu Glu Leu Gly Asn Leu Ser Leu Thr Asp Ser Thr Ser Ser Thr Ser
                565                 570                 575

Lys Ser Thr Gly Gly Lys Arg Ser Asn Arg Lys Leu Ser His Arg Arg
            580                 585                 590

Arg (2) INFORMATION FOR SEQ ID NO:9:

(i) SEQUENCE CHARACTERISTICS:
        (A) LENGTH: 1597 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1410
        (D) OTHER INFORMATION: /product= "Altered form of NIM1"
            /note= "N-terminal deletion compared to wild-type NIM1
            sequence."
```

(xi) SEQUENCE DESCRIPTION: SEQ ID NO:9:

| | | | | | | | | | | | | | | | | |
|---|---|---|---|---|---|---|---|---|---|---|---|---|---|---|---|---|
| ATG | GAT | TCG | GTT | GTG | ACT | GTT | TTG | GCT | TAT | GTT | TAC | AGC | AGC | AGA | GTG | 48 |
| Met | Asp | Ser | Val | Val | Thr | Val | Leu | Ala | Tyr | Val | Tyr | Ser | Ser | Arg | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AGA | CCG | CCG | CCT | AAA | GGA | GTT | TCT | GAA | TGC | GCA | GAC | GAG | AAT | TGC | TGC | 96 |
| Arg | Pro | Pro | Pro | Lys | Gly | Val | Ser | Glu | Cys | Ala | Asp | Glu | Asn | Cys | Cys | |
| | | | 20 | | | | | 25 | | | | | 30 | | | |

| | | | | | | | | | | | | | | | | |
|---|---|---|---|---|---|---|---|---|---|---|---|---|---|---|---|---|
| CAC | GTG | GCT | TGC | CGG | CCG | GCG | GTG | GAT | TTC | ATG | TTG | GAG | GTT | CTC | TAT | 144 |
| His | Val | Ala | Cys | Arg | Pro | Ala | Val | Asp | Phe | Met | Leu | Glu | Val | Leu | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| TTG | GCT | TTC | ATC | TTC | AAG | ATC | CCT | GAA | TTA | ATT | ACT | CTC | TAT | CAG | AGG | 192 |
| Leu | Ala | Phe | Ile | Phe | Lys | Ile | Pro | Glu | Leu | Ile | Thr | Leu | Tyr | Gln | Arg | |
| | 50 | | | | | 55 | | | | | 60 | | | | | |

| | | | | | | | | | | | | | | | | |
|---|---|---|---|---|---|---|---|---|---|---|---|---|---|---|---|---|
| CAC | TTA | TTG | GAC | GTT | GTA | GAC | AAA | GTT | GTT | ATA | GAG | GAC | ACA | TTG | GTT | 240 |
| His | Leu | Leu | Asp | Val | Val | Asp | Lys | Val | Val | Ile | Glu | Asp | Thr | Leu | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ATA | CTC | AAG | CTT | GCT | AAT | ATA | TGT | GGT | AAA | GCT | TGT | ATG | AAG | CTA | TTG | 288 |
| Ile | Leu | Lys | Leu | Ala | Asn | Ile | Cys | Gly | Lys | Ala | Cys | Met | Lys | Leu | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| GAT | AGA | TGT | AAA | GAG | ATT | ATT | GTC | AAG | TCT | AAT | GTA | GAT | ATG | GTT | AGT | 336 |
| Asp | Arg | Cys | Lys | Glu | Ile | Ile | Val | Lys | Ser | Asn | Val | Asp | Met | Val | Ser | |
| | | 100 | | | | | 105 | | | | | 110 | | | | |

| | | | | | | | | | | | | | | | | |
|---|---|---|---|---|---|---|---|---|---|---|---|---|---|---|---|---|
| CTT | GAA | AAG | TCA | TTG | CCG | GAA | GAG | CTT | GTT | AAA | GAG | ATA | ATT | GAT | AGA | 384 |
| Leu | Glu | Lys | Ser | Leu | Pro | Glu | Glu | Leu | Val | Lys | Glu | Ile | Ile | Asp | Arg | |
| | | | 115 | | | | | 120 | | | | | 125 | | | |

| | | | | | | | | | | | | | | | | |
|---|---|---|---|---|---|---|---|---|---|---|---|---|---|---|---|---|
| CGT | AAA | GAG | CTT | GGT | TTG | GAG | GTA | CCT | AAA | GTA | AAG | AAA | CAT | GTC | TCG | 432 |
| Arg | Lys | Glu | Leu | Gly | Leu | Glu | Val | Pro | Lys | Val | Lys | Lys | His | Val | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| AAT | GTA | CAT | AAG | GCA | CTT | GAC | TCG | GAT | GAT | ATT | GAG | TTA | GTC | AAG | TTG | 480 |
| Asn | Val | His | Lys | Ala | Leu | Asp | Ser | Asp | Asp | Ile | Glu | Leu | Val | Lys | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| CTT | TTG | AAA | GAG | GAT | CAC | ACC | AAT | CTA | GAT | GAT | GCG | TGT | GCT | CTT | CAT | 528 |
| Leu | Leu | Lys | Glu | Asp | His | Thr | Asn | Leu | Asp | Asp | Ala | Cys | Ala | Leu | His | |
| | | | | 165 | | | | | 170 | | | | | 175 | | |

| | | | | | | | | | | | | | | | | |
|---|---|---|---|---|---|---|---|---|---|---|---|---|---|---|---|---|
| TTC | GCT | GTT | GCA | TAT | TGC | AAT | GTG | AAG | ACC | GCA | ACA | GAT | CTT | TTA | AAA | 576 |
| Phe | Ala | Val | Ala | Tyr | Cys | Asn | Val | Lys | Thr | Ala | Thr | Asp | Leu | Leu | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| CTT | GAT | CTT | GCC | GAT | GTC | AAC | CAT | AGG | AAT | CCG | AGG | GGA | TAT | ACG | GTG | 624 |
| Leu | Asp | Leu | Ala | Asp | Val | Asn | His | Arg | Asn | Pro | Arg | Gly | Tyr | Thr | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| CTT | CAT | GTT | GCT | GCG | ATG | CGG | AAG | GAG | CCA | CAA | TTG | ATA | CTA | TCT | CTA | 672 |
| Leu | His | Val | Ala | Ala | Met | Arg | Lys | Glu | Pro | Gln | Leu | Ile | Leu | Ser | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| TTG | GAA | AAA | GGT | GCA | AGT | GCA | TCA | GAA | GCA | ACT | TTG | GAA | GGT | AGA | ACC | 720 |
| Leu | Glu | Lys | Gly | Ala | Ser | Ala | Ser | Glu | Ala | Thr | Leu | Glu | Gly | Arg | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GCA | CTC | ATG | ATC | GCA | AAA | CAA | GCC | ACT | ATG | GCG | GTT | GAA | TGT | AAT | AAT | 768 |
| Ala | Leu | Met | Ile | Ala | Lys | Gln | Ala | Thr | Met | Ala | Val | Glu | Cys | Asn | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| ATC | CCG | GAG | CAA | TGC | AAG | CAT | TCT | CTC | AAA | GGC | CGA | CTA | TGT | GTA | GAA | 816 |
| Ile | Pro | Glu | Gln | Cys | Lys | His | Ser | Leu | Lys | Gly | Arg | Leu | Cys | Val | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
| ATA | CTA | GAG | CAA | GAA | GAC | AAA | CGA | GAA | CAA | ATT | CCT | AGA | GAT | GTT | CCT | 864 |
| Ile | Leu | Glu | Gln | Glu | Asp | Lys | Arg | Glu | Gln | Ile | Pro | Arg | Asp | Val | Pro | |
| | | 275 | | | | | 280 | | | | | 285 | | | | |

| | | | | | | | | | | | | | | | | |
|---|---|---|---|---|---|---|---|---|---|---|---|---|---|---|---|---|
| CCC | TCT | TTT | GCA | GTG | GCG | GCC | GAT | GAA | TTG | AAG | ATG | ACG | CTG | CTC | GAT | 912 |
| Pro | Ser | Phe | Ala | Val | Ala | Ala | Asp | Glu | Leu | Lys | Met | Thr | Leu | Leu | Asp | |
| | 290 | | | | | 295 | | | | | 300 | | | | | |

```
CTT GAA AAT AGA GTT GCA CTT GCT CAA CGT CTT TTT CCA ACG GAA GCA        960
Leu Glu Asn Arg Val Ala Leu Ala Gln Arg Leu Phe Pro Thr Glu Ala
305                 310                 315                 320

CAA GCT GCA ATG GAG ATC GCC GAA ATG AAG GGA ACA TGT GAG TTC ATA       1008
Gln Ala Ala Met Glu Ile Ala Glu Met Lys Gly Thr Cys Glu Phe Ile
                325                 330                 335

GTG ACT AGC CTC GAG CCT GAC CGT CTC ACT GGT ACG AAG AGA ACA TCA       1056
Val Thr Ser Leu Glu Pro Asp Arg Leu Thr Gly Thr Lys Arg Thr Ser
            340                 345                 350

CCG GGT GTA AAG ATA GCA CCT TTC AGA ATC CTA GAA GAG CAT CAA AGT       1104
Pro Gly Val Lys Ile Ala Pro Phe Arg Ile Leu Glu Glu His Gln Ser
        355                 360                 365

AGA CTA AAA GCG CTT TCT AAA ACC GTG GAA CTC GGG AAA CGA TTC TTC       1152
Arg Leu Lys Ala Leu Ser Lys Thr Val Glu Leu Gly Lys Arg Phe Phe
370                 375                 380

CCG CGC TGT TCG GCA GTG CTC GAC CAG ATT ATG AAC TGT GAG GAC TTG       1200
Pro Arg Cys Ser Ala Val Leu Asp Gln Ile Met Asn Cys Glu Asp Leu
385                 390                 395                 400

ACT CAA CTG GCT TGC GGA GAA GAC GAC ACT GCT GAG AAA CGA CTA CAA       1248
Thr Gln Leu Ala Cys Gly Glu Asp Asp Thr Ala Glu Lys Arg Leu Gln
                405                 410                 415

AAG AAG CAA AGG TAC ATG GAA ATA CAA GAG ACA CTA AAG AAG GCC TTT       1296
Lys Lys Gln Arg Tyr Met Glu Ile Gln Glu Thr Leu Lys Lys Ala Phe
            420                 425                 430

AGT GAG GAC AAT TTG GAA TTA GGA AAT TTG TCC CTG ACA GAT TCG ACT       1344
Ser Glu Asp Asn Leu Glu Leu Gly Asn Leu Ser Leu Thr Asp Ser Thr
        435                 440                 445

TCT TCC ACA TCG AAA TCA ACC GGT GGA AAG AGG TCT AAC CGT AAA CTC       1392
Ser Ser Thr Ser Lys Ser Thr Gly Gly Lys Arg Ser Asn Arg Lys Leu
450                 455                 460

TCT CAT CGT CGT CGG TGA GACTCTTGCC TCTTAGTGTA ATTTTTGCTG              1440
Ser His Arg Arg Arg *
465                 470

TACCATATAA TTCTGTTTTC ATGATGACTG TAACTGTTTA TGTCTATCGT TGGCGTCATA     1500

TAGTTTCGCT CTTCGTTTTG CATCCTGTGT ATTATTGCTG CAGGTGTGCT TCAAACAAAT     1560

GTTGTAACAA TTTGAACCAA TGGTATACAG ATTTGTA                              1597

(2) INFORMATION FOR SEQ ID NO:10:

(i) SEQUENCE CHARACTERISTICS:
        (A) LENGTH:  469 amino acids
        (B) TYPE: amino acid
        (D) TOPOLOGY: linear (ii) MOLECULE TYPE: protein (xi) SEQUENCE DESCRIPTION: SEQ ID NO:10:

Met Asp Ser Val Val Thr Val Leu Ala Tyr Val Tyr Ser Ser Arg Val
 1               5                  10                  15

Arg Pro Pro Lys Gly Val Ser Glu Cys Ala Asp Glu Asn Cys Cys
                20                  25                  30

His Val Ala Cys Arg Pro Ala Val Asp Phe Met Leu Glu Val Leu Tyr
            35                  40                  45

Leu Ala Phe Ile Phe Lys Ile Pro Glu Leu Ile Thr Leu Tyr Gln Arg
        50                  55                  60

His Leu Leu Asp Val Val Asp Lys Val Val Ile Glu Asp Thr Leu Val
65                  70                  75                  80
```

-continued

```
Ile Leu Lys Leu Ala Asn Ile Cys Gly Lys Ala Cys Met Lys Leu Leu
                 85                  90                  95

Asp Arg Cys Lys Glu Ile Ile Val Lys Ser Asn Val Asp Met Val Ser
                100                 105                 110

Leu Glu Lys Ser Leu Pro Glu Leu Val Lys Glu Ile Ile Asp Arg
            115                 120                 125

Arg Lys Glu Leu Gly Leu Glu Val Pro Lys Val Lys His Val Ser
        130                 135                 140

Asn Val His Lys Ala Leu Asp Ser Asp Ile Glu Leu Val Lys Leu
145                 150                 155                 160

Leu Leu Lys Glu Asp His Thr Asn Leu Asp Asp Ala Cys Ala Leu His
                165                 170                 175

Phe Ala Val Ala Tyr Cys Asn Val Lys Thr Ala Thr Asp Leu Leu Lys
                180                 185                 190

Leu Asp Leu Ala Asp Val Asn His Arg Asn Pro Arg Gly Tyr Thr Val
            195                 200                 205

Leu His Val Ala Ala Met Arg Lys Glu Pro Gln Leu Ile Leu Ser Leu
        210                 215                 220

Leu Glu Lys Gly Ala Ser Ala Ser Glu Ala Thr Leu Glu Gly Arg Thr
225                 230                 235                 240

Ala Leu Met Ile Ala Lys Gln Ala Thr Met Ala Val Glu Cys Asn Asn
                245                 250                 255

Ile Pro Glu Gln Cys Lys His Ser Leu Lys Gly Arg Leu Cys Val Glu
                260                 265                 270

Ile Leu Glu Gln Glu Asp Lys Arg Glu Gln Ile Pro Arg Asp Val Pro
            275                 280                 285

Pro Ser Phe Ala Val Ala Ala Asp Glu Leu Lys Met Thr Leu Leu Asp
        290                 295                 300

Leu Glu Asn Arg Val Ala Leu Ala Gln Arg Leu Phe Pro Thr Glu Ala
305                 310                 315                 320

Gln Ala Ala Met Glu Ile Ala Glu Met Lys Gly Thr Cys Glu Phe Ile
                325                 330                 335

Val Thr Ser Leu Glu Pro Asp Arg Leu Thr Gly Thr Lys Arg Thr Ser
                340                 345                 350

Pro Gly Val Lys Ile Ala Pro Phe Arg Ile Leu Glu Glu His Gln Ser
            355                 360                 365

Arg Leu Lys Ala Leu Ser Lys Thr Val Glu Leu Gly Lys Arg Phe Phe
        370                 375                 380

Pro Arg Cys Ser Ala Val Leu Asp Gln Ile Met Asn Cys Glu Asp Leu
385                 390                 395                 400

Thr Gln Leu Ala Cys Gly Glu Asp Thr Ala Glu Lys Arg Leu Gln
                405                 410                 415

Lys Lys Gln Arg Tyr Met Glu Ile Gln Glu Thr Leu Lys Lys Ala Phe
                420                 425                 430

Ser Glu Asp Asn Leu Glu Leu Gly Asn Leu Ser Leu Thr Asp Ser Thr
            435                 440                 445

Ser Ser Thr Ser Lys Ser Thr Gly Gly Lys Arg Ser Asn Arg Lys Leu
        450                 455                 460

Ser His Arg Arg Arg
465             470
```

(2) INFORMATION FOR SEQ ID NO:11:

(i) SEQUENCE CHARACTERISTICS:
        (A) LENGTH: 1608 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 43..1608
        (D) OTHER INFORMATION: /product= "Altered form of NIM1"
            /note= "C-terminal deletion compared to wild-type NIM1."

(xi) SEQUENCE DESCRIPTION: SEQ ID NO:11:

```
GATCTCTTTA ATTTGTGAAT TTCAATTCAT CGGAACCTGT TG ATG GAC ACC ACC         54
                                              Met Asp Thr Thr
                                               1

ATT GAT GGA TTC GCC GAT TCT TAT GAA ATC AGC AGC ACT AGT TTC GTC       102
Ile Asp Gly Phe Ala Asp Ser Tyr Glu Ile Ser Ser Thr Ser Phe Val
 5              10                  15                  20

GCT ACC GAT AAC ACC GAC TCC TCT ATT GTT TAT CTG GCC GCC GAA CAA       150
Ala Thr Asp Asn Thr Asp Ser Ser Ile Val Tyr Leu Ala Ala Glu Gln
            25                  30                  35

GTA CTC ACC GGA CCT GAT GTA TCT GCT CTG CAA TTG CTC TCC AAC AGC       198
Val Leu Thr Gly Pro Asp Val Ser Ala Leu Gln Leu Leu Ser Asn Ser
        40                  45                  50

TTC GAA TCC GTC TTT GAC TCG CCG GAT GAT TTC TAC AGC GAC GCT AAG       246
Phe Glu Ser Val Phe Asp Ser Pro Asp Asp Phe Tyr Ser Asp Ala Lys
    55                  60                  65

CTT GTT CTC TCC GAC GGC CGG GAA GTT TCT TTC CAC CGG TGC GTT TTG       294
Leu Val Leu Ser Asp Gly Arg Glu Val Ser Phe His Arg Cys Val Leu
 70                 75                  80

TCA GCG AGA AGC TCT TTC TTC AAG AGC GCT TTA GCC GCC GCT AAG AAG       342
Ser Ala Arg Ser Ser Phe Phe Lys Ser Ala Leu Ala Ala Ala Lys Lys
 85                 90                  95                 100

GAG AAA GAC TCC AAC AAC ACC GCC GCC GTG AAG CTC GAG CTT AAG GAG       390
Glu Lys Asp Ser Asn Asn Thr Ala Ala Val Lys Leu Glu Leu Lys Glu
                105                 110                 115

ATT GCC AAG GAT TAC GAA GTC GGT TTC GAT TCG GTT GTG ACT GTT TTG       438
Ile Ala Lys Asp Tyr Glu Val Gly Phe Asp Ser Val Val Thr Val Leu
            120                 125                 130

GCT TAT GTT TAC AGC AGC AGA GTG AGA CCG CCG CCT AAA GGA GTT TCT       486
Ala Tyr Val Tyr Ser Ser Arg Val Arg Pro Pro Pro Lys Gly Val Ser
        135                 140                 145

GAA TGC GCA GAC GAG AAT TGC TGC CAC GTG GCT TGC CGG CCG GCG GTG       534
Glu Cys Ala Asp Glu Asn Cys Cys His Val Ala Cys Arg Pro Ala Val
    150                 155                 160

GAT TTC ATG TTG GAG GTT CTC TAT TTG GCT TTC ATC TTC AAG ATC CCT       582
Asp Phe Met Leu Glu Val Leu Tyr Leu Ala Phe Ile Phe Lys Ile Pro
165                 170                 175                 180

GAA TTA ATT ACT CTC TAT CAG AGG CAC TTA TTG GAC GTT GTA GAC AAA       630
Glu Leu Ile Thr Leu Tyr Gln Arg His Leu Leu Asp Val Val Asp Lys
                185                 190                 195

GTT GTT ATA GAG GAC ACA TTG GTT ATA CTC AAG CTT GCT AAT ATA TGT       678
Val Val Ile Glu Asp Thr Leu Val Ile Leu Lys Leu Ala Asn Ile Cys
            200                 205                 210

GGT AAA GCT TGT ATG AAG CTA TTG GAT AGA TGT AAA GAG ATT ATT GTC       726
Gly Lys Ala Cys Met Lys Leu Leu Asp Arg Cys Lys Glu Ile Ile Val
        215                 220                 225
```

```
AAG TCT AAT GTA GAT ATG GTT AGT CTT GAA AAG TCA TTG CCG GAA GAG      774
Lys Ser Asn Val Asp Met Val Ser Leu Glu Lys Ser Leu Pro Glu Glu
    230                 235                 240

CTT GTT AAA GAG ATA ATT GAT AGA CGT AAA GAG CTT GGT TTG GAG GTA      822
Leu Val Lys Glu Ile Ile Asp Arg Arg Lys Glu Leu Gly Leu Glu Val
245                 250                 255                 260

CCT AAA GTA AAG AAA CAT GTC TCG AAT GTA CAT AAG GCA CTT GAC TCG      870
Pro Lys Val Lys Lys His Val Ser Asn Val His Lys Ala Leu Asp Ser
                265                 270                 275

GAT GAT ATT GAG TTA GTC AAG TTG CTT TTG AAA GAG GAT CAC ACC AAT      918
Asp Asp Ile Glu Leu Val Lys Leu Leu Leu Lys Glu Asp His Thr Asn
            280                 285                 290

CTA GAT GAT GCG TGT GCT CTT CAT TTC GCT GTT GCA TAT TGC AAT GTG      966
Leu Asp Asp Ala Cys Ala Leu His Phe Ala Val Ala Tyr Cys Asn Val
        295                 300                 305

AAG ACC GCA ACA GAT CTT TTA AAA CTT GAT CTT GCC GAT GTC AAC CAT     1014
Lys Thr Ala Thr Asp Leu Leu Lys Leu Asp Leu Ala Asp Val Asn His
    310                 315                 320

AGG AAT CCG AGG GGA TAT ACG GTG CTT CAT GTT GCT GCG ATG CGG AAG     1062
Arg Asn Pro Arg Gly Tyr Thr Val Leu His Val Ala Ala Met Arg Lys
325                 330                 335                 340

GAG CCA CAA TTG ATA CTA TCT CTA TTG GAA AAA GGT GCA AGT GCA TCA     1110
Glu Pro Gln Leu Ile Leu Ser Leu Leu Glu Lys Gly Ala Ser Ala Ser
                345                 350                 355

GAA GCA ACT TTG GAA GGT AGA ACC GCA CTC ATG ATC GCA AAA CAA GCC     1158
Glu Ala Thr Leu Glu Gly Arg Thr Ala Leu Met Ile Ala Lys Gln Ala
            360                 365                 370

ACT ATG GCG GTT GAA TGT AAT AAT ATC CCG GAG CAA TGC AAG CAT TCT     1206
Thr Met Ala Val Glu Cys Asn Asn Ile Pro Glu Gln Cys Lys His Ser
        375                 380                 385

CTC AAA GGC CGA CTA TGT GTA GAA ATA CTA GAG CAA GAA GAC AAA CGA     1254
Leu Lys Gly Arg Leu Cys Val Glu Ile Leu Glu Gln Glu Asp Lys Arg
    390                 395                 400

GAA CAA ATT CCT AGA GAT GTT CCT CCC TCT TTT GCA GTG GCG GCC GAT     1302
Glu Gln Ile Pro Arg Asp Val Pro Pro Ser Phe Ala Val Ala Ala Asp
405                 410                 415                 420

GAA TTG AAG ATG ACG CTG CTC GAT CTT GAA AAT AGA GTT GCA CTT GCT     1350
Glu Leu Lys Met Thr Leu Leu Asp Leu Glu Asn Arg Val Ala Leu Ala
                425                 430                 435

CAA CGT CTT TTT CCA ACG GAA GCA CAA GCT GCA ATG GAG ATC GCC GAA     1398
Gln Arg Leu Phe Pro Thr Glu Ala Gln Ala Ala Met Glu Ile Ala Glu
            440                 445                 450

ATG AAG GGA ACA TGT GAG TTC ATA GTG ACT AGC CTC GAG CCT GAC CGT     1446
Met Lys Gly Thr Cys Glu Phe Ile Val Thr Ser Leu Glu Pro Asp Arg
        455                 460                 465

CTC ACT GGT ACG AAG AGA ACA TCA CCG GGT GTA AAG ATA GCA CCT TTC     1494
Leu Thr Gly Thr Lys Arg Thr Ser Pro Gly Val Lys Ile Ala Pro Phe
    470                 475                 480

AGA ATC CTA GAA GAG CAT CAA AGT AGA CTA AAA GCG CTT TCT AAA ACC     1542
Arg Ile Leu Glu Glu His Gln Ser Arg Leu Lys Ala Leu Ser Lys Thr
485                 490                 495                 500

GTG GAA CTC GGG AAA CGA TTC TTC CCG CGC TGT TCG GCA GTG CTC GAC     1590
Val Glu Leu Gly Lys Arg Phe Phe Pro Arg Cys Ser Ala Val Leu Asp
                505                 510                 515

CAG ATT ATG AAC TGT TGA                                             1608
Gln Ile Met Asn Cys  *
            520
```

-continued (2) INFORMATION FOR SEQ ID NO:12:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:12:

```
Met Asp Thr Thr Ile Asp Gly Phe Ala Asp Ser Tyr Glu Ile Ser Ser
 1               5                  10                  15

Thr Ser Phe Val Ala Thr Asp Asn Thr Asp Ser Ser Ile Val Tyr Leu
                20                  25                  30

Ala Ala Glu Gln Val Leu Thr Gly Pro Asp Val Ser Ala Leu Gln Leu
            35                  40                  45

Leu Ser Asn Ser Phe Glu Ser Val Phe Asp Ser Pro Asp Asp Phe Tyr
        50                  55                  60

Ser Asp Ala Lys Leu Val Leu Ser Asp Gly Arg Glu Val Ser Phe His
 65                  70                  75                  80

Arg Cys Val Leu Ser Ala Arg Ser Ser Phe Phe Lys Ser Ala Leu Ala
                85                  90                  95

Ala Ala Lys Lys Glu Lys Asp Ser Asn Asn Thr Ala Ala Val Lys Leu
            100                 105                 110

Glu Leu Lys Glu Ile Ala Lys Asp Tyr Glu Val Gly Phe Asp Ser Val
        115                 120                 125

Val Thr Val Leu Ala Tyr Val Tyr Ser Ser Arg Val Arg Pro Pro Pro
130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
            180                 185                 190

Val Val Asp Lys Val Ile Glu Asp Thr Leu Val Ile Leu Lys Leu
        195                 200                 205

Ala Asn Ile Cys Gly Lys Ala Cys Met Lys Leu Leu Asp Arg Cys Lys
210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255

Gly Leu Glu Val Pro Lys Val Lys Lys His Val Ser Asn Val His Lys
            260                 265                 270

Ala Leu Asp Ser Asp Asp Ile Glu Leu Val Lys Leu Leu Leu Lys Glu
        275                 280                 285

Asp His Thr Asn Leu Asp Asp Ala Cys Ala Leu His Phe Ala Val Ala
    290                 295                 300

Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
                325                 330                 335

Ala Met Arg Lys Glu Pro Gln Leu Ile Leu Ser Leu Leu Glu Lys Gly
            340                 345                 350
```

```
Ala Ser Ala Ser Glu Ala Thr Leu Glu Gly Arg Thr Ala Leu Met Ile
        355                 360                 365

Ala Lys Gln Ala Thr Met Ala Val Glu Cys Asn Asn Ile Pro Glu Gln
370                 375                 380

Cys Lys His Ser Leu Lys Gly Arg Leu Cys Val Glu Ile Leu Glu Gln
385                 390                 395                 400

Glu Asp Lys Arg Glu Gln Ile Pro Arg Asp Val Pro Pro Ser Phe Ala
                405                 410                 415

Val Ala Ala Asp Glu Leu Lys Met Thr Leu Leu Asp Leu Glu Asn Arg
                420                 425                 430

Val Ala Leu Ala Gln Arg Leu Phe Pro Thr Glu Ala Gln Ala Ala Met
        435                 440                 445

Glu Ile Ala Glu Met Lys Gly Thr Cys Glu Phe Ile Val Thr Ser Leu
        450                 455                 460

Glu Pro Asp Arg Leu Thr Gly Thr Lys Arg Thr Ser Pro Gly Val Lys
465                 470                 475                 480

Ile Ala Pro Phe Arg Ile Leu Glu Glu His Gln Ser Arg Leu Lys Ala
                485                 490                 495

Leu Ser Lys Thr Val Glu Leu Gly Lys Arg Phe Phe Pro Arg Cys Ser
                500                 505                 510

Ala Val Leu Asp Gln Ile Met Asn Cys
                515                 520

(2) INFORMATION FOR SEQ ID NO:13:

(i) SEQUENCE CHARACTERISTICS:
        (A) LENGTH: 1194 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1194
        (D) OTHER INFORMATION: /product= "Altered form of NIM1"
            /note= "N-terminal/C-terminal chimera."

(xi) SEQUENCE DESCRIPTION: SEQ ID NO:13:

ATG GAT TCG GTT GTG ACT GTT TTG GCT TAT GTT TAC AGC AGC AGA GTG        48
Met Asp Ser Val Val Thr Val Leu Ala Tyr Val Tyr Ser Ser Arg Val
 1               5                  10                  15

AGA CCG CCG CCT AAA GGA GTT TCT GAA TGC GCA GAC GAG AAT TGC TGC        96
Arg Pro Pro Pro Lys Gly Val Ser Glu Cys Ala Asp Glu Asn Cys Cys
             20                  25                  30

CAC GTG GCT TGC CGG CCG GCG GTG GAT TTC ATG TTG GAG GTT CTC TAT       144
His Val Ala Cys Arg Pro Ala Val Asp Phe Met Leu Glu Val Leu Tyr
         35                  40                  45

TTG GCT TTC ATC TTC AAG ATC CCT GAA TTA ATT ACT CTC TAT CAG AGG       192
Leu Ala Phe Ile Phe Lys Ile Pro Glu Leu Ile Thr Leu Tyr Gln Arg
 50                  55                  60

CAC TTA TTG GAC GTT GTA GAC AAA GTT GTT ATA GAG GAC ACA TTG GTT       240
His Leu Leu Asp Val Val Asp Lys Val Val Ile Glu Asp Thr Leu Val
 65                  70                  75                  80

ATA CTC AAG CTT GCT AAT ATA TGT GGT AAA GCT TGT ATG AAG CTA TTG       288
Ile Leu Lys Leu Ala Asn Ile Cys Gly Lys Ala Cys Met Lys Leu Leu
                 85                  90                  95
```

```
GAT AGA TGT AAA GAG ATT ATT GTC AAG TCT AAT GTA GAT ATG GTT AGT        336
Asp Arg Cys Lys Glu Ile Ile Val Lys Ser Asn Val Asp Met Val Ser
        100                 105                 110

CTT GAA AAG TCA TTG CCG GAA GAG CTT GTT AAA GAG ATA ATT GAT AGA        384
Leu Glu Lys Ser Leu Pro Glu Glu Leu Val Lys Glu Ile Ile Asp Arg
            115                 120                 125

CGT AAA GAG CTT GGT TTG GAG GTA CCT AAA GTA AAG AAA CAT GTC TCG        432
Arg Lys Glu Leu Gly Leu Glu Val Pro Lys Val Lys Lys His Val Ser
    130                 135                 140

AAT GTA CAT AAG GCA CTT GAC TCG GAT GAT ATT GAG TTA GTC AAG TTG        480
Asn Val His Lys Ala Leu Asp Ser Asp Asp Ile Glu Leu Val Lys Leu
145                 150                 155                 160

CTT TTG AAA GAG GAT CAC ACC AAT CTA GAT GAT GCG TGT GCT CTT CAT        528
Leu Leu Lys Glu Asp His Thr Asn Leu Asp Asp Ala Cys Ala Leu His
                165                 170                 175

TTC GCT GTT GCA TAT TGC AAT GTG AAG ACC GCA ACA GAT CTT TTA AAA        576
Phe Ala Val Ala Tyr Cys Asn Val Lys Thr Ala Thr Asp Leu Leu Lys
            180                 185                 190

CTT GAT CTT GCC GAT GTC AAC CAT AGG AAT CCG AGG GGA TAT ACG GTG        624
Leu Asp Leu Ala Asp Val Asn His Arg Asn Pro Arg Gly Tyr Thr Val
    195                 200                 205

CTT CAT GTT GCT GCG ATG CGG AAG GAG CCA CAA TTG ATA CTA TCT CTA        672
Leu His Val Ala Ala Met Arg Lys Glu Pro Gln Leu Ile Leu Ser Leu
210                 215                 220

TTG GAA AAA GGT GCA AGT GCA TCA GAA GCA ACT TTG GAA GGT AGA ACC        720
Leu Glu Lys Gly Ala Ser Ala Ser Glu Ala Thr Leu Glu Gly Arg Thr
225                 230                 235                 240

GCA CTC ATG ATC GCA AAA CAA GCC ACT ATG GCG GTT GAA TGT AAT AAT        768
Ala Leu Met Ile Ala Lys Gln Ala Thr Met Ala Val Glu Cys Asn Asn
                245                 250                 255

ATC CCG GAG CAA TGC AAG CAT TCT CTC AAA GGC CGA CTA TGT GTA GAA        816
Ile Pro Glu Gln Cys Lys His Ser Leu Lys Gly Arg Leu Cys Val Glu
            260                 265                 270

ATA CTA GAG CAA GAA GAC AAA CGA GAA CAA ATT CCT AGA GAT GTT CCT        864
Ile Leu Glu Gln Glu Asp Lys Arg Glu Gln Ile Pro Arg Asp Val Pro
    275                 280                 285

CCC TCT TTT GCA GTG GCG GCC GAT GAA TTG AAG ATG ACG CTG CTC GAT        912
Pro Ser Phe Ala Val Ala Ala Asp Glu Leu Lys Met Thr Leu Leu Asp
290                 295                 300

CTT GAA AAT AGA GTT GCA CTT GCT CAA CGT CTT TTT CCA ACG GAA GCA        960
Leu Glu Asn Arg Val Ala Leu Ala Gln Arg Leu Phe Pro Thr Glu Ala
305                 310                 315                 320

CAA GCT GCA ATG GAG ATC GCC GAA ATG AAG GGA ACA TGT GAG TTC ATA       1008
Gln Ala Ala Met Glu Ile Ala Glu Met Lys Gly Thr Cys Glu Phe Ile
                325                 330                 335

GTG ACT AGC CTC GAG CCT GAC CGT CTC ACT GGT ACG AAG AGA ACA TCA       1056
Val Thr Ser Leu Glu Pro Asp Arg Leu Thr Gly Thr Lys Arg Thr Ser
            340                 345                 350

CCG GGT GTA AAG ATA GCA CCT TTC AGA ATC CTA GAA GAG CAT CAA AGT       1104
Pro Gly Val Lys Ile Ala Pro Phe Arg Ile Leu Glu Glu His Gln Ser
    355                 360                 365

AGA CTA AAA GCG CTT TCT AAA ACC GTG GAA CTC GGG AAA CGA TTC TTC       1152
Arg Leu Lys Ala Leu Ser Lys Thr Val Glu Leu Gly Lys Arg Phe Phe
370                 375                 380

CCG CGC TGT TCG GCA GTG CTC GAC CAG ATT ATG AAC TGT TGA               1194
Pro Arg Cys Ser Ala Val Leu Asp Gln Ile Met Asn Cys *
385                 390                 395
```

—continued (2) INFORMATION FOR SEQ ID NO:14:

(i) SEQUENCE CHARACTERISTICS:
        (A) LENGTH: 397 amino acids
        (B) TYPE: amino acid
        (D) TOPOLOGY: linear (ii) MOLECULE TYPE: protein (xi) SEQUENCE DESCRIPTION: SEQ ID NO:14:

```
Met Asp Ser Val Val Thr Val Leu Ala Tyr Val Tyr Ser Ser Arg Val
 1               5                  10                  15

Arg Pro Pro Lys Gly Val Ser Glu Cys Ala Asp Glu Asn Cys Cys
             20                  25                  30

His Val Ala Cys Arg Pro Ala Val Asp Phe Met Leu Glu Val Leu Tyr
             35                  40                  45

Leu Ala Phe Ile Phe Lys Ile Pro Glu Leu Ile Thr Leu Tyr Gln Arg
         50                  55                  60

His Leu Leu Asp Val Val Asp Lys Val Val Ile Glu Asp Thr Leu Val
 65                  70                  75                  80

Ile Leu Lys Leu Ala Asn Ile Cys Gly Lys Ala Cys Met Lys Leu Leu
                 85                  90                  95

Asp Arg Cys Lys Glu Ile Ile Val Lys Ser Asn Val Asp Met Val Ser
                100                 105                 110

Leu Glu Lys Ser Leu Pro Glu Glu Leu Val Lys Glu Ile Ile Asp Arg
            115                 120                 125

Arg Lys Glu Leu Gly Leu Glu Val Pro Lys Val Lys Lys His Val Ser
        130                 135                 140

Asn Val His Lys Ala Leu Asp Ser Asp Ile Glu Leu Val Lys Leu
145                 150                 155                 160

Leu Leu Lys Glu Asp His Thr Asn Leu Asp Asp Ala Cys Ala Leu His
                165                 170                 175

Phe Ala Val Ala Tyr Cys Asn Val Lys Thr Ala Thr Asp Leu Leu Lys
                180                 185                 190

Leu Asp Leu Ala Asp Val Asn His Arg Asn Pro Arg Gly Tyr Thr Val
            195                 200                 205

Leu His Val Ala Ala Met Arg Lys Glu Pro Gln Leu Ile Leu Ser Leu
        210                 215                 220

Leu Glu Lys Gly Ala Ser Ala Ser Glu Ala Thr Leu Glu Gly Arg Thr
225                 230                 235                 240

Ala Leu Met Ile Ala Lys Gln Ala Thr Met Ala Val Glu Cys Asn Asn
                245                 250                 255

Ile Pro Glu Gln Cys Lys His Ser Leu Lys Gly Arg Leu Cys Val Glu
                260                 265                 270

Ile Leu Glu Gln Glu Asp Lys Arg Glu Gln Ile Pro Arg Asp Val Pro
            275                 280                 285

Pro Ser Phe Ala Val Ala Ala Asp Glu Leu Lys Met Thr Leu Leu Asp
        290                 295                 300

Leu Glu Asn Arg Val Ala Leu Ala Gln Arg Leu Phe Pro Thr Glu Ala
305                 310                 315                 320

Gln Ala Ala Met Glu Ile Ala Glu Met Lys Gly Thr Cys Glu Phe Ile
                325                 330                 335

Val Thr Ser Leu Glu Pro Asp Arg Leu Thr Gly Thr Lys Arg Thr Ser
                340                 345                 350
```

```
Pro Gly Val Lys Ile Ala Pro Phe Arg Ile Leu Glu Glu His Gln Ser
        355                 360                 365

Arg Leu Lys Ala Leu Ser Lys Thr Val Glu Leu Gly Lys Arg Phe Phe
370                 375                 380

Pro Arg Cys Ser Ala Val Leu Asp Gln Ile Met Asn Cys
385                 390                 395
```

(2) INFORMATION FOR SEQ ID NO:15:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..786
        (D) OTHER INFORMATION: /product= "Altered form of NIM1"
            /note= "Ankyrin domains of NIM1."

(xi) SEQUENCE DESCRIPTION: SEQ ID NO:15:

```
ATG GAC TCC AAC AAC ACC GCC GCC GTG AAG CTC GAG CTT AAG GAG ATT      48
Met Asp Ser Asn Asn Thr Ala Ala Val Lys Leu Glu Leu Lys Glu Ile
 1               5                  10                  15

GCC AAG GAT TAC GAA GTC GGT TTC GAT TCG GTT GTG ACT GTT TTG GCT      96
Ala Lys Asp Tyr Glu Val Gly Phe Asp Ser Val Val Thr Val Leu Ala
                20                  25                  30

TAT GTT TAC AGC AGC AGA GTG AGA CCG CCG CCT AAA GGA GTT TCT GAA     144
Tyr Val Tyr Ser Ser Arg Val Arg Pro Pro Pro Lys Gly Val Ser Glu
            35                  40                  45

TGC GCA GAC GAG AAT TGC TGC CAC GTG GCT TGC CGG CCG GCG GTG GAT     192
Cys Ala Asp Glu Asn Cys Cys His Val Ala Cys Arg Pro Ala Val Asp
        50                  55                  60

TTC ATG TTG GAG GTT CTC TAT TTG GCT TTC ATC TTC AAG ATC CCT GAA     240
Phe Met Leu Glu Val Leu Tyr Leu Ala Phe Ile Phe Lys Ile Pro Glu
 65                  70                  75                  80

TTA ATT ACT CTC TAT CAG AGG CAC TTA TTG GAC GTT GTA GAC AAA GTT     288
Leu Ile Thr Leu Tyr Gln Arg His Leu Leu Asp Val Val Asp Lys Val
                85                  90                  95

GTT ATA GAG GAC ACA TTG GTT ATA CTC AAG CTT GCT AAT ATA TGT GGT     336
Val Ile Glu Asp Thr Leu Val Ile Leu Lys Leu Ala Asn Ile Cys Gly
            100                 105                 110

AAA GCT TGT ATG AAG CTA TTG GAT AGA TGT AAA GAG ATT ATT GTC AAG     384
Lys Ala Cys Met Lys Leu Leu Asp Arg Cys Lys Glu Ile Ile Val Lys
        115                 120                 125

TCT AAT GTA GAT ATG GTT AGT CTT GAA AAG TCA TTG CCG GAA GAG CTT     432
Ser Asn Val Asp Met Val Ser Leu Glu Lys Ser Leu Pro Glu Glu Leu
130                 135                 140

GTT AAA GAG ATA ATT GAT AGA CGT AAA GAG CTT GGT TTG GAG GTA CCT     480
Val Lys Glu Ile Ile Asp Arg Arg Lys Glu Leu Gly Leu Glu Val Pro
145                 150                 155                 160

AAA GTA AAG AAA CAT GTC TCG AAT GTA CAT AAG GCA CTT GAC TCG GAT     528
Lys Val Lys Lys His Val Ser Asn Val His Lys Ala Leu Asp Ser Asp
                165                 170                 175

GAT ATT GAG TTA GTC AAG TTG CTT TTG AAA GAG GAT CAC ACC AAT CTA     576
Asp Ile Glu Leu Val Lys Leu Leu Leu Lys Glu Asp His Thr Asn Leu
            180                 185                 190
```

```
GAT GAT GCG TGT GCT CTT CAT TTC GCT GTT GCA TAT TGC AAT GTG AAG      624
Asp Asp Ala Cys Ala Leu His Phe Ala Val Ala Tyr Cys Asn Val Lys
            195                 200                 205

ACC GCA ACA GAT CTT TTA AAA CTT GAT CTT GCC GAT GTC AAC CAT AGG      672
Thr Ala Thr Asp Leu Leu Lys Leu Asp Leu Ala Asp Val Asn His Arg
    210                 215                 220

AAT CCG AGG GGA TAT ACG GTG CTT CAT GTT GCT GCG ATG CGG AAG GAG      720
Asn Pro Arg Gly Tyr Thr Val Leu His Val Ala Ala Met Arg Lys Glu
225                 230                 235                 240

CCA CAA TTG ATA CTA TCT CTA TTG GAA AAA GGT GCA AGT GCA TCA GAA      768
Pro Gln Leu Ile Leu Ser Leu Leu Glu Lys Gly Ala Ser Ala Ser Glu
                245                 250                 255

GCA ACT TTG GAA GGT TGA                                              786
Ala Thr Leu Glu Gly *
            260
```

(2) INFORMATION FOR SEQ ID NO:16:

(i) SEQUENCE CHARACTERISTICS:
        (A) LENGTH: 261 amino acids
        (B) TYPE: amino acid
        (D) TOPOLOGY: linear (ii) MOLECULE TYPE: protein (xi) SEQUENCE DESCRIPTION: SEQ ID NO:16:

```
Met Asp Ser Asn Asn Thr Ala Ala Val Lys Leu Glu Leu Lys Glu Ile
 1               5                  10                  15

Ala Lys Asp Tyr Glu Val Gly Phe Asp Ser Val Val Thr Val Leu Ala
            20                  25                  30

Tyr Val Tyr Ser Ser Arg Val Arg Pro Pro Lys Gly Val Ser Glu
        35                  40                  45

Cys Ala Asp Glu Asn Cys Cys His Val Ala Cys Arg Pro Ala Val Asp
    50                  55                  60

Phe Met Leu Glu Val Leu Tyr Leu Ala Phe Ile Phe Lys Ile Pro Glu
65                  70                  75                  80

Leu Ile Thr Leu Tyr Gln Arg His Leu Leu Asp Val Val Asp Lys Val
                85                  90                  95

Val Ile Glu Asp Thr Leu Val Ile Leu Lys Leu Ala Asn Ile Cys Gly
            100                 105                 110

Lys Ala Cys Met Lys Leu Leu Asp Arg Cys Lys Glu Ile Ile Val Lys
        115                 120                 125

Ser Asn Val Asp Met Val Ser Leu Glu Lys Ser Leu Pro Glu Glu Leu
    130                 135                 140

Val Lys Glu Ile Ile Asp Arg Arg Lys Glu Leu Gly Leu Glu Val Pro
145                 150                 155                 160

Lys Val Lys Lys His Val Ser Asn Val His Lys Ala Leu Asp Ser Asp
                165                 170                 175

Asp Ile Glu Leu Val Lys Leu Leu Lys Glu Asp His Thr Asn Leu
            180                 185                 190

Asp Asp Ala Cys Ala Leu His Phe Ala Val Ala Tyr Cys Asn Val Lys
        195                 200                 205

Thr Ala Thr Asp Leu Leu Lys Leu Asp Leu Ala Asp Val Asn His Arg
    210                 215                 220

Asn Pro Arg Gly Tyr Thr Val Leu His Val Ala Ala Met Arg Lys Glu
225                 230                 235                 240
```

-continued

```
Pro Gln Leu Ile Leu Ser Leu Leu Glu Lys Gly Ala Ser Ala Ser Glu
                245                 250                 255

Ala Thr Leu Glu Gly
        260
```

(2) INFORMATION FOR SEQ ID NO:17:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:17:

```
Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Asp Ala Leu Ala
                20                  25                  30

Val His Tyr Ala Val Gln His Cys Asn
            35                  40
```

(2) INFORMATION FOR SEQ ID NO:18:

(i) SEQUENCE CHARACTERISTICS:
        (A) LENGTH: 38 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:18:

```
Pro Thr Gly Lys Thr Ala Leu His Leu Ala Ala Glu Met Val Ser Pro
1               5                   10                  15

Asp Met Val Ser Val Leu Leu Asp His His Ala Asp Xaa Asn Phe Arg
                20                  25                  30

Thr Xaa Asp Gly Val Thr
        35
```

(2) INFORMATION FOR SEQ ID NO:19:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:19:

```
Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Asp Ala Leu Ala
                20                  25                  30

Val His Tyr Ala Val Gln His Cys Asn
            35                  40
```

(2) INFORMATION FOR SEQ ID NO:20:

(i) SEQUENCE CHARACTERISTICS:
        (A) LENGTH: 27 amino acids
        (B) TYPE: amino acid (C) STRANDEDNESS: Not Relevant
            (D) TOPOLOGY: Not Relevant (ii) MOLECULE TYPE: peptide (xi) SEQUENCE DESCRIPTION: SEQ ID NO:20:

Arg Arg Pro Asp Ser Lys Thr Ala Leu His Leu Ala Ala Glu Met Val
1               5                   10                  15

Ser Pro Asp Met Val Ser Val Leu Leu Asp Gln
            20                  25

(2) INFORMATION FOR SEQ ID NO:21:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:21:

Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Asp Ala Leu Ala
            20                  25                  30

Val His Tyr Ala Val Gln His Cys Asn
            35                  40

(2) INFORMATION FOR SEQ ID NO:22:

(i) SEQUENCE CHARACTERISTICS:
        (A) LENGTH: 27 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:22:

Arg Arg Pro Asp Ser Lys Thr Ala Leu His Leu Ala Ala Glu Met Val
1               5                   10                  15

Ser Pro Asp Met Val Ser Val Leu Leu Asp Gln
            20                  25

(2) INFORMATION FOR SEQ ID NO:23:

(i) SEQUENCE CHARACTERISTICS:
        (A) LENGTH: 41 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:23:

Ile Arg Arg Met Arg Arg Ala Leu Asp Ala Ala Asp Ile Glu Leu Val
1               5                   10                  15

Lys Leu Met Val Met Gly Glu Gly Leu Asp Leu Asp Asp Ala Leu Ala
            20                  25                  30

Val His Tyr Ala Val Gln His Cys Asn
            35                  40

-continued (2) INFORMATION FOR SEQ ID NO:24:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:24:

Pro Thr Gly Lys Thr Ala Leu His Leu Ala Ala Glu Met Val Ser Pro
1               5                   10                  15

Asp Met Val (2) INFORMATION FOR SEQ ID NO:25:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:25:

CAACAGCTTC GAAGCCGTCT TTGACGCGCC GGATG                                35

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:26:

CATCCGGCGC GTCAAAGACG GCTTCGAAGC TGTTG                                35

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:27:

GGAATTCAAT GGATTCGGTT GTGACTGTTT TG                                   32

(2) INFORMATION FOR SEQ ID NO:28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

-continued (xi) SEQUENCE DESCRIPTION: SEQ ID NO:28:

GGAATTCTAC AAATCTGTAT ACCATTGG                                                28

(2) INFORMATION FOR SEQ ID NO:29:

(i) SEQUENCE CHARACTERISTICS:
　　　　(A) LENGTH: 31 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "oligonucleotide"

(xi) SEQUENCE DESCRIPTION: SEQ ID NO:29:

CGGAATTCGA TCTCTTTAAT TTGTGAATTT C                                             31

(2) INFORMATION FOR SEQ ID NO:30:

(i) SEQUENCE CHARACTERISTICS:
　　　　(A) LENGTH: 29 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "oligonucleotide"

(xi) SEQUENCE DESCRIPTION: SEQ ID NO:30:

GGAATTCTCA ACAGTTCATA ATCTGGTCG                                                29

(2) INFORMATION FOR SEQ ID NO:31:

(i) SEQUENCE CHARACTERISTICS:
　　　　(A) LENGTH: 31 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "oligonucleotide"

(xi) SEQUENCE DESCRIPTION: SEQ ID NO:31:

GGAATTCAAT GGACTCCAAC AACACCGCCG C                                             31

(2) INFORMATION FOR SEQ ID NO:32:

(i) SEQUENCE CHARACTERISTICS:
　　　　(A) LENGTH: 33 base pairs
　　　　(B) TYPE: nucleic acid
　　　　(C) STRANDEDNESS: single
　　　　(D) TOPOLOGY: linear (ii) MOLECULE TYPE: other nucleic acid
　　　　(A) DESCRIPTION: /desc = "oligonucleotide"

(xi) SEQUENCE DESCRIPTION: SEQ ID NO:32:

GGAATTCTCA ACCTTCCAAA GTTGCTTCTG ATG                                           33